United States Patent
Fasan et al.

(10) Patent No.: US 9,663,532 B2
(45) Date of Patent: May 30, 2017

(54) ARTEMISININ DERIVATIVES, METHODS FOR THEIR PREPARATION AND THEIR USE AS ANTIMALARIAL AGENTS

(71) Applicant: University of Rochester, Rochester, NY (US)

(72) Inventors: Rudi Fasan, Rochester, NY (US); Kai-Dong Zhang, Langley (CA)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 14/438,833

(22) PCT Filed: Oct. 28, 2013

(86) PCT No.: PCT/US2013/067118
§ 371 (c)(1),
(2) Date: Apr. 27, 2015

(87) PCT Pub. No.: WO2014/070673
PCT Pub. Date: May 8, 2014

(65) Prior Publication Data
US 2015/0299217 A1   Oct. 22, 2015

Related U.S. Application Data

(60) Provisional application No. 61/719,758, filed on Oct. 29, 2012.

(51) Int. Cl.
*C07D 491/18* (2006.01)
*C07D 493/18* (2006.01)
*C12N 9/00* (2006.01)
*C12N 9/02* (2006.01)

(52) U.S. Cl.
CPC ......... *C07D 493/18* (2013.01); *C07D 491/18* (2013.01); *C12N 9/0042* (2013.01); *C12Y 106/02004* (2013.01)

(58) Field of Classification Search
None
See application file for complete search history.

(56) References Cited

U.S. PATENT DOCUMENTS

| | | | |
|---|---|---|---|
| 7,524,664 B2 | 4/2009 | Arnold et al. | |
| 8,101,399 B2* | 1/2012 | Dietrich | C12N 9/0071 435/252.1 |
| 2005/0059045 A1* | 3/2005 | Arnold | C12N 9/0071 435/6.12 |
| 2008/0187983 A1* | 8/2008 | Dietrich | C12N 9/0071 435/252.33 |
| 2009/0264311 A1* | 10/2009 | Arnold | C12N 9/0077 506/11 |
| 2010/0093651 A1 | 4/2010 | Brando et al. | |

FOREIGN PATENT DOCUMENTS

| | | |
|---|---|---|
| WO | WO-0004024 A1 | 1/2000 |
| WO | WO-2005083100 A1 | 9/2005 |
| WO | WO-2009047498 A2 | 4/2009 |
| WO | WO-2012109586 A2 | 8/2012 |

OTHER PUBLICATIONS

Korean Intellectual Property Office International Search Report and Written Opinion of the International Searching Authority for International Application No. PCT/US2013/067118 mailed Jan. 28, 2014 (15 pgs).
NCBI, Unnamed Protein Product [synthetic construct] GenBank Accession No. CAJ32086.1 (Jul. 13, 2006) (2 pages).
Zhang, Kaidong et al., "Controlled oxidation of remote $sp^3$ C—H bonds in artemisinin via P450 catalysts with fine tuned regio and stereoselectivity," Nov. 14, 2012, J Am Chem Soc., vol. 134, No. 45 (pp. 18695-18704).
European Patent Office—Partial Supplementary European Search Report for European Application No. 13850986.4 dated Aug. 31, 2016 (7 pages).

* cited by examiner

*Primary Examiner* — Suzanne M Noakes
(74) *Attorney, Agent, or Firm* — Harris Beach PLLC

(57) ABSTRACT

Derivatives of the antimalarial agent artemisinin, compositions comprising the derivatives, methods for preparing the derivatives, and their uses in pharmaceutical compositions intended for the treatment of parasitic infections are provided. Methods are provided for the production of artemisinin derivatives via functionalization of positions C7 and C6a, and optionally, in conjunction with modifications at positions C10 and C9, via chemoenzymatic methods. Recombinant cytochrome P450 polypeptides are also provided for use in the methods. The artemisinin derivatives can be used for the treatment of malaria and other parasitic infections, alone or in combination with other antiparasitic drugs.

6 Claims, 6 Drawing Sheets

Figure 1:
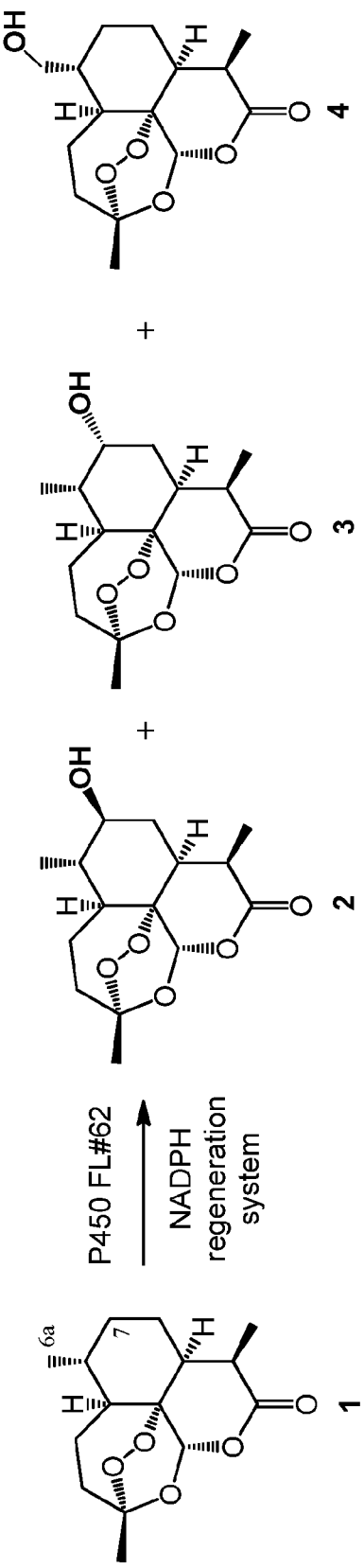

SEQUENCE LISTING

```
<160> NUMBER OF SEQ ID NOS: 17

<210> SEQ ID NO 1
<211> LENGTH: 1049
<212> TYPE: PRT
<213> ORGANISM: Bacillus megaterium

<400> SEQUENCE: 1
```

| Met | Thr | Ile | Lys | Glu | Met | Pro | Gln | Pro | Lys | Thr | Phe | Gly | Glu | Leu | Lys |
|---|---|---|---|---|---|---|---|---|---|---|---|---|---|---|---|
| 1 | | | | 5 | | | | | 10 | | | | | 15 | |

| Asn | Leu | Pro | Leu | Leu | Asn | Thr | Asp | Lys | Pro | Val | Gln | Ala | Leu | Met | Lys |
|---|---|---|---|---|---|---|---|---|---|---|---|---|---|---|---|
| | | | 20 | | | | | 25 | | | | | 30 | | |

| Ile | Ala | Asp | Glu | Leu | Gly | Glu | Ile | Phe | Lys | Phe | Glu | Ala | Pro | Gly | Arg |
|---|---|---|---|---|---|---|---|---|---|---|---|---|---|---|---|
| | | 35 | | | | 40 | | | | | 45 | | | | |

| Val | Thr | Arg | Tyr | Leu | Ser | Ser | Gln | Arg | Leu | Ile | Lys | Glu | Ala | Cys | Asp |
|---|---|---|---|---|---|---|---|---|---|---|---|---|---|---|---|
| | 50 | | | | | 55 | | | | | 60 | | | | |

| Glu | Ser | Arg | Phe | Asp | Lys | Asn | Leu | Ser | Gln | Ala | Leu | Lys | Phe | Val | Arg |
|---|---|---|---|---|---|---|---|---|---|---|---|---|---|---|---|
| 65 | | | | | 70 | | | | | 75 | | | | | 80 |

| Asp | Phe | Ala | Gly | Asp | Gly | Leu | Phe | Thr | Ser | Trp | Thr | His | Glu | Lys | Asn |
|---|---|---|---|---|---|---|---|---|---|---|---|---|---|---|---|
| | | | | 85 | | | | | 90 | | | | | 95 | |

| Trp | Lys | Lys | Ala | His | Asn | Ile | Leu | Leu | Pro | Ser | Phe | Ser | Gln | Gln | Ala |
|---|---|---|---|---|---|---|---|---|---|---|---|---|---|---|---|
| | | | 100 | | | | | 105 | | | | | 110 | | |

| Met | Lys | Gly | Tyr | His | Ala | Met | Met | Val | Asp | Ile | Ala | Val | Gln | Leu | Val |
|---|---|---|---|---|---|---|---|---|---|---|---|---|---|---|---|
| | | 115 | | | | 120 | | | | | 125 | | | | |

| Gln | Lys | Trp | Glu | Arg | Leu | Asn | Ala | Asp | Glu | His | Ile | Glu | Val | Pro | Glu |
|---|---|---|---|---|---|---|---|---|---|---|---|---|---|---|---|
| | 130 | | | | | 135 | | | | | 140 | | | | |

| Asp | Met | Thr | Arg | Leu | Thr | Leu | Asp | Thr | Ile | Gly | Leu | Cys | Gly | Phe | Asn |
|---|---|---|---|---|---|---|---|---|---|---|---|---|---|---|---|
| 145 | | | | | 150 | | | | | 155 | | | | | 160 |

| Tyr | Arg | Phe | Asn | Ser | Phe | Tyr | Arg | Asp | Gln | Pro | His | Pro | Phe | Ile | Thr |
|---|---|---|---|---|---|---|---|---|---|---|---|---|---|---|---|
| | | | | 165 | | | | | 170 | | | | | 175 | |

| Ser | Met | Val | Arg | Ala | Leu | Asp | Glu | Ala | Met | Asn | Lys | Leu | Gln | Arg | Ala |
|---|---|---|---|---|---|---|---|---|---|---|---|---|---|---|---|
| | | | 180 | | | | | 185 | | | | | 190 | | |

| Asn | Pro | Asp | Asp | Pro | Ala | Tyr | Asp | Glu | Asn | Lys | Arg | Gln | Phe | Gln | Glu |
|---|---|---|---|---|---|---|---|---|---|---|---|---|---|---|---|
| | | 195 | | | | 200 | | | | | 205 | | | | |

| Asp | Ile | Lys | Val | Met | Asn | Asp | Leu | Val | Asp | Lys | Ile | Ile | Ala | Asp | Arg |
|---|---|---|---|---|---|---|---|---|---|---|---|---|---|---|---|
| | 210 | | | | | 215 | | | | | 220 | | | | |

| Lys | Ala | Ser | Gly | Glu | Gln | Ser | Asp | Asp | Leu | Leu | Thr | His | Met | Leu | Asn |
|---|---|---|---|---|---|---|---|---|---|---|---|---|---|---|---|
| 225 | | | | | 230 | | | | | 235 | | | | | 240 |

| Gly | Lys | Asp | Pro | Glu | Thr | Gly | Glu | Pro | Leu | Asp | Asp | Glu | Asn | Ile | Arg |
|---|---|---|---|---|---|---|---|---|---|---|---|---|---|---|---|
| | | | | 245 | | | | | 250 | | | | | 255 | |

| Tyr | Gln | Ile | Ile | Thr | Phe | Leu | Ile | Ala | Gly | His | Glu | Thr | Thr | Ser | Gly |
|---|---|---|---|---|---|---|---|---|---|---|---|---|---|---|---|
| | | | 260 | | | | | 265 | | | | | 270 | | |

| Leu | Leu | Ser | Phe | Ala | Leu | Tyr | Phe | Leu | Val | Lys | Asn | Pro | His | Val | Leu |
|---|---|---|---|---|---|---|---|---|---|---|---|---|---|---|---|
| | | 275 | | | | 280 | | | | | 285 | | | | |

| Gln | Lys | Ala | Ala | Glu | Glu | Ala | Ala | Arg | Val | Leu | Val | Asp | Pro | Val | Pro |
|---|---|---|---|---|---|---|---|---|---|---|---|---|---|---|---|
| | 290 | | | | | 295 | | | | | 300 | | | | |

| Ser | Tyr | Lys | Gln | Val | Lys | Gln | Leu | Lys | Tyr | Val | Gly | Met | Val | Leu | Asn |
|---|---|---|---|---|---|---|---|---|---|---|---|---|---|---|---|
| 305 | | | | | 310 | | | | | 315 | | | | | 320 |

| Glu | Ala | Leu | Arg | Leu | Trp | Pro | Thr | Ala | Pro | Ala | Phe | Ser | Leu | Tyr | Ala |
|---|---|---|---|---|---|---|---|---|---|---|---|---|---|---|---|
| | | | | 325 | | | | | 330 | | | | | 335 | |

```
Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
```

```
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                1005

Ala Val  Glu Ala Thr Leu Met  Lys Ser Tyr Ala Asp  Val His Gln
    1010                1015                1020

Val Ser  Glu Ala Asp Ala Arg  Leu Trp Leu Gln Gln  Leu Glu Glu
    1025                1030                1035

Lys Gly  Arg Tyr Ala Lys Asp  Val Trp Ala Gly
    1040                1045

<210> SEQ ID NO 2
<211> LENGTH: 1065
<212> TYPE: PRT
<213> ORGANISM: Bacillus cereus
<400> SEQUENCE: 2

Met Asp Lys Lys Val Ser Ala Ile Pro Gln Pro Lys Thr Tyr Gly Pro
1               5                   10                  15

Leu Gly Asn Leu Pro Leu Ile Asp Lys Asp Lys Pro Thr Leu Ser Phe
            20                  25                  30

Ile Lys Ile Ala Glu Glu Tyr Gly Pro Ile Phe Gln Ile Gln Thr Leu
        35                  40                  45

Ser Asp Thr Ile Ile Val Ile Ser Gly His Glu Leu Val Ala Glu Val
    50                  55                  60

Cys Asp Glu Thr Arg Phe Asp Lys Ser Ile Glu Gly Ala Leu Ala Lys
65                  70                  75                  80
```

-continued

Val Arg Ala Phe Ala Gly Asp Gly Leu Phe Thr Ser Glu Thr Gln Glu
                85                  90                  95

Pro Asn Trp Lys Lys Ala His Asn Ile Leu Met Pro Thr Phe Ser Gln
                100                 105                 110

Arg Ala Met Lys Asp Tyr His Ala Met Met Val Asp Ile Ala Val Gln
            115                 120                 125

Leu Val Gln Lys Trp Ala Arg Leu Asn Pro Asn Glu Asn Val Asp Val
        130                 135                 140

Pro Glu Asp Met Thr Arg Leu Thr Leu Asp Thr Ile Gly Leu Cys Gly
145                 150                 155                 160

Phe Asn Tyr Arg Phe Asn Ser Phe Tyr Arg Glu Thr Pro His Pro Phe
                165                 170                 175

Ile Thr Ser Met Thr Arg Ala Leu Asp Glu Ala Met His Gln Leu Gln
                180                 185                 190

Arg Leu Asp Ile Glu Asp Lys Leu Met Trp Arg Thr Lys Arg Gln Phe
            195                 200                 205

Gln His Asp Ile Gln Ser Met Phe Ser Leu Val Asp Asn Ile Ile Ala
        210                 215                 220

Glu Arg Lys Ser Ser Gly Asn Gln Glu Glu Asn Asp Leu Leu Ser Arg
225                 230                 235                 240

Met Leu His Val Gln Asp Pro Glu Thr Gly Glu Lys Leu Asp Asp Glu
                245                 250                 255

Asn Ile Arg Phe Gln Ile Ile Thr Phe Leu Ile Ala Gly His Glu Thr
                260                 265                 270

Thr Ser Gly Leu Leu Ser Phe Ala Ile Tyr Phe Leu Leu Lys Asn Pro
            275                 280                 285

Asp Lys Leu Lys Lys Ala Tyr Glu Glu Val Asp Arg Val Leu Thr Asp
        290                 295                 300

Pro Thr Pro Thr Tyr Gln Gln Val Met Lys Leu Lys Tyr Ile Arg Met
305                 310                 315                 320

Ile Leu Asn Glu Ser Leu Arg Leu Trp Pro Thr Ala Pro Ala Phe Ser
                325                 330                 335

Leu Tyr Ala Lys Glu Asp Thr Val Ile Gly Gly Lys Tyr Pro Ile Lys
            340                 345                 350

Lys Gly Glu Asp Arg Ile Ser Val Leu Ile Pro Gln Leu His Arg Asp
        355                 360                 365

Lys Asp Ala Trp Gly Asp Asn Val Glu Glu Phe Gln Pro Glu Arg Phe
    370                 375                 380

Glu Asp Leu Asp Lys Val Pro His His Ala Tyr Lys Pro Phe Gly Asn
385                 390                 395                 400

Gly Gln Arg Ala Cys Ile Gly Met Gln Phe Ala Leu His Glu Ala Thr
                405                 410                 415

Leu Val Met Gly Met Leu Leu Gln His Phe Glu Phe Ile Asp Tyr Glu
            420                 425                 430

Asp Tyr Gln Leu Asp Val Lys Gln Thr Leu Thr Leu Lys Pro Gly Asp
        435                 440                 445

Phe Lys Ile Arg Ile Val Pro Arg Asn Gln Asn Ile Ser His Thr Thr
    450                 455                 460

Val Leu Ala Pro Thr Glu Lys Leu Lys Asn His Glu Ile Lys Gln
465                 470                 475                 480

Gln Val Gln Lys Thr Pro Ser Ile Ile Gly Ala Asp Asn Leu Ser Leu
                485                 490                 495

Leu Val Leu Tyr Gly Ser Asp Thr Gly Val Ala Glu Gly Ile Ala Arg

-continued

```
            500                 505                 510
Glu Leu Ala Asp Thr Ala Ser Leu Glu Gly Val Gln Thr Glu Val Ala
            515                 520                 525
Ala Leu Asn Asp Arg Ile Gly Ser Leu Pro Lys Glu Gly Ala Val Leu
            530                 535                 540
Ile Val Thr Ser Ser Tyr Asn Gly Lys Pro Pro Ser Asn Ala Gly Gln
545                 550                 555                 560
Phe Val Gln Trp Leu Glu Glu Leu Lys Pro Asp Glu Leu Lys Gly Val
                    565                 570                 575
Gln Tyr Ala Val Phe Gly Cys Gly Asp His Asn Trp Ala Ser Thr Tyr
                    580                 585                 590
Gln Arg Ile Pro Arg Tyr Ile Asp Glu Gln Met Ala Gln Lys Gly Ala
                    595                 600                 605
Thr Arg Phe Ser Thr Arg Gly Glu Ala Asp Ala Ser Gly Asp Phe Glu
            610                 615                 620
Glu Gln Leu Glu Gln Trp Lys Glu Ser Met Trp Ser Asp Ala Met Lys
625                 630                 635                 640
Ala Phe Gly Leu Glu Leu Asn Lys Asn Met Glu Lys Glu Arg Ser Thr
                    645                 650                 655
Leu Ser Leu Gln Phe Val Ser Arg Leu Gly Gly Ser Pro Leu Ala Arg
                    660                 665                 670
Thr Tyr Glu Ala Val Tyr Ala Ser Ile Leu Glu Asn Arg Glu Leu Gln
                    675                 680                 685
Ser Ser Ser Ser Glu Arg Ser Thr Arg His Ile Glu Ile Ser Leu Pro
            690                 695                 700
Glu Gly Ala Thr Tyr Lys Glu Gly Asp His Leu Gly Val Leu Pro Ile
705                 710                 715                 720
Asn Ser Glu Lys Asn Val Asn Arg Ile Leu Lys Arg Phe Gly Leu Asn
                    725                 730                 735
Gly Lys Asp Gln Val Ile Leu Ser Ala Ser Gly Arg Ser Val Asn His
            740                 745                 750
Ile Pro Leu Asp Ser Pro Val Arg Leu Tyr Asp Leu Leu Ser Tyr Ser
            755                 760                 765
Val Glu Val Gln Glu Ala Ala Thr Arg Ala Gln Ile Arg Glu Met Val
770                 775                 780
Thr Phe Thr Ala Cys Pro Pro His Lys Lys Glu Leu Glu Ser Leu Leu
785                 790                 795                 800
Glu Asp Gly Val Tyr His Glu Gln Ile Leu Lys Lys Arg Ile Ser Met
                    805                 810                 815
Leu Asp Leu Leu Glu Lys Tyr Glu Ala Cys Glu Ile Arg Phe Glu Arg
            820                 825                 830
Phe Leu Glu Leu Leu Pro Ala Leu Lys Pro Arg Tyr Tyr Ser Ile Ser
            835                 840                 845
Ser Ser Pro Leu Ile Ala Gln Asp Arg Leu Ser Ile Thr Val Gly Val
            850                 855                 860
Val Asn Ala Pro Ala Trp Ser Gly Glu Gly Thr Tyr Glu Gly Val Ala
865                 870                 875                 880
Ser Asn Tyr Leu Ala Gln Arg His Asn Lys Asp Glu Ile Ile Cys Phe
                    885                 890                 895
Ile Arg Thr Pro Gln Ser Asn Phe Gln Leu Pro Glu Asn Pro Glu Thr
            900                 905                 910
Pro Ile Ile Met Val Gly Pro Gly Thr Gly Ile Ala Pro Phe Arg Gly
            915                 920                 925
```

```
Phe Leu Gln Ala Arg Arg Val Gln Lys Gln Lys Gly Met Asn Leu Gly
        930                 935                 940

Glu Ala His Leu Tyr Phe Gly Cys Arg His Pro Glu Lys Asp Tyr Leu
945                 950                 955                 960

Tyr Arg Thr Glu Leu Glu Asn Asp Glu Arg Asp Gly Leu Ile Ser Leu
                965                 970                 975

His Thr Ala Phe Ser Arg Leu Glu Gly His Pro Lys Thr Tyr Val Gln
            980                 985                 990

His Val Ile Lys Glu Asp Arg Met  Asn Leu Ile Ser Leu  Leu Asp Asn
        995                 1000                1005

Gly Ala  His Leu Tyr Ile Cys  Gly Asp Gly Ser Lys  Met Ala Pro
    1010                 1015                1020

Asp Val  Glu Asp Thr Leu Cys  Gln Ala Tyr Gln Glu  Ile His Glu
    1025                 1030                1035

Val Ser  Glu Gln Glu Ala Arg  Asn Trp Leu Asp Arg  Leu Gln Asp
    1040                 1045                1050

Glu Gly  Arg Tyr Gly Lys Asp  Val Trp Ala Gly Ile
    1055                 1060                1065

<210> SEQ ID NO 3
<211> LENGTH: 1120
<212> TYPE: PRT
<213> ORGANISM: Aspergillus fumigatus

<400> SEQUENCE: 3

Met Ser Glu Ser Lys Thr Val Pro Ile Pro Gly Pro Arg Gly Val Pro
1               5                   10                  15

Leu Leu Gly Asn Ile Tyr Asp Ile Glu Gln Glu Val Pro Leu Arg Ser
                20                  25                  30

Ile Asn Leu Met Ala Asp Gln Tyr Gly Pro Ile Tyr Arg Leu Thr Thr
            35                  40                  45

Phe Gly Trp Ser Arg Val Phe Val Ser Thr His Glu Leu Val Asp Glu
    50                  55                  60

Val Cys Asp Glu Glu Arg Phe Thr Lys Val Val Thr Ala Gly Leu Asn
65                  70                  75                  80

Gln Ile Arg Asn Gly Val His Asp Gly Leu Phe Thr Ala Asn Phe Pro
                85                  90                  95

Gly Glu Glu Asn Trp Ala Ile Ala His Arg Val Leu Val Pro Ala Phe
            100                 105                 110

Gly Pro Leu Ser Ile Arg Gly Met Phe Asp Glu Met Tyr Asp Ile Ala
    115                 120                 125

Thr Gln Leu Val Met Lys Trp Ala Arg His Gly Pro Thr Val Pro Ile
130                 135                 140

Met Val Thr Asp Asp Phe Thr Arg Leu Thr Leu Asp Thr Ile Ala Leu
145                 150                 155                 160

Cys Ala Met Gly Thr Arg Phe Asn Ser Phe Tyr His Glu Glu Met His
                165                 170                 175

Pro Phe Val Glu Ala Met Val Gly Leu Leu Gln Gly Ser Gly Asp Arg
            180                 185                 190

Ala Arg Arg Pro Ala Leu Leu Asn Leu Pro Thr Ser Glu Asn Ser
    195                 200                 205

Lys Tyr Trp Asp Asp Ile Ala Phe Leu Arg Asn Leu Ala Gln Glu Leu
210                 215                 220

Val Glu Ala Arg Arg Lys Asn Pro Glu Asp Lys Lys Asp Leu Leu Asn
```

```
                225                 230                 235                 240
Ala Leu Ile Leu Gly Arg Asp Pro Lys Thr Gly Lys Gly Leu Thr Asp
                        245                 250                 255
Glu Ser Ile Ile Asp Asn Met Ile Thr Phe Leu Ile Ala Gly His Glu
                        260                 265                 270
Thr Thr Ser Gly Leu Leu Ser Phe Leu Phe Tyr Tyr Leu Leu Lys Thr
                        275                 280                 285
Pro Asn Ala Tyr Lys Lys Ala Gln Glu Glu Val Asp Ser Val Val Gly
                        290                 295                 300
Arg Arg Lys Ile Thr Val Glu Asp Met Ser Arg Leu Pro Tyr Leu Asn
305                             310                 315                 320
Ala Val Met Arg Glu Thr Leu Arg Leu Arg Ser Thr Ala Pro Leu Ile
                        325                 330                 335
Ala Val His Ala His Pro Glu Lys Asn Lys Glu Asp Pro Val Thr Leu
                        340                 345                 350
Gly Gly Gly Lys Tyr Val Leu Asn Lys Asp Glu Pro Ile Val Ile Ile
                        355                 360                 365
Leu Asp Lys Leu His Arg Asp Pro Gln Val Tyr Gly Pro Asp Ala Glu
            370                 375                 380
Glu Phe Lys Pro Glu Arg Met Leu Asp Glu Asn Phe Glu Lys Leu Pro
385                             390                 395                 400
Lys Asn Ala Trp Lys Pro Phe Gly Asn Gly Met Arg Ala Cys Ile Gly
                        405                 410                 415
Arg Pro Phe Ala Trp Gln Glu Ala Leu Leu Val Val Ala Ile Leu Leu
                        420                 425                 430
Gln Asn Phe Asn Phe Gln Met Asp Asp Pro Ser Tyr Asn Leu His Ile
                        435                 440                 445
Lys Gln Thr Leu Thr Ile Lys Pro Lys Asp Phe His Met Arg Ala Thr
            450                 455                 460
Leu Arg His Gly Leu Asp Ala Thr Lys Leu Gly Ile Ala Leu Ser Gly
465                             470                 475                 480
Ser Ala Asp Arg Ala Pro Pro Glu Ser Ser Gly Ala Ala Ser Arg Val
                        485                 490                 495
Arg Lys Gln Ala Thr Pro Pro Ala Gly Gln Leu Lys Pro Met His Ile
                        500                 505                 510
Phe Phe Gly Ser Asn Thr Gly Thr Cys Glu Thr Phe Ala Arg Arg Leu
                        515                 520                 525
Ala Asp Asp Ala Val Gly Tyr Gly Phe Ala Ala Asp Val Gln Ser Leu
            530                 535                 540
Asp Ser Ala Met Gln Asn Val Pro Lys Asp Glu Pro Val Val Phe Ile
545                             550                 555                 560
Thr Ala Ser Tyr Glu Gly Gln Pro Pro Asp Asn Ala Ala His Phe Phe
                        565                 570                 575
Glu Trp Leu Ser Ala Leu Lys Glu Asn Glu Leu Glu Gly Val Asn Tyr
                        580                 585                 590
Ala Val Phe Gly Cys Gly His His Asp Trp Gln Ala Thr Phe His Arg
                        595                 600                 605
Ile Pro Lys Ala Val Asn Gln Leu Val Ala Glu His Gly Gly Asn Arg
            610                 615                 620
Leu Cys Asp Leu Gly Leu Ala Asp Ala Ala Asn Ser Asp Met Phe Thr
625                             630                 635                 640
Asp Phe Asp Ser Trp Gly Glu Ser Thr Phe Trp Pro Ala Ile Thr Ser
                        645                 650                 655
```

-continued

```
Lys Phe Gly Gly Gly Lys Ser Asp Glu Pro Lys Pro Ser Ser Ser Leu
            660                 665                 670

Gln Val Glu Val Ser Thr Gly Met Arg Ala Ser Thr Leu Gly Leu Gln
        675                 680                 685

Leu Gln Glu Gly Leu Val Ile Asp Asn Gln Leu Leu Ser Ala Pro Asp
    690                 695                 700

Val Pro Ala Lys Arg Met Ile Arg Phe Lys Leu Pro Ser Asp Met Ser
705                 710                 715                 720

Tyr Arg Cys Gly Asp Tyr Leu Ala Val Leu Pro Val Asn Pro Thr Ser
                725                 730                 735

Val Val Arg Arg Ala Ile Arg Arg Phe Asp Leu Pro Trp Asp Ala Met
            740                 745                 750

Leu Thr Ile Arg Lys Pro Ser Gln Ala Pro Lys Gly Ser Thr Ser Ile
        755                 760                 765

Pro Leu Asp Thr Pro Ile Ser Ala Phe Glu Leu Leu Ser Thr Tyr Val
    770                 775                 780

Glu Leu Ser Gln Pro Ala Ser Lys Arg Asp Leu Thr Ala Leu Ala Asp
785                 790                 795                 800

Ala Ala Ile Thr Asp Ala Asp Ala Gln Ala Glu Leu Arg Tyr Leu Ala
                805                 810                 815

Ser Ser Pro Thr Arg Phe Thr Glu Glu Ile Val Lys Lys Arg Met Ser
            820                 825                 830

Pro Leu Asp Leu Leu Ile Arg Tyr Pro Ser Ile Lys Leu Pro Val Gly
        835                 840                 845

Asp Phe Leu Ala Met Leu Pro Pro Met Arg Val Arg Gln Tyr Ser Ile
    850                 855                 860

Ser Ser Ser Pro Leu Ala Asp Pro Ser Glu Cys Ser Ile Thr Phe Ser
865                 870                 875                 880

Val Leu Asn Ala Pro Ala Leu Ala Ala Ser Leu Pro Pro Ala Glu
                885                 890                 895

Arg Ala Glu Ala Glu Gln Tyr Met Gly Val Ala Ser Thr Tyr Leu Ser
            900                 905                 910

Glu Leu Lys Pro Gly Arg Ala His Ile Ala Val Arg Pro Ser His
        915                 920                 925

Ser Gly Phe Lys Pro Pro Met Asp Leu Lys Ala Pro Met Ile Met Ala
    930                 935                 940

Cys Ala Gly Ser Gly Leu Ala Pro Phe Arg Gly Phe Ile Met Asp Arg
945                 950                 955                 960

Ala Glu Lys Ile Arg Gly Arg Ser Ser Val Gly Ala Asp Gly Gln
                965                 970                 975

Leu Pro Glu Val Glu Gln Pro Ala Lys Ala Ile Leu Tyr Val Gly Cys
            980                 985                 990

Arg Thr Lys Gly Lys Asp Asp Ile His Ala Thr Glu Leu Ala Glu Trp
        995                 1000                1005

Ala Gln Leu Gly Ala Val Asp Val Arg Trp Ala Tyr Ser Arg Pro
    1010                1015                1020

Glu Asp Gly Ser Lys Gly Arg His Val Gln Asp Leu Met Leu Glu
    1025                1030                1035

Asp Arg Glu Glu Leu Val Ser Leu Phe Asp Gln Gly Ala Arg Ile
    1040                1045                1050

Tyr Val Cys Gly Ser Thr Gly Val Gly Asn Gly Val Arg Gln Ala
    1055                1060                1065
```

```
Cys Lys Asp Ile Tyr Leu Glu Arg Arg Arg Gln Leu Arg Gln Ala
    1070                1075                1080

Ala Arg Glu Arg Gly Glu Glu Val Pro Ala Glu Glu Asp Glu Asp
    1085                1090                1095

Ala Ala Ala Glu Gln Phe Leu Asp Asn Leu Arg Thr Lys Glu Arg
    1100                1105                1110

Tyr Ala Thr Asp Val Phe Thr
    1115                1120

<210> SEQ ID NO 4
<211> LENGTH: 1049
<212> TYPE: PRT
<213> ORGANISM: Artificial Sequence
<220> FEATURE:
<223> OTHER INFORMATION: Synthetic sequence.

<400> SEQUENCE: 4

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Ala Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300
```

-continued

```
Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
            325                 330                 335

Lys Glu Asp Thr Val Leu Gly Gly Glu Tyr Pro Leu Glu Lys Gly Asp
        340                 345                 350

Glu Leu Met Val Leu Ile Pro Gln Leu His Arg Asp Lys Thr Ile Trp
    355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
        420                 425                 430

Asp Ile Lys Glu Thr Leu Thr Leu Lys Pro Glu Gly Phe Val Val Lys
    435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
        500                 505                 510

Gln Val Ala Thr Leu Asp Ser His Ala Gly Asn Leu Pro Arg Glu Gly
    515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ala Ala
        580                 585                 590

Lys Gly Ala Glu Asn Ile Ala Asp Arg Gly Glu Ala Asp Ala Ser Asp
    595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
            645                 650                 655

Ala Lys Met His Gly Ala Phe Ser Thr Asn Val Val Ala Ser Lys Glu
        660                 665                 670

Leu Gln Gln Pro Gly Ser Ala Arg Ser Thr Arg His Leu Glu Ile Glu
    675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
```

```
                    725                 730                 735
Ala His Leu Pro Leu Ala Lys Thr Val Ser Val Glu Glu Leu Leu Gln
                740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
        770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
        1010                1015                1020

Val Ser Glu Ala Asp Ala Arg Leu Trp Leu Gln Gln Leu Glu Glu
        1025                1030                1035

Lys Gly Arg Tyr Ala Lys Asp Val Trp Ala Gly
        1040                1045

<210> SEQ ID NO 5
<211> LENGTH: 1049
<212> TYPE: PRT
<213> ORGANISM: Artificial Sequence
<220> FEATURE:
<223> OTHER INFORMATION: Synthetic sequence.

<400> SEQUENCE: 5

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Cys
```

-continued

```
                35                  40                  45
Val Thr Arg Tyr Leu Ser Ser Gln Arg Leu Ile Lys Glu Ala Cys Asp
 50                  55                  60

Glu Ser Arg Phe Asp Lys Asn Leu Ser Gln Ala Leu Lys Ala Val Arg
 65                  70                  75                  80

Asp Phe Ala Gly Asp Gly Leu Ala Thr Ser Trp Thr His Glu Ile Asn
                 85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Val
                115                 120                 125

Gln Lys Trp Glu Arg Leu Asn Ala Asp Glu His Ile Glu Val Ser Glu
                130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Leu Gln Arg Ala
                180                 185                 190

Asn Pro Asp Asp Pro Ala Tyr Asp Glu Asn Lys Arg Gln Cys Gln Glu
                195                 200                 205

Asp Ile Lys Val Met Asn Asp Leu Val Asp Lys Ile Ile Ala Asp Arg
                210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
                275                 280                 285

Gln Lys Val Ala Glu Glu Ala Ala Arg Val Leu Val Asp Pro Val Pro
                290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Val Met Val Leu Ile Pro Gln Leu His Arg Asp Lys Thr Ile Trp
                355                 360                 365

Gly Asp Asp Val Glu Glu Phe Arg Pro Glu Arg Phe Glu Asn Pro Ser
                370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
                435                 440                 445

Ala Lys Ser Lys Lys Ile Pro Leu Gly Gly Ile Pro Ser Pro Ser Thr
450                 455                 460
```

```
Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                    485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
                515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
                580                 585                 590

Lys Gly Ala Glu Asn Ile Ala Asp Arg Gly Glu Ala Asp Ala Ser Asp
                595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
                675                 680                 685

Leu Pro Lys Glu Ala Ser Tyr Gln Glu Gly Asp His Leu Gly Val Ile
                690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
                740                 745                 750

Tyr Val Glu Leu Gln Asp Pro Val Thr Arg Thr Gln Leu Arg Ala Met
                755                 760                 765

Ala Ala Lys Thr Val Cys Pro Pro His Lys Val Glu Leu Glu Ala Leu
                770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
                850                 855                 860

Ala Ser Asn Tyr Leu Ala Glu Leu Gln Glu Gly Asp Thr Ile Thr Cys
865                 870                 875                 880
```

-continued

```
Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 6
<211> LENGTH: 1049
<212> TYPE: PRT
<213> ORGANISM: Artificial Sequence
<220> FEATURE:
<223> OTHER INFORMATION: Synthetic sequence

<400> SEQUENCE: 6

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Ala Val Arg
65                  70                  75                  80

Asp Phe Leu Gly Asp Gly Leu Phe Thr Ser Trp Thr His Glu Ile Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Leu Gln Arg Ala
            180                 185                 190
```

-continued

```
Asn Pro Asp Asp Pro Ala Tyr Asp Glu Asn Lys Arg Gln Cys Gln Glu
            195                 200                 205

Asp Ile Lys Val Met Asn Asp Leu Val Asp Lys Ile Ile Ala Asp Arg
210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Tyr Pro Leu Glu Lys Gly Asp
                340                 345                 350

Glu Val Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
        370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
```

```
                    610             615             620
Val Ala Ala Tyr Phe Asn Leu Asp Ile Glu Asn Ser Glu Asp Asn Lys
625             630             635             640

Ser Thr Leu Ser Leu Gln Phe Val Asp Ser Ala Ala Asp Met Pro Leu
                645             650             655

Ala Lys Met His Gly Ala Phe Ser Thr Asn Val Val Ala Ser Lys Glu
                660             665             670

Leu Gln Gln Pro Gly Ser Ala Arg Ser Thr Arg His Leu Glu Ile Glu
                675             680             685

Leu Pro Lys Glu Ala Ser Tyr Gln Glu Gly Asp His Leu Gly Val Ile
            690             695             700

Pro Arg Asn Tyr Glu Gly Ile Val Asn Arg Val Thr Ala Arg Phe Gly
705             710             715             720

Leu Asp Ala Ser Gln Gln Ile Arg Leu Glu Ala Glu Glu Lys Leu
                725             730             735

Ala His Leu Pro Leu Ala Lys Thr Val Ser Val Glu Glu Leu Leu Gln
                740             745             750

Tyr Val Glu Leu Gln Asp Pro Val Thr Arg Thr Gln Leu Arg Ala Met
            755             760             765

Ala Ala Lys Thr Val Cys Pro Pro His Lys Val Glu Leu Glu Ala Leu
770             775             780

Leu Glu Lys Gln Ala Tyr Lys Glu Gln Val Leu Ala Lys Arg Leu Thr
785             790             795             800

Met Leu Glu Leu Leu Glu Lys Tyr Pro Ala Cys Glu Met Lys Phe Ser
                805             810             815

Glu Phe Ile Ala Leu Leu Pro Ser Ile Arg Pro Arg Tyr Tyr Ser Ile
                820             825             830

Ser Ser Ser Pro Arg Val Asp Glu Lys Gln Ala Ser Ile Thr Val Ser
                835             840             845

Val Val Ser Gly Glu Ala Trp Ser Gly Tyr Gly Glu Tyr Lys Gly Ile
            850             855             860

Ala Ser Asn Tyr Leu Ala Glu Leu Gln Glu Gly Asp Thr Ile Thr Cys
865             870             875             880

Phe Ile Ser Thr Pro Gln Ser Glu Phe Thr Leu Pro Lys Asp Pro Glu
                885             890             895

Thr Pro Leu Ile Met Val Gly Pro Gly Thr Gly Val Ala Pro Phe Arg
                900             905             910

Gly Phe Val Gln Ala Arg Lys Gln Leu Lys Glu Gln Gly Gln Ser Leu
            915             920             925

Gly Glu Ala His Leu Tyr Phe Gly Cys Arg Ser Pro His Glu Asp Tyr
930             935             940

Leu Tyr Gln Glu Glu Leu Glu Asn Ala Gln Ser Glu Gly Ile Ile Thr
945             950             955             960

Leu His Thr Ala Phe Ser Arg Met Pro Asn Gln Pro Lys Thr Tyr Val
                965             970             975

Gln His Val Met Glu Gln Asp Gly Lys Lys Leu Ile Glu Leu Leu Asp
            980             985             990

Gln Gly Ala His Phe Tyr Ile Cys  Gly Asp Gly Ser Gln  Met Ala Pro
            995             1000            1005

Ala Val  Glu Ala Thr Leu Met  Lys Ser Tyr Ala Asp  Val His Gln
    1010            1015            1020

Val Ser  Glu Ala Asp Ala Arg  Leu Trp Leu Gln Gln  Leu Glu Glu
    1025            1030            1035
```

```
                Lys Gly Arg Tyr Ala Lys Asp Val Trp Ala Gly
                    1040                1045

<210> SEQ ID NO 7
<211> LENGTH: 1049
<212> TYPE: PRT
<213> ORGANISM: Artificial Sequence
<220> FEATURE:
<223> OTHER INFORMATION: Synthetic sequence

<400> SEQUENCE: 7

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Ala Val Arg
65                  70                  75                  80

Asp Phe Leu Gly Asp Gly Leu Phe Thr Ser Trp Thr His Glu Ile Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Val Pro Ala Phe Ser Leu Tyr Ala
                325                 330                 335

Lys Glu Asp Thr Val Leu Gly Gly Glu Tyr Pro Leu Glu Lys Gly Asp
            340                 345                 350
```

-continued

```
Glu Val Met Val Leu Ile Pro Gln Leu His Arg Asp Lys Thr Ile Trp
            355                 360                 365

Gly Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
    515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
    595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
    675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
    755                 760                 765
```

-continued

```
Ala Ala Lys Thr Val Cys Pro Pro His Lys Val Glu Leu Glu Ala Leu
        770             775             780

Leu Glu Lys Gln Ala Tyr Lys Glu Gln Val Leu Ala Lys Arg Leu Thr
785             790             795             800

Met Leu Glu Leu Leu Glu Lys Tyr Pro Ala Cys Glu Met Lys Phe Ser
                805             810             815

Glu Phe Ile Ala Leu Leu Pro Ser Ile Arg Pro Arg Tyr Tyr Ser Ile
            820             825             830

Ser Ser Ser Pro Arg Val Asp Glu Lys Gln Ala Ser Ile Thr Val Ser
        835             840             845

Val Val Ser Gly Glu Ala Trp Ser Gly Tyr Gly Glu Tyr Lys Gly Ile
850             855             860

Ala Ser Asn Tyr Leu Ala Glu Leu Gln Glu Gly Asp Thr Ile Thr Cys
865             870             875             880

Phe Ile Ser Thr Pro Gln Ser Glu Phe Thr Leu Pro Lys Asp Pro Glu
                885             890             895

Thr Pro Leu Ile Met Val Gly Pro Gly Thr Gly Val Ala Pro Phe Arg
            900             905             910

Gly Phe Val Gln Ala Arg Lys Gln Leu Lys Glu Gln Gly Gln Ser Leu
        915             920             925

Gly Glu Ala His Leu Tyr Phe Gly Cys Arg Ser Pro His Glu Asp Tyr
930             935             940

Leu Tyr Gln Glu Glu Leu Glu Asn Ala Gln Ser Glu Gly Ile Ile Thr
945             950             955             960

Leu His Thr Ala Phe Ser Arg Met Pro Asn Gln Pro Lys Thr Tyr Val
                965             970             975

Gln His Val Met Glu Gln Asp Gly Lys Lys Leu Ile Glu Leu Leu Asp
            980             985             990

Gln Gly Ala His Phe Tyr Ile Cys Gly Asp Gly Ser Gln Met Ala Pro
        995            1000            1005

Ala Val Glu Ala Thr Leu Met Lys Ser Tyr Ala Asp Val His Gln
       1010            1015            1020

Val Ser Glu Ala Asp Ala Arg Leu Trp Leu Gln Gln Leu Glu Glu
       1025            1030            1035

Lys Gly Arg Tyr Ala Lys Asp Val Trp Ala Gly
       1040            1045

<210> SEQ ID NO 8
<211> LENGTH: 1049
<212> TYPE: PRT
<213> ORGANISM: Artificial Sequence
<220> FEATURE:
<223> OTHER INFORMATION: Synthetic sequence

<400> SEQUENCE: 8

Met Thr Ile Lys Glu Met Pro Gln Pro Lys Thr Phe Gly Glu Leu Lys
1               5                  10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80
```

-continued

Asp Ser Val Gly Asp Gly Leu Ala Thr Ser Trp Thr His Glu Lys Asn
            85                  90                  95

Trp Lys Lys Ala His Asn Ile Leu Leu Pro Ser Phe Ser Gln Gln Ala
        100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Thr Leu Asp Glu Val Met Asn Lys Leu Gln Arg Ala
        180                 185                 190

Asn Pro Asp Asp Pro Val Tyr Asp Glu Asn Lys Arg Gln Cys Gln Glu
        195                 200                 205

Asp Ile Lys Val Met Asn Asp Leu Val Asp Lys Ile Ile Ala Asp Arg
210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
        290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Val Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
        370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro

```
                500             505             510
Gln Val Ala Thr Leu Asp Ser His Ala Gly Asn Leu Pro Arg Glu Gly
            515             520             525
Ala Val Leu Ile Val Thr Ala Ser Tyr Asn Gly His Pro Pro Asp Asn
            530             535             540
Ala Lys Gln Phe Val Asp Trp Leu Asp Gln Ala Ser Ala Asp Glu Val
545             550             555             560
Lys Gly Val Arg Tyr Ser Val Phe Gly Cys Gly Asp Lys Asn Trp Ala
            565             570             575
Thr Thr Tyr Gln Lys Val Pro Ala Phe Ile Asp Glu Thr Leu Ala Ala
            580             585             590
Lys Gly Ala Glu Asn Ile Ala Asp Arg Gly Glu Ala Asp Ala Ser Asp
            595             600             605
Asp Phe Glu Gly Thr Tyr Glu Glu Trp Arg Glu His Met Trp Ser Asp
            610             615             620
Val Ala Ala Tyr Phe Asn Leu Asp Ile Glu Asn Ser Glu Asp Asn Lys
625             630             635             640
Ser Thr Leu Ser Leu Gln Phe Val Asp Ser Ala Ala Asp Met Pro Leu
            645             650             655
Ala Lys Met His Gly Ala Phe Ser Thr Asn Val Val Ala Ser Lys Glu
            660             665             670
Leu Gln Gln Pro Gly Ser Ala Arg Ser Thr Arg His Leu Glu Ile Glu
            675             680             685
Leu Pro Lys Glu Ala Ser Tyr Gln Glu Gly Asp His Leu Gly Val Ile
            690             695             700
Pro Arg Asn Tyr Glu Gly Ile Val Asn Arg Val Thr Ala Arg Phe Gly
705             710             715             720
Leu Asp Ala Ser Gln Gln Ile Arg Leu Glu Ala Glu Glu Lys Leu
            725             730             735
Ala His Leu Pro Leu Ala Lys Thr Val Ser Val Glu Glu Leu Leu Gln
            740             745             750
Tyr Val Glu Leu Gln Asp Pro Val Thr Arg Thr Gln Leu Arg Ala Met
            755             760             765
Ala Ala Lys Thr Val Cys Pro Pro His Lys Val Glu Leu Glu Ala Leu
            770             775             780
Leu Glu Lys Gln Ala Tyr Lys Glu Gln Val Leu Ala Lys Arg Leu Thr
785             790             795             800
Met Leu Glu Leu Leu Glu Lys Tyr Pro Ala Cys Glu Met Lys Phe Ser
            805             810             815
Glu Phe Ile Ala Leu Leu Pro Ser Ile Arg Pro Arg Tyr Tyr Ser Ile
            820             825             830
Ser Ser Ser Pro Arg Val Asp Glu Lys Gln Ala Ser Ile Thr Val Ser
            835             840             845
Val Val Ser Gly Glu Ala Trp Ser Gly Tyr Gly Glu Tyr Lys Gly Ile
            850             855             860
Ala Ser Asn Tyr Leu Ala Glu Leu Gln Glu Gly Asp Thr Ile Thr Cys
865             870             875             880
Phe Ile Ser Thr Pro Gln Ser Glu Phe Thr Leu Pro Lys Asp Pro Glu
            885             890             895
Thr Pro Leu Ile Met Val Gly Pro Gly Thr Gly Val Ala Pro Phe Arg
            900             905             910
Gly Phe Val Gln Ala Arg Lys Gln Leu Lys Glu Gln Gly Gln Ser Leu
            915             920             925
```

```
Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 9
<211> LENGTH: 1049
<212> TYPE: PRT
<213> ORGANISM: Artificial Sequence
<220> FEATURE:
<223> OTHER INFORMATION: Synthetic sequence

<400> SEQUENCE: 9

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ser Arg
65                  70                  75                  80

Asp Val Ala Gly Asp Gly Leu Ala Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Thr Leu Asp Glu Val Met Asn Lys Leu Gln Arg Ala
            180                 185                 190

Asn Pro Asp Asp Pro Val Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240
```

-continued

Gly Lys Asp Pro Glu Thr Gly Glu Pro Leu Asp Asp Gly Asn Ile Ser
                245             250             255

Tyr Gln Ile Ile Thr Phe Leu Ile Ala Gly His Glu Thr Thr Ser Gly
            260             265             270

Leu Leu Ser Phe Ala Leu Tyr Phe Leu Val Lys Asn Pro His Val Leu
        275             280             285

Gln Lys Val Ala Glu Ala Ala Arg Val Leu Val Asp Pro Val Pro
    290             295             300

Ser Tyr Lys Gln Val Lys Gln Leu Lys Tyr Val Gly Met Val Leu Asn
305             310             315             320

Glu Ala Leu Arg Leu Trp Pro Thr Ala Pro Ala Phe Ser Leu Tyr Ala
                325             330             335

Lys Glu Asp Thr Val Leu Gly Gly Glu Tyr Pro Leu Glu Lys Gly Asp
            340             345             350

Glu Val Met Val Leu Ile Pro Gln Leu His Arg Asp Lys Thr Ile Trp
        355             360             365

Gly Asp Asp Val Glu Glu Phe Arg Pro Glu Arg Phe Glu Asn Pro Ser
    370             375             380

Ala Ile Pro Gln His Ala Phe Lys Pro Phe Gly Asn Gly Gln Arg Ala
385             390             395             400

Cys Ile Gly Gln Gln Phe Ala Leu His Glu Ala Thr Leu Val Leu Gly
                405             410             415

Met Met Leu Lys His Phe Asp Phe Glu Asp His Thr Asn Tyr Glu Leu
            420             425             430

Asp Ile Lys Glu Thr Leu Thr Leu Lys Pro Glu Gly Phe Val Val Lys
        435             440             445

Ala Lys Ser Lys Lys Ile Pro Leu Gly Gly Ile Pro Ser Pro Ser Thr
    450             455             460

Glu Gln Ser Ala Lys Lys Val Arg Lys Lys Ala Glu Asn Ala His Asn
465             470             475             480

Thr Pro Leu Leu Val Leu Tyr Gly Ser Asn Met Gly Thr Ala Glu Gly
                485             490             495

Thr Ala Arg Asp Leu Ala Asp Ile Ala Met Ser Lys Gly Phe Ala Pro
            500             505             510

Gln Val Ala Thr Leu Asp Ser His Ala Gly Asn Leu Pro Arg Glu Gly
        515             520             525

Ala Val Leu Ile Val Thr Ala Ser Tyr Asn Gly His Pro Pro Asp Asn
    530             535             540

Ala Lys Gln Phe Val Asp Trp Leu Asp Gln Ala Ser Ala Asp Glu Val
545             550             555             560

Lys Gly Val Arg Tyr Ser Val Phe Gly Cys Gly Asp Lys Asn Trp Ala
                565             570             575

Thr Thr Tyr Gln Lys Val Pro Ala Phe Ile Asp Glu Thr Leu Ala Ala
            580             585             590

Lys Gly Ala Glu Asn Ile Ala Asp Arg Gly Glu Ala Asp Ala Ser Asp
        595             600             605

Asp Phe Glu Gly Thr Tyr Glu Glu Trp Arg Glu His Met Trp Ser Asp
    610             615             620

Val Ala Ala Tyr Phe Asn Leu Asp Ile Glu Asn Ser Glu Asp Asn Lys
625             630             635             640

Ser Thr Leu Ser Leu Gln Phe Val Asp Ser Ala Asp Met Pro Leu
                645             650             655

```
Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 10
<211> LENGTH: 1049
<212> TYPE: PRT
```

<213> ORGANISM: Artificial Sequence
<220> FEATURE:
<223> OTHER INFORMATION: Synthetic sequence

<400> SEQUENCE: 10

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
50                  55                  60

Glu Ser Arg Phe Asp Lys Asn Leu Ser Gln Ala Leu Lys Phe Ser Arg
65                  70                  75                  80

Asp Ile Ala Gly Asp Gly Leu Ala Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Thr Leu Asp Glu Val Met Asn Lys Leu Gln Arg Ala
            180                 185                 190

Asn Pro Asp Asp Pro Val Tyr Asp Glu Asn Lys Arg Gln Cys Gln Glu
        195                 200                 205

Asp Ile Lys Val Met Asn Asp Leu Val Asp Lys Ile Ile Ala Asp Arg
        210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala

-continued

```
            385                 390                 395                 400
        Cys Ile Gly Gln Gln Phe Ala Leu His Glu Ala Thr Leu Val Leu Gly
                        405                 410                 415
        Met Met Leu Lys His Phe Asp Phe Glu Asp His Thr Asn Tyr Glu Leu
                        420                 425                 430
        Asp Ile Lys Glu Thr Leu Thr Leu Lys Pro Glu Gly Phe Val Val Lys
                        435                 440                 445
        Ala Lys Ser Lys Lys Ile Pro Leu Gly Gly Ile Pro Ser Pro Ser Thr
        450                 455                 460
        Glu Gln Ser Ala Lys Lys Val Arg Lys Ala Glu Asn Ala His Asn
        465                 470                 475                 480
        Thr Pro Leu Leu Val Leu Tyr Gly Ser Asn Met Gly Thr Ala Glu Gly
                            485                 490                 495
        Thr Ala Arg Asp Leu Ala Asp Ile Ala Met Ser Lys Gly Phe Ala Pro
                        500                 505                 510
        Gln Val Ala Thr Leu Asp Ser His Ala Gly Asn Leu Pro Arg Glu Gly
                        515                 520                 525
        Ala Val Leu Ile Val Thr Ala Ser Tyr Asn Gly His Pro Pro Asp Asn
        530                 535                 540
        Ala Lys Gln Phe Val Asp Trp Leu Asp Gln Ala Ser Ala Asp Glu Val
        545                 550                 555                 560
        Lys Gly Val Arg Tyr Ser Val Phe Gly Cys Gly Asp Lys Asn Trp Ala
                        565                 570                 575
        Thr Thr Tyr Gln Lys Val Pro Ala Phe Ile Asp Glu Thr Leu Ala Ala
                        580                 585                 590
        Lys Gly Ala Glu Asn Ile Ala Asp Arg Gly Glu Ala Asp Ala Ser Asp
                        595                 600                 605
        Asp Phe Glu Gly Thr Tyr Glu Glu Trp Arg Glu His Met Trp Ser Asp
                        610                 615                 620
        Val Ala Ala Tyr Phe Asn Leu Asp Ile Glu Asn Ser Glu Asp Asn Lys
        625                 630                 635                 640
        Ser Thr Leu Ser Leu Gln Phe Val Asp Ser Ala Ala Asp Met Pro Leu
                        645                 650                 655
        Ala Lys Met His Gly Ala Phe Ser Thr Asn Val Val Ala Ser Lys Glu
                        660                 665                 670
        Leu Gln Gln Pro Gly Ser Ala Arg Ser Thr Arg His Leu Glu Ile Glu
                        675                 680                 685
        Leu Pro Lys Glu Ala Ser Tyr Gln Glu Gly Asp His Leu Gly Val Ile
                        690                 695                 700
        Pro Arg Asn Tyr Glu Gly Ile Val Asn Arg Val Thr Ala Arg Phe Gly
        705                 710                 715                 720
        Leu Asp Ala Ser Gln Gln Ile Arg Leu Glu Ala Glu Glu Lys Leu
                        725                 730                 735
        Ala His Leu Pro Leu Ala Lys Thr Val Ser Val Glu Glu Leu Leu Gln
                        740                 745                 750
        Tyr Val Glu Leu Gln Asp Pro Val Thr Arg Thr Gln Leu Arg Ala Met
                        755                 760                 765
        Ala Ala Lys Thr Val Cys Pro Pro His Lys Val Glu Leu Glu Ala Leu
                        770                 775                 780
        Leu Glu Lys Gln Ala Tyr Lys Glu Gln Val Leu Ala Lys Arg Leu Thr
        785                 790                 795                 800
        Met Leu Glu Leu Leu Glu Lys Tyr Pro Ala Cys Glu Met Lys Phe Ser
                        805                 810                 815
```

```
Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
                850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
                930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
                995                 1000                1005

Ala Val Glu Ala Thr Leu Met Lys Ser Tyr Ala Asp Val His Gln
                1010                1015                1020

Val Ser Glu Ala Asp Ala Arg Leu Trp Leu Gln Gln Leu Glu Glu
                1025                1030                1035

Lys Gly Arg Tyr Ala Lys Asp Val Trp Ala Gly
                1040                1045

<210> SEQ ID NO 11
<211> LENGTH: 1049
<212> TYPE: PRT
<213> ORGANISM: Artificial Sequence
<220> FEATURE:
<223> OTHER INFORMATION: Synthetic sequence

<400> SEQUENCE: 11

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
                20                  25                  30

Ile Ala Asp Glu Leu Gly Glu Ile Phe Lys Phe Glu Ala Pro Gly Arg
                35                  40                  45

Val Thr Arg Tyr Leu Ser Ser Gln Arg Leu Ile Lys Glu Ala Cys Asp
                50                  55                  60

Glu Ser Arg Phe Asp Lys Asn Leu Ser Gln Ala Leu Lys Phe Asn Arg
65                  70                  75                  80

Asp Phe Thr Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Val
                115                 120                 125
```

```
Gln Lys Trp Glu Arg Leu Asn Ala Asp Glu His Ile Glu Val Ser Glu
    130                 135                 140
Asp Met Thr Arg Leu Thr Leu Asp Thr Ile Gly Leu Cys Gly Phe Asn
145                 150                 155                 160
Tyr Arg Phe Asn Ser Phe Tyr Arg Asp Gln Pro His Pro Phe Ile Ile
                165                 170                 175
Ser Met Val Arg Thr Phe Asp Glu Thr Met Asn Lys Leu Gln Arg Ala
                180                 185                 190
Asn Pro Asp Asp Pro Val Tyr Asp Glu Asn Lys Arg Gln Cys Gln Glu
            195                 200                 205
Asp Ile Lys Val Met Asn Asp Leu Val Asp Lys Ile Ile Ala Asp Arg
    210                 215                 220
Lys Ala Arg Gly Glu Gln Ser Asp Asp Leu Leu Thr Gln Met Leu Asn
225                 230                 235                 240
Gly Lys Asp Pro Glu Thr Gly Glu Pro Leu Asp Asp Gly Asn Ile Ser
                245                 250                 255
Tyr Gln Ile Ile Thr Phe Leu Ile Ala Gly His Glu Thr Thr Ser Gly
                260                 265                 270
Leu Leu Ser Phe Ala Leu Tyr Phe Leu Val Lys Asn Pro His Val Leu
            275                 280                 285
Gln Lys Val Ala Glu Glu Ala Ala Arg Val Leu Val Asp Pro Val Pro
    290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
                340                 345                 350
Glu Val Met Val Leu Ile Pro Gln Leu His Arg Asp Lys Thr Ile Trp
            355                 360                 365
Gly Asp Asp Val Glu Glu Phe Arg Pro Glu Arg Phe Glu Asn Pro Ser
    370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
                420                 425                 430
Asp Ile Lys Glu Thr Leu Thr Leu Lys Pro Glu Gly Phe Val Val Lys
            435                 440                 445
Ala Lys Ser Lys Lys Ile Pro Leu Gly Gly Ile Pro Ser Pro Ser Thr
    450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
                500                 505                 510
Gln Val Ala Thr Leu Asp Ser His Ala Gly Asn Leu Pro Arg Glu Gly
            515                 520                 525
Ala Val Leu Ile Val Thr Ala Ser Tyr Asn Gly His Pro Pro Asp Asn
    530                 535                 540
```

-continued

| | | | | | | | | | | | |
|---|---|---|---|---|---|---|---|---|---|---|---|
|Ala|Lys|Gln|Phe|Val|Asp|Trp|Leu|Asp|Gln|Ala|Ser|Ala|Asp|Glu|Val|
|545| | | | |550| | | |555| | | | |560| |

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val

```
                        965                 970                 975
Gln His Val Met Glu Gln Asp Gly Lys Lys Leu Ile Glu Leu Leu Asp
                980                 985                 990

Gln Gly Ala His Phe Tyr Ile Cys  Gly Asp Gly Ser Gln  Met Ala Pro
           995                 1000                1005

Ala Val  Glu Ala Thr Leu Met  Lys Ser Tyr Ala Asp  Val His Gln
    1010                1015                1020

Val Ser  Glu Ala Asp Ala Arg  Leu Trp Leu Gln Gln  Leu Glu Glu
    1025                1030                1035

Lys Gly  Arg Tyr Ala Lys Asp  Val Trp Ala Gly
    1040                1045

<210> SEQ ID NO 12
<211> LENGTH: 1049
<212> TYPE: PRT
<213> ORGANISM: Artificial Sequence
<220> FEATURE:
<223> OTHER INFORMATION: Synthetic sequence

<400> SEQUENCE: 12

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Phe Arg
65                  70                  75                  80

Asp Phe Ala Gly Asp Gly Leu Ala Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Thr Leu Asp Glu Val Met Asn Lys Leu Gln Arg Ala
            180                 185                 190

Asn Pro Asp Asp Pro Val Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
```

```
                  275                 280                 285
Gln Lys Val Ala Glu Ala Ala Arg Val Leu Val Asp Pro Val Pro
    290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Val Met Val Leu Ile Pro Gln Leu His Arg Asp Lys Thr Ile Trp
            355                 360                 365
Gly Asp Asp Val Glu Glu Phe Arg Pro Glu Arg Phe Glu Asn Pro Ser
    370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
            435                 440                 445
Ala Lys Ser Lys Lys Ile Pro Leu Gly Gly Ile Pro Ser Pro Ser Thr
    450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
            515                 520                 525
Ala Val Leu Ile Val Thr Ala Ser Tyr Asn Gly His Pro Pro Asp Asn
    530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
            595                 600                 605
Asp Phe Glu Gly Thr Tyr Glu Glu Trp Arg Glu His Met Trp Ser Asp
    610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
            660                 665                 670
Leu Gln Gln Pro Gly Ser Ala Arg Ser Thr Arg His Leu Glu Ile Glu
            675                 680                 685
Leu Pro Lys Glu Ala Ser Tyr Gln Glu Gly Asp His Leu Gly Val Ile
    690                 695                 700
```

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 13
<211> LENGTH: 1049
<212> TYPE: PRT
<213> ORGANISM: Artificial Sequence
<220> FEATURE:
<223> OTHER INFORMATION: Synthetic sequence

<400> SEQUENCE: 13

Met Thr Ile Lys Glu Met Pro Gln Pro Lys Thr Phe Gly Glu Leu Lys
1               5                   10                  15

```
Asn Leu Pro Leu Leu Asn Thr Asp Lys Pro Val Gln Ala Leu Met Lys
             20                  25                  30

Ile Ala Asp Glu Leu Gly Glu Ile Phe Lys Phe Ala Pro Gly Arg
         35                  40                  45

Val Thr Arg Tyr Leu Ser Ser Gln Arg Leu Ile Lys Glu Ala Cys Asp
     50                  55                  60

Glu Ser Arg Phe Asp Lys Asn Leu Ser Gln Ala Leu Lys Phe Asn Arg
 65                  70                  75                  80

Asp Phe Ala Gly Asp Gly Leu Ala Thr Ser Trp Thr His Glu Lys Asn
                 85                  90                  95

Trp Lys Lys Ala His Asn Ile Leu Leu Pro Ser Phe Ser Gln Gln Ala
             100                 105                 110

Met Lys Gly Tyr His Ala Met Met Val Asp Ile Ala Val Gln Leu Val
             115                 120                 125

Gln Lys Trp Glu Arg Leu Asn Ala Asp Glu His Ile Glu Val Ser Glu
 130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                 165                 170                 175

Ser Met Val Arg Thr Leu Asp Glu Val Met Asn Lys Leu Gln Arg Ala
             180                 185                 190

Asn Pro Asp Asp Pro Val Tyr Asp Glu Asn Lys Arg Gln Cys Gln Glu
             195                 200                 205

Asp Ile Lys Val Met Asn Asp Leu Val Asp Lys Ile Ile Ala Asp Arg
 210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                 245                 250                 255

Tyr Gln Ile Ile Thr Phe Leu Ile Ala Gly His Glu Thr Thr Ser Gly
             260                 265                 270

Leu Leu Ser Phe Ala Leu Tyr Phe Leu Val Lys Asn Pro His Val Leu
             275                 280                 285

Gln Lys Val Ala Glu Glu Ala Ala Arg Val Leu Val Asp Pro Val Pro
 290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                 325                 330                 335

Lys Glu Asp Thr Val Leu Gly Gly Glu Tyr Pro Leu Glu Lys Gly Asp
             340                 345                 350

Glu Val Met Val Leu Ile Pro Gln Leu His Arg Asp Lys Thr Ile Trp
             355                 360                 365

Gly Asp Asp Val Glu Glu Phe Arg Pro Glu Arg Phe Glu Asn Pro Ser
 370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                 405                 410                 415

Met Met Leu Lys His Phe Asp Phe Glu Asp His Thr Asn Tyr Glu Leu
             420                 425                 430
```

```
Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
```

```
                    850                 855                 860
Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                    885                 890                 895

Thr Pro Leu Ile Met Val Gly Pro Thr Gly Val Ala Pro Phe Arg
                900                 905                 910

Gly Phe Val Gln Ala Arg Lys Gln Leu Lys Glu Gln Gly Gln Ser Leu
                    915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
   1010                1015                1020

Val Ser Glu Ala Asp Ala Arg Leu Trp Leu Gln Gln Leu Glu Glu
   1025                1030                1035

Lys Gly Arg Tyr Ala Lys Asp Val Trp Ala Gly
   1040                1045

<210> SEQ ID NO 14
<211> LENGTH: 1049
<212> TYPE: PRT
<213> ORGANISM: Artificial Sequence
<220> FEATURE:
<223> OTHER INFORMATION: Synthetic sequence

<400> SEQUENCE: 14

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Val Leu Lys Phe Asn Arg
65                  70                  75                  80

Asp Phe Ala Gly Asp Gly Leu Ala Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
```

```
            165                 170                 175
Ser Met Val Arg Thr Ala Asp Glu Thr Met Asn Lys Leu Gln Arg Ala
                180                 185                 190

Asn Pro Asp Asp Pro Val Tyr Asp Glu Asn Lys Arg Gln Cys Gln Glu
            195                 200             205

Asp Ile Lys Val Met Asn Asp Leu Val Asp Lys Ile Ile Ala Asp Arg
        210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
            275                 280                 285

Gln Lys Val Ala Glu Ala Ala Arg Val Leu Val Asp Pro Val Pro
            290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Val Met Val Leu Ile Pro Gln Leu His Arg Asp Lys Thr Ile Trp
                355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
            530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590
```

```
Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
        770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
        850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
        930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005
```

-continued

```
Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 15
<211> LENGTH: 1049
<212> TYPE: PRT
<213> ORGANISM: Artificial Sequence
<220> FEATURE:
<223> OTHER INFORMATION: Synthetic sequence

<400> SEQUENCE: 15

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Thr Leu Lys Phe Asn Arg
65                  70                  75                  80

Asp Phe Ala Gly Asp Gly Leu Ala Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Ser Met Asn Lys Leu Gln Arg Ala
            180                 185                 190

Asn Pro Asp Asp Pro Val Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320
```

-continued

```
Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
```

```
                    740                 745                 750
Tyr Val Glu Leu Gln Asp Pro Val Thr Arg Thr Gln Leu Arg Ala Met
                755                 760                 765
Ala Ala Lys Thr Val Cys Pro His Lys Val Leu Glu Ala Leu
            770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
                820                 825                 830
Ser Ser Ser Pro Arg Val Asp Glu Lys Gln Ala Ser Ile Thr Val Ser
                835                 840                 845
Val Val Ser Gly Glu Ala Trp Ser Gly Tyr Gly Glu Tyr Lys Gly Ile
                850                 855                 860
Ala Ser Asn Tyr Leu Ala Glu Leu Gln Glu Gly Asp Thr Ile Thr Cys
865                 870                 875                 880
Phe Ile Ser Thr Pro Gln Ser Glu Phe Thr Leu Pro Lys Asp Pro Glu
                885                 890                 895
Thr Pro Leu Ile Met Val Gly Pro Gly Thr Gly Val Ala Pro Phe Arg
                900                 905                 910
Gly Phe Val Gln Ala Arg Lys Gln Leu Lys Glu Gln Gly Gln Ser Leu
                915                 920                 925
Gly Glu Ala His Leu Tyr Phe Gly Cys Arg Ser Pro His Glu Asp Tyr
                930                 935                 940
Leu Tyr Gln Glu Glu Leu Glu Asn Ala Gln Ser Glu Gly Ile Ile Thr
945                 950                 955                 960
Leu His Thr Ala Phe Ser Arg Met Pro Asn Gln Pro Lys Thr Tyr Val
                965                 970                 975
Gln His Val Met Glu Gln Asp Gly Lys Lys Leu Ile Glu Leu Leu Asp
                980                 985                 990
Gln Gly Ala His Phe Tyr Ile Cys Gly Asp Gly Ser Gln Met Ala Pro
                995                 1000                1005
Ala Val Glu Ala Thr Leu Met Lys Ser Tyr Ala Asp Val His Gln
            1010                1015                1020
Val Ser Glu Ala Asp Ala Arg Leu Trp Leu Gln Gln Leu Glu Glu
            1025                1030                1035
Lys Gly Arg Tyr Ala Lys Asp Val Trp Ala Gly
            1040                1045

<210> SEQ ID NO 16
<211> LENGTH: 21
<212> TYPE: DNA
<213> ORGANISM: Artificial Sequence
<220> FEATURE:
<223> OTHER INFORMATION: Engineered sequence

<400> SEQUENCE: 16
ggaaacagga tccatcgatg c                                              21

<210> SEQ ID NO 17
```

```
<211> LENGTH: 27
<212> TYPE: DNA
<213> ORGANISM: Artificial Sequence
<220> FEATURE:
<223> OTHER INFORMATION: Engineered sequence

<400> SEQUENCE: 17
aatatcgagc tcgtagtttg tatgatc                                          27
```

ARTEMISININ DERIVATIVES, METHODS FOR THEIR PREPARATION AND THEIR USE AS ANTIMALARIAL AGENTS

CROSS-REFERENCE TO RELATED APPLICATIONS

This application is a national stage application under 35 U.S.C. §371 of PCT Application No. PCT/US2013/067118, filed Oct. 28, 2013, which claims priority to and the benefit of U.S. provisional patent application Ser. No. 61/719,758, entitled Artemisinin Derivatives, Methods for Their Preparation and Their Use as Antimalarial Agents, filed Oct. 29, 2012, which is incorporated herein by reference in its entirety.

STATEMENT REGARDING FEDERALLY SPONSORED RESEARCH OR DEVELOPMENT

This invention was made with government support under contract no. GM098628 awarded by the National Institutes of Health. The government has certain rights in the invention.

1. TECHNICAL FIELD

The present invention relates to derivatives of the antimalarial agent artemisinin. The invention also relates to methods and compositions for preparation of artemisinin derivatives. The invention also relates to pharmaceutical compositions for treating parasitic infections. The invention also relates to methods for using artemisinin derivatives to treat parasitic infections. The invention also relates to methods for producing artemisinin derivatives via functionalization of positions C7 and C6a, optionally in conjunction with modifications at positions C10 and C9, via chemoenzymatic methods.

2. BACKGROUND OF THE INVENTION

Malaria continues to represent a devastating world-wide health problem. Each year, an estimated 500 million people contract malaria, resulting in over 1 million deaths annually (Snow, Guerra et al. 2005). In humans, malaria is caused by the infection with obligate intraerythrocytic protozoa of the genus *Plasmodium*, and specifically by the infection with one (or more) of the following four species: *P. falciparum, P. vivax, P. ovale*, and *P. malariae*. Among these, *P. falciparum* is responsible for the vast majority of lethal malaria infections. Traditional pharmacological treatments against malaria have involved the use of quinolines (e.g., chloroquine, quinine, mefloquine, primaquine) and antifolates (e.g., sulfadoxine-pyrimethamine) Unfortunately, parasite resistance against one or more of these drugs has emerged in many endemic countries over the past decades, causing a steep resurgence of malaria morbidity and mortality (Eastman and Fidock 2009).

Currently, a most promising class of antimalarial agents is that derived from the naturally occurring sesquiterpene lactone artemisinin (ART, 1), also known as Qinghaosu (Eastman and Fidock 2009).

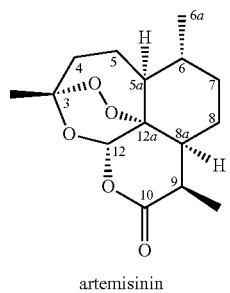

artemisinin (1)

Artemisinin is extracted from the annual wormwood *Artemisia annua* and its antimalarial properties were first discovered by Chinese scientists in the early 1970s (White 2008). Artemisinin was found to be highly effective at suppressing the parasitemias caused by *P. falciparum* and *P. vivax*, including those caused by multidrug-resistant *Plasmodium* strains insensitive to conventional antimalarial drugs such as chloroquine and sulfadoxine-pyrimethamine. In addition, artemisinin exhibits several other advantageous features as antimalarial agent such as rapid onset of action, high therapeutic index, and high activity against all of the blood stages of parasite infection, inducing 10- to 100-fold higher reduction in parasitemia per cycle compared to other antimalarial agents (White 2008). It is also active against *P. falciparum* gametocytes, which are responsible for transmission of the infection and spread of the disease (Chen, Li et al. 1994). Owing to these properties, artemisinin-based therapies constitute a mainstay of the current portfolio of antimalarial drugs and they have been recommended by WHO as first-line treatment for both uncomplicated and severe malaria (Olliaro and Wells 2009).

Current artemisinin-based therapies rely on the semisynthetic, C10-modified artemisinin derivatives artemether (ATM), artesunate (AS), or dehydroartemisinin (DHA), which have improved oral bioavailability and/or water-solubility compared to artemisinin. These derivatives are prepared via chemical reduction of the lactone ring in artemisinin to yield DHA, which can be further transformed into artemether or artesunate via etherification or esterification of the C10 hydroxyl group, respectively.

Despite their viability as antimalarial agents, an important drawback of these semisynthetic artemisinin derivatives is a very short half-life in plasma and in the human body (<1-2 hours) (Navaratnam, Mansor et al. 2000). As a result of this limited metabolic stability, high and repeated doses of these compounds are typically required for a single course of treatment, which contributes to the high costs of ART-based combination therapies (ACTs) and, in turn, to their limited economic accessibility in malaria endemic countries (White 2008). The development of more potent and/or metabolically stable artemisinin derivatives would permit the use of lower and/or less frequent therapeutic dosages, thus providing key advantages compared to currently available artemisinin-based drugs.

In humans, a major route of artemether/artesunate metabolic breakdown involves the rapid conversion of these drugs to DHA via dealkylation or hydrolysis, respectively, of the ether/ester group at C10 (Navaratnam, Mansor et al. 2000; O'Neill and Posner 2004). In addition, these drugs are metabolized by hepatic P450s, resulting in oxidized products carrying hydroxylation(s) at position C7 and C6a (Navaratnam, Mansor et al. 2000; O'Neill and Posner 2004;

Haynes, Fugmann et al. 2006). Both these hydroxylated metabolites and DHA are targets of Phase II metabolism (glucuronidation), which further contributes to the fast clearance and excretion of these metabolites (Navaratnam, Mansor et al. 2000; O'Neill and Posner 2004).

In principle, chemical manipulation of metabolically labile positions in the artemisinin structure could provide a means to produce derivatives with improved pharmacokinetic properties and in vivo activity. Yet, the structural complexity of artemisinin, including the presence of a potentially reactive endoperoxide bridge which is essential for antiplasmodial activity, severely limits the range of chemical transformations accessible on this compound.

In part due to these constraints, the vast majority of medicinal chemistry studies carried out on this natural product over the past two decades have focused on modifying position C10 and/or the neighboring site C9, which can be accessed by chemical means. Accordingly, the synthesis and biological evaluation of a large number of C10- and C9-substituted derivatives of artemisinin have been reported (O'Neill and Posner 2004; Chaturvedi, Goswami et al. 2010). Further derivatives of this type and methods for their preparation are described in Venugopalan et al., U.S. Pat. No. 5,225,427 (1993); McChesney et al., U.S. Pat. No. 5,225,562 (1993); Posner et al., U.S. Pat. No. 6,156,790 (2000); Li et al., U.S. Pat. No. 6,307,068 (2001); Posner et al., U.S. Pat. No. 6,586,464 (2003); Begue et al. U.S. Pat. No. 7,417,155 (2008); Posner et al., U.S. Pat. No. 7,417,156 (2008); Begue et al., U.S. Pat. No. 7,696,362 (2010); Haynes et al., U.S. Pat. No. 7,439,238 (2008); Li et al., U.S. Pat. No. 7,910,750 (2011). In some cases, the substitution of the labile C10 ether/ester linkage (as in artemether and artesunate) with non-hydrolizable bonds such as carbon-carbon or carbon-nitrogen bonds has led to artemisinin derivatives with improved antimalarial properties (O'Neill and Posner 2004; Chaturvedi, Goswami et al. 2010). For example, a most promising candidate among the 10-functionalized artemisinin derivatives is the 10-alkylamino derivative artemisone (Haynes, Fugmann et al. 2006). However, C10- (or C9-) substituted artemisinin derivatives remain susceptible to metabolic attack by human liver P450s at the level of the carbocyclic core of the molecule, (Haynes, Fugmann et al. 2006) which can result in somewhat prolonged but still very short in vivo elimination half-lives as observed in the case of artemisone (Nagelschmitz, Voith et al. 2008)

Citation or identification of any reference in Section 2, or in any other section of this application, shall not be considered an admission that such reference is available as prior art to the present invention.

3. SUMMARY OF THE INVENTION

Provided herein are derivatives of the antimalarial agent artemisinin, methods and compositions for preparation of the derivatives, and methods for using the pharmaceutical compositions for the treatment of parasitic infections.

Uses for pharmaceutical compositions as intended for the treatment of parasitic infections are also provided.

Methods are also provided for the production of artemisinin derivatives via functionalization of positions C7 and C6a, and optionally, in some embodiments, in conjunction with modifications at positions C10 and C9, via chemoenzymatic methods.

Methods are also provided for chemically manipulating metabolically labile positions in artemisinin carbocyclic scaffold, such as positions C7 and C6a, which constitute primary targets of human liver P450-mediated metabolism.

Also provided are methods for the generation of artemisinin derivatives functionalized at positions C7 and C6a. The inventor has discovered that engineered variants of non-human cytochrome P450 enzymes can be used for the hydroxylation of these unactivated, aliphatic sites in artemisinin and derivatives thereof.

In one embodiment, these P450-catalyzed C—H hydroxylation reactions can be coupled to chemical transformations of hydroxyl group interconversion in order to install a broad range of desired functionalities at these relevant yet unreactive sites of the molecule.

In another embodiment, these enzymatic transformations can be carried out using artemisinin as well as semisynthetic artemisinin derivatives, such as 10- or 9-substituted artemisinin derivatives, as substrates.

In another embodiment, methods are provided for producing polyfunctionalized artemisinin derivatives that carry multiple substitutions such as, for example, at a position within the carbocyclic backbone of the molecule (i.e., C7 or C6a) and at a position within the lactone ring (e.g., C10 and/or C9).

A recombinant cytochrome P450 polypeptide is provided having an improved capability as compared to a P450 enzyme of SEQ ID NO. 1, SEQ ID NO. 2 or SEQ ID NO. 3, to hydroxylate at least one substrate from the group consisting of substrates of general formula (I),

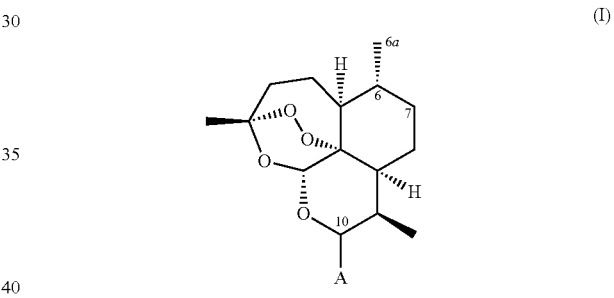

(I)

wherein:
(i) A represents a carbonyl group (═O), a hydroxy group (—OH), a halogen atom, an unsubstituted or substituted alkyloxy group, an unsubstituted or substituted alkenyloxy group, an unsubstituted or substituted alkynyloxy group, an unsubstituted or substituted aryloxy group, an unsubstituted or substituted heteroaryloxy group, or a group —NR$_1$R$_2$, wherein:
the R$_1$ represents a hydrogen atom, an unsubstituted or substituted alkyl group, an unsubstituted or substituted alkenyl group, or an unsubstituted or substituted alkynyl group;
the R$_2$ represents an unsubstituted or substituted alkyl group, an unsubstituted or substituted alkenyl group, an unsubstituted or substituted alkynyl group, an unsubstituted or substituted aryl group, an unsubstituted or substituted heteroaryl group; or
the R$_1$ and R$_2$ are connected together to form an unsubstituted or substituted heterocyclic group;
and wherein the cytochrome P450 polypeptide comprises an amino acid sequence that is at least 60% identical to SEQ ID NO. 1, SEQ ID NO. 2 or SEQ ID NO. 3.

In one embodiment, the recombinant cytochrome P450 polypeptide comprises an amino acid sequence that is at least 90% identical to SEQ ID NO. 1 and comprises an amino acid substitution at a position selected from the group consisting of position X26, X27, X43, X48, X52, X73, X75, X76, X79, X82, X83, X88, X143, X176, X181, X182, X185, X189, X198, X206, X227, X237, X253, X256, X261, X264, X265, X268, X269, X291, X329, X330, X354, X355, X438, and X439 of SEQ ID NO. 1.

In another embodiment, the recombinant cytochrome P450 polypeptide comprises an amino acid sequence that is at least 90% identical to SEQ ID NO. 2 and comprises an amino acid substitution at a position selected from the group consisting of position X28, X29, X45, X50, X54, X75, X77, X78, X81, X83, X85, X90, X145, X178, X183, X184, X187, X191, X208, X229, X239, X255, X256, X263, X266, X267, X270, X271, X293, X331, X332, X356, X357, and X440 of SEQ ID NO. 2.

In another embodiment, the recombinant cytochrome P450 polypeptide comprises an amino acid sequence that is at least 90% identical to SEQ ID NO. 3 and comprises an amino acid substitution at a position selected from the group consisting of position X29, X30, X46, X51, X55, X76, X78, X79, X82, X84, X86, X91, X146, X179, X184, X185, X188, X192, X198, X209, X230, X240, X256, X257, X264, X267, X268, X271, X272, X294, X332, X333, X364, X365, and X448 of SEQ ID NO. 3.

In one embodiment, the improved capability of the recombinant cytochrome P450 polypeptide is an improved capability to hydroxylate position 6a, position 7, or both of these positions in the substrate.

In another embodiment, the improved capability of the recombinant cytochrome P450 polypeptide in hydroxylating position 6a in the substrate is an increase in total turnover numbers supported by the enzyme for the oxidation of the substrate, or an increase in the regioselectivity of the enzyme-catalyzed reaction toward 6a-hydroxylation, or both.

In another embodiment, the improved capability of the recombinant cytochrome P450 polypeptide in hydroxylating position 7 in the substrate is an increase in total turnover numbers supported by the enzyme for the oxidation of the substrate, or an increase in the regioselectivity of the enzyme-catalyzed reaction toward 7-hydroxylation, or an increase in the stereoselectivity of the enzyme-catalyzed reaction toward 7-hydroxylation, or by a combination of the afore-mentioned properties.

In another embodiment of the recombinant cytochrome P450 polypeptide, the substrate is artemisinin, dihydroartemisinin, artemether, artesunate methyl ester, or 10-trimethylsylylether-artemisinin In another embodiment, the recombinant polypeptide has an amino acid sequence that is at least 60%, 70%, 80%, 85%, 90%, 95%, 99% or more identical to a sequence corresponding to SEQ ID NO.: 4, 5, 6, 7, 8, 9, 10, 11, 12, 13, 14, or 15.

In another embodiment, the recombinant cytochrome P450 polypeptide is selected from the group consisting of SEQ ID NOS.: 4, 5, 6, 7, 8, 9, 10, 11, 12, 13, 14, and 15.

In another embodiment, the recombinant cytochrome P450 polypeptide comprises a polypeptide that is at least 60% identical to the amino acid sequence SEQ ID NO.: 1 and comprises at least one of the features selected from the group consisting of: X48 is C or R; X75 is A, V, or T; X79 is A, S, N, V, or F; X82 is S, V, I, or F; X83 is L, V, A, or T; X88 is A, L, I, or F; X143 is S or P; X176 is I or T; X181 is T or A; X182 is L, F, or A; X185 is A, V, T, or S; X189 is A or L; X198 is V or A; X206 is C or F; X227 is R or S; X237 is Q or H; X253 is G or E; X256 is S or R; X291 is V or A; X329 is V or A; and X354 is V or L.

In another embodiment, the recombinant cytochrome P450 polypeptide comprises an amino acid sequence comprising a cytochrome P450 heme domain that is at least 60% identical to the amino acid sequence from X1 to X500 in SEQ ID NO.: 1, 2, 3, 4, 5, 6, 7, 8, 9, 10, 11, 12, 13, 14, or 15.

A method is provided for hydroxylating a substrate of general formula (I),

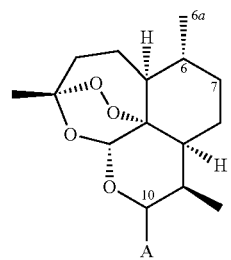

comprising the steps of:
a. contacting the substrate with the recombinant cytochrome P450 polypeptide under suitable reaction conditions;
b. allowing for the recombinant cytochrome P450 polypeptide to catalyze the hydroxylation of said substrate, while preserving the endoperoxide bond therein, thereby producing a hydroxylated derivative of said substrate; and
c. isolating said hydroxylated derivative of said substrate.

In one embodiment, the method additionally comprises the step of providing the recombinant cytochrome P450 polypeptide.

In another embodiment of the method, the recombinant cytochrome P450 polypeptide comprises an amino acid sequence that is at least 90% identical to SEQ ID NO. 1 and wherein the polypeptide comprises an amino acid substitution at a position selected from the group consisting of position X26, X27, X43, X48, X52, X73, X75, X76, X79, X82, X83, X88, X143, X176, X181, X182, X185, X189, X198, X206, X227, X237, X253, X256, X261, X264, X265, X268, X269, X291, X329, X330, X354, X355, X438, and X439 of SEQ ID NO. 1.

In another embodiment of the method, the recombinant cytochrome P450 polypeptide comprises an amino acid sequence that is at least 90% identical to SEQ ID NO. 2 and comprises an amino acid substitution at a position selected from the group consisting of position X28, X29, X45, X50, X54, X75, X77, X78, X81, X83, X85, X90, X145, X178, X183, X184, X187, X191, X208, X229, X239, X255, X256, X263, X266, X267, X270, X271, X293, X331, X332, X356, X357, and X440 of SEQ ID NO. 2.

In another embodiment of the method, the recombinant cytochrome P450 polypeptide comprises an amino acid sequence that is at least 90% identical to SEQ ID NO. 3 and comprises an amino acid substitution at a position selected from the group consisting of position X29, X30, X46, X51, X55, X76, X78, X79, X82, X84, X86, X91, X146, X179, X184, X185, X188, X192, X198, X209, X230, X240, X256, X257, X264, X267, X268, X271, X272, X294, X332, X333, X364, X365, and X448 of SEQ ID NO. 3.

In another embodiment of the method, the recombinant cytochrome P450 polypeptide comprises a polypeptide that is at least 60% identical to the amino acid sequence SEQ ID NO.: 1 and comprises one or more of the features selected from the group consisting of: X48 is C or R; X75 is A, V, or T; X79 is A, S, N, V, or F; X82 is S, V, I, or F; X83 is L, V, A, or T; X88 is A, L, I, or F; X143 is S or P; X176 is I or T; X181 is T or A; X182 is L, F, or A; X185 is A, V, T, or S; X189 is A or L; X198 is V or A; X206 is C or F; X227 is R or S; X237 is Q or H; X253 is G or E; X256 is S or R; X291 is V or A; X329 is V or A; and X354 is V or L In another embodiment of the method, the recombinant cytochrome P450 polypeptide comprises an amino acid sequence that is at least 90% identical to SEQ ID NO. 3 and comprises an amino acid substitution at a position selected from the group consisting of position X29, X30, X46, X51, X55, X76, X78, X79, X82, X84, X86, X91, X146, X179, X184, X185, X188, X192, X198, X209, X230, X240, X256, X257, X264, X267, X268, X271, X272, X294, X332, X333, X364, X365, and X448 of SEQ ID NO. 3.

In another embodiment of the method, the recombinant cytochrome P450 polypeptide comprises (or consists of) an amino acid sequence selected from the group consisting of SEQ ID NO.: 4, 5, 6, 7, 8, 9, 10, 11, 12, 13, 14, and 15.

In another embodiment, the recombinant cytochrome P450 polypeptide has an amino acid sequence that is at least 60%, 70%, 80%, 85%, 90%, 95%, 99% or more identical to a sequence corresponding to SEQ ID NO.: 4, 5, 6, 7, 8, 9, 10, 11, 12, 13, 14, or 15.

In another embodiment of the method, the substrate is artemisinin and the hydroxylated products comprise one or more compounds selected from the group consisting of 6a-hydroxyartemisinin, 7(S)-hydroxyartemisinin, and 7(R)-hydroxyartemisinin In another embodiment of the method, the substrate is selected from the group consisting of dihydroartemisinin, artemether, artesunate methyl ester, and 10-trimethylsylyle-ther-artemisinin.

In another embodiment of the method, the recombinant cytochrome P450 polypeptide is tethered to a solid support.

In another embodiment of the method, the solid support is a bead, a microsphere, a particle, a surface, a membrane, a matrix, or a hydrogel.

In another embodiment of the method, the recombinant cytochrome P450 polypeptide is contained in a host cell.

In another embodiment of the method, the host cell is a bacterial cell, a yeast cell, or a plant cell.

A compound is provided of general formula (II), (III), (IV), (V), or (VI), or a salt of a compound of general formula (II), (III), (IV), (V), or (VI)

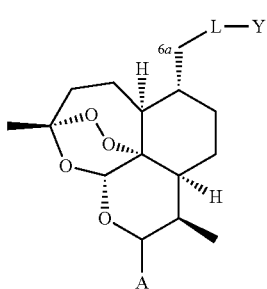
(II)

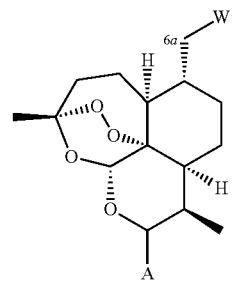
(III)

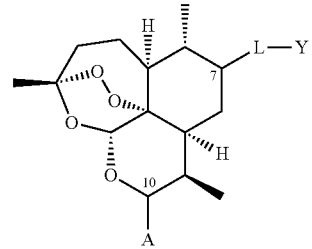
(IV)

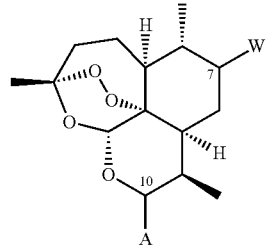
(V)

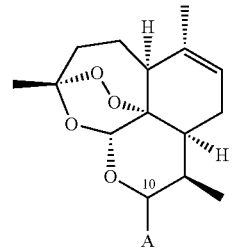
(VI)

wherein:
i. A represents a carbonyl group (═O), a hydroxy group (—OH), a halogen atom, an unsubstituted or substituted alkyloxy group, an unsubstituted or substituted alkenyloxy group, an unsubstituted or substituted alkynyloxy group, an unsubstituted or substituted aryloxy group, an unsubstituted or substituted heteroaryloxy group, or a group —NR$_1$R$_2$, where:
the R$_1$ represents a hydrogen atom, an unsubstituted or substituted substituted alkyl group, an unsubstituted or substituted alkenyl group, an unsubstituted or substituted alkynyl group,
the R$_2$ represents an unsubstituted or substituted alkyl group, an unsubstituted or substituted alkenyl group, an unsubstituted or substituted alkynyl group, an unsubstituted or substituted aryl group, or an unsubstituted or substituted heteroaryl group, or
the R$_1$ and the R$_2$ are connected together to form, with the nitrogen atom, an unsubstituted or substituted 5-12 membered ring, said ring optionally comprising one or more heteroatoms or group selected from —CO—, —SO—, —SO$_2$—, and —PO— group;

ii. L represents —O—, —OCH$_2$—, —NH—, —OC(O)—, —NHC(O)—, —S—, —SO—, —SO$_2$—, —PO—, or a chemical bond connecting the carbon atom to Y;

iii. Y represents a hydrogen atom, an unsubstituted or substituted alkyl group, an unsubstituted or substituted alkenyl group, an unsubstituted or substituted alkynyl group, an unsubstituted or substituted heteroalkyl group, an unsubstituted or substituted heteroalkenyl group, an unsubstituted or substituted heteroalkynyl group, an unsubstituted or substituted aryl group, an unsubstituted or substituted heteroaryl group, or an unsubstituted or substituted heterocyclic group; and iv. W represents a halogen atom, a carbonyl group (═O), an azido group (—N$_3$), an unsubstituted or substituted substituted triazole group, or a group —NR$_1$R$_2$, where:

the R$_1$ represents a hydrogen atom or an unsubstituted or substituted alkyl group, an unsubstituted or substituted alkenyl group, an unsubstituted or substituted alkynyl group, the R$_2$ represents an unsubstituted or substituted alkyl group, an unsubstituted or substituted alkenyl group, an unsubstituted or substituted alkynyl group, an unsubstituted or substituted aryl group, or an unsubstituted or substituted heteroaryl group, or the R$_1$ and the R$_2$ are connected together to form, with the nitrogen atom, an unsubstituted or substituted 5-12 membered ring, said ring optionally comprising one or more heteroatoms or group selected from —CO—, —SO—, —SO$_2$—, and —PO— group.

In one embodiment of the compound, A represents a carbonyl group (═O), a hydroxyl group (—OH), a methoxy group (—OCH$_3$), an ethoxy group (—OCH$_2$CH$_3$), a thiomorpholine 1,1-dioxide group, or a group —OC(O)(CH$_2$)— COOH, with n being an integer number from 1 to 4.

In another embodiment of the compound, W represents —F, —Cl, —NH$_2$, —N$_3$, a substituted or unsubstituted triazolyl group, a substituted or unsubstituted alkyloxy, alkenyloxy, or alkynyloxy group, or a —NR$_1$R$_2$ or —NHC(O)R$_1$ group, where:

the R$_1$ represents a hydrogen atom or an unsubstituted or substituted alkyl group, an unsubstituted or substituted alkenyl group, an unsubstituted or substituted alkynyl group, the R$_2$ represents an unsubstituted or substituted alkyl group, an unsubstituted or substituted alkenyl group, an unsubstituted or substituted alkynyl group, an unsubstituted or substituted aryl group, or an unsubstituted or substituted heteroaryl group, or the R$_1$ and the R$_2$ are connected together to form, with the nitrogen atom, an unsubstituted or substituted 5-12 membered ring, said ring optionally comprising one or more heteroatoms or group selected from —CO—, —SO—, —SO$_2$—, and —PO— group.

In another embodiment of the compound, L is —OC(O)— and Y represents an unsubstituted or substituted aryl group or an unsubstituted or substituted heteroaryl group.

A pharmaceutical composition is provided comprising a therapeutically effective amount of the compound; and a pharmaceutically acceptable carrier.

A method is provided for treating a disease caused by infection with a parasite of the genus *Plasmodium*, the method comprising the step of:

administering to a host in need of such treatment a therapeutically effective amount of a compound of general formula (II), (III), (IV), (V), (VI), or a salt of a compound of general formula (II), (III), (IV), (V), (VI)

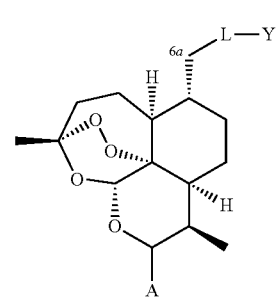

(II)

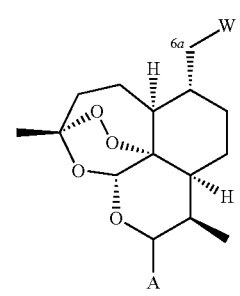

(III)

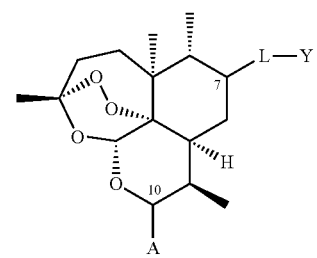

(IV)

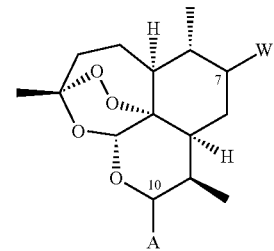

(V)

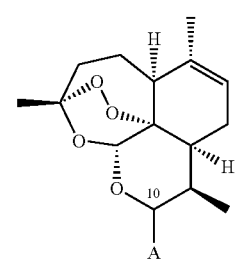

(VI)

wherein:

i. A represents a carbonyl group (═O), a hydroxy group (—OH), a halogen atom, an unsubstituted or substituted alkyloxy group, an unsubstituted or substituted alkenyloxy group, an unsubstituted or substituted alkynyloxy group, an unsubstituted or substituted aryloxy group, an unsubstituted or substituted heteroaryloxy group, or a group —NR$_1$R$_2$, where:

the R$_1$ represents a hydrogen atom, an unsubstituted or substituted substituted alkyl group, an unsubstituted or substituted alkenyl group, an unsubstituted or substituted alkynyl group, the $R_2$ represents an unsubstituted or substituted alkyl group, an unsubstituted or substituted alkenyl group, an unsubstituted or substituted alkynyl group, an unsubstituted or substituted aryl group, or an unsubstituted or substituted heteroaryl group, or the $R_1$ and the $R_2$ are connected together to form, with the nitrogen atom, an unsubstituted or substituted 5-12 membered ring, said ring optionally comprising one or more heteroatoms or group selected from —CO—, —SO—, —SO$_2$—, and —PO— group;

ii. L represents —O—, —OCH$_2$—, —NH—, —OC(O)—, —NHC(O)—, —S—, —SO—, —SO$_2$—, —PO—, or a chemical bond connecting the carbon atom to Y;

iii. Y represents a hydrogen atom, an unsubstituted or substituted alkyl group, an unsubstituted or substituted alkenyl group, an unsubstituted or substituted alkynyl group, an unsubstituted or substituted heteroalkyl group, an unsubstituted or substituted heteroalkenyl group, an unsubstituted or substituted heteroalkynyl group, an unsubstituted or substituted aryl group, an unsubstituted or substituted heteroaryl group, or an unsubstituted or substituted heterocyclic group; and iv. W represents a halogen atom, a carbonyl group (=O), an azido group (—N$_3$), an unsubstituted or substituted substituted triazole group, or a group —NR$_1$R$_2$, where:

the $R_1$ represents a hydrogen atom or an unsubstituted or substituted alkyl group, an unsubstituted or substituted alkenyl group, an unsubstituted or substituted alkynyl group, the $R_2$ represents an unsubstituted or substituted alkyl group, an unsubstituted or substituted alkenyl group, an unsubstituted or substituted alkynyl group, an unsubstituted or substituted aryl group, or an unsubstituted or substituted heteroaryl group, or the $R_1$ and the $R_2$ are connected together to form, with the nitrogen atom, an unsubstituted or substituted 5-12 membered ring, said ring optionally comprising one or more heteroatoms or group selected from —CO—, —SO—, —SO$_2$—, and —PO— group.

In one embodiment of the method, A represents a carbonyl group (=O), a hydroxyl group (—OH), a methoxy group (—OCH$_3$), an ethoxy group (—OCH$_2$CH$_3$), a thiomorpholine 1,1-dioxide group, or a group —OC(O)(CH$_2$)$_n$COOH, with n being an integer number from 1 to 4.

In another embodiment of the method, W represents —F, —Cl, —NH$_2$, —N$_3$, a substituted or unsubstituted triazolyl group, a substituted or unsubstituted alkyloxy, alkenyloxy, or alkynyloxy group, or a —NR$_1$R$_2$ or —NHC(O)R$_1$ group, where:

the $R_1$ represents a hydrogen atom or an unsubstituted or substituted alkyl group, an unsubstituted or substituted alkenyl group, an unsubstituted or substituted alkynyl group, the $R_2$ represents an unsubstituted or substituted alkyl group, an unsubstituted or substituted alkenyl group, an unsubstituted or substituted alkynyl group, an unsubstituted or substituted aryl group, or an unsubstituted or substituted heteroaryl group, or the $R_1$ and the $R_2$ are connected together to form, with the nitrogen atom, an unsubstituted or substituted 5-12 membered ring, said ring optionally comprising one or more heteroatoms or group selected from —CO—, —SO—, —SO$_2$—, and —PO— group.

In another embodiment of the method, L is —OC(O)— and Y represents an unsubstituted or substituted aryl group or an unsubstituted or substituted heteroaryl group.

A recombinant polynucleotide molecule is provided comprising a nucleotide sequence, wherein the nucleotide sequence encodes a recombinant cytochrome P450 polypeptide, and wherein the recombinant polypeptide has an amino acid sequence that is at least 60%, 70%, 80%, 85%, 90%, 95%, 99% or more identical to SEQ ID NO.: 1, 2, or 3.

In one embodiment of the recombinant polynucleotide molecule, the recombinant polypeptide has an amino acid sequence that is at least 60%, 70%, 80%, 85%, 90%, 95%, 99% or more identical to a sequence corresponding to SEQ ID NO.: 4, 5, 6, 7, 8, 9, 10, 11, 12, 13, 14, or 15. An expression vector comprising the recombinant polynucleotide molecule is also provided. An expression host system comprising the recombinant polynucleotide molecule is also provided.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated, enlarged, exploded, or incomplete to facilitate an understanding of the invention.

FIG. 1. Hydroxylation products formed by the oxidation reaction catalyzed by the engineered P450 variant FL#62 (SEQ ID NO: 8) using artemisinin as substrate.

Figure 2:
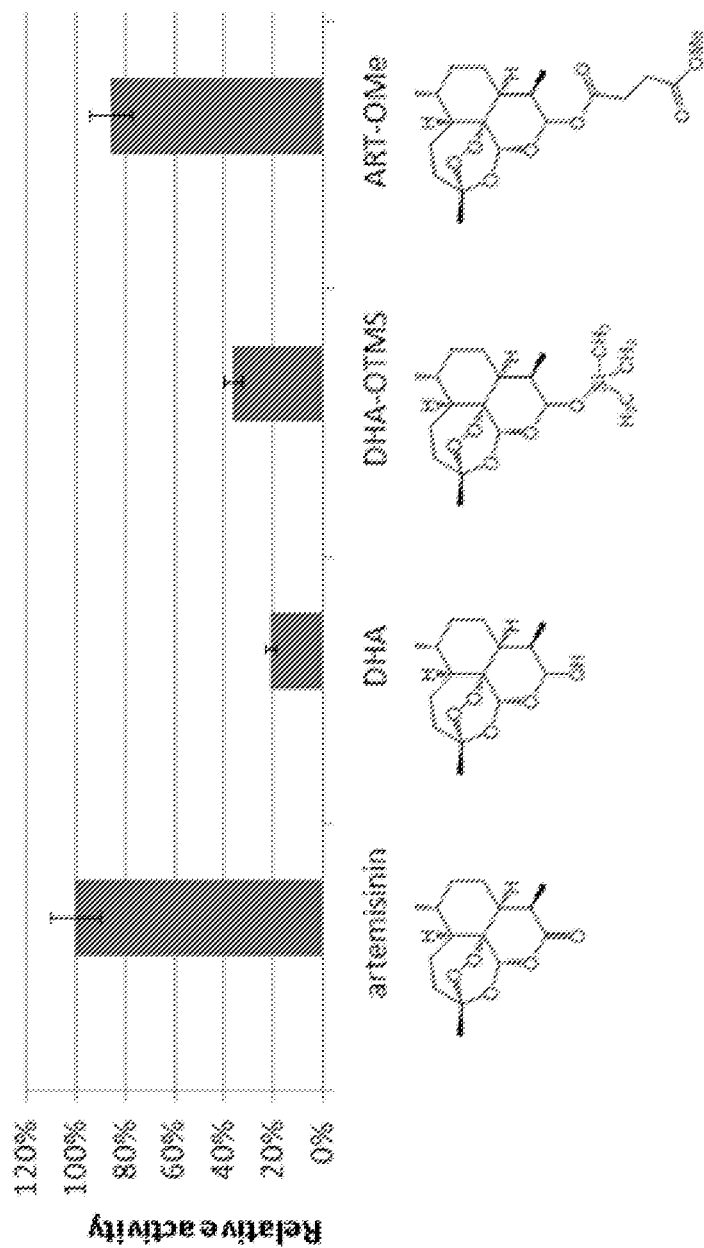

FIG. 2. Relative catalytic activity of the engineered P450 variant FL#62 (SEQ ID NO: 8) on different C10-substituted analogs of artemisinin FIG. 3. Chemoenzymatic transformation of artemisinin.

Figure 4:
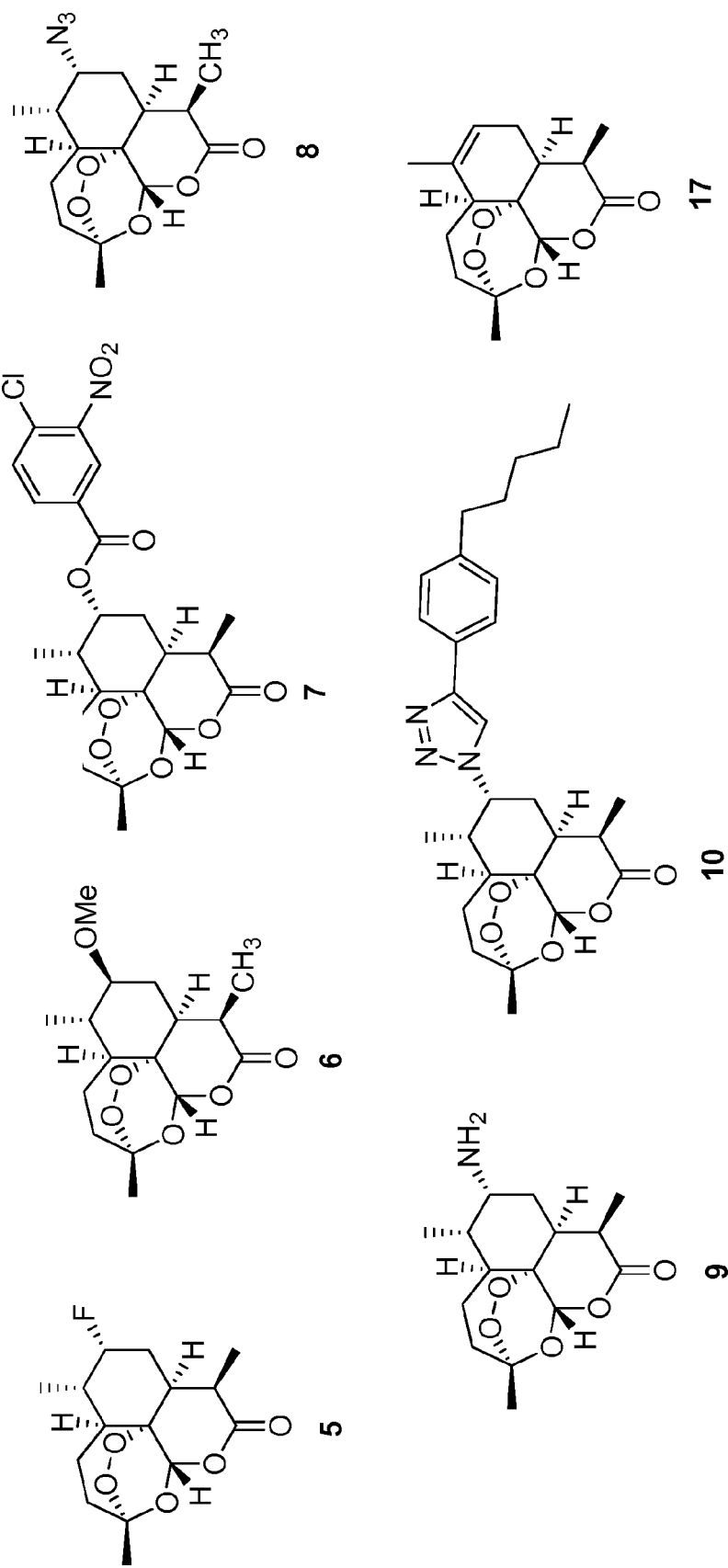

FIG. 4. Chemical structures of 7-substituted derivatives of artemisinin prepared according to one embodiment of the methods disclosed herein.

Figure 5:
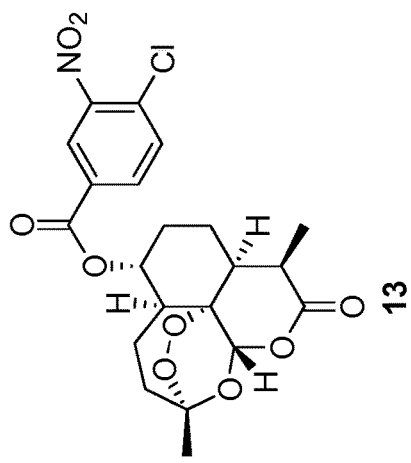
Figure 5:
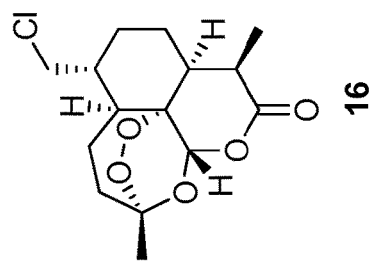
Figure 5:
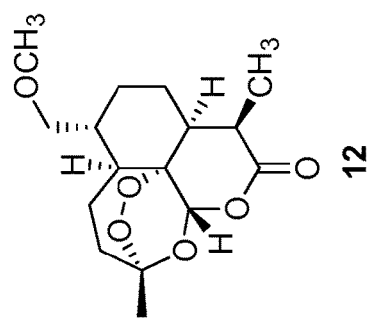
Figure 5:
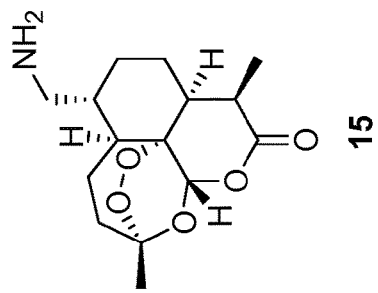
Figure 5:
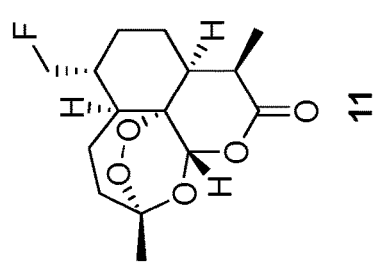
Figure 5:
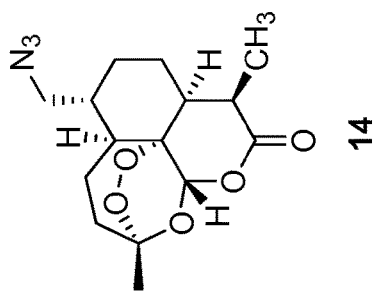

FIG. 5. Chemical structures of 6a-substituted derivatives of artemisinin prepared according to one embodiment of the methods disclosed herein.

Figure 6:
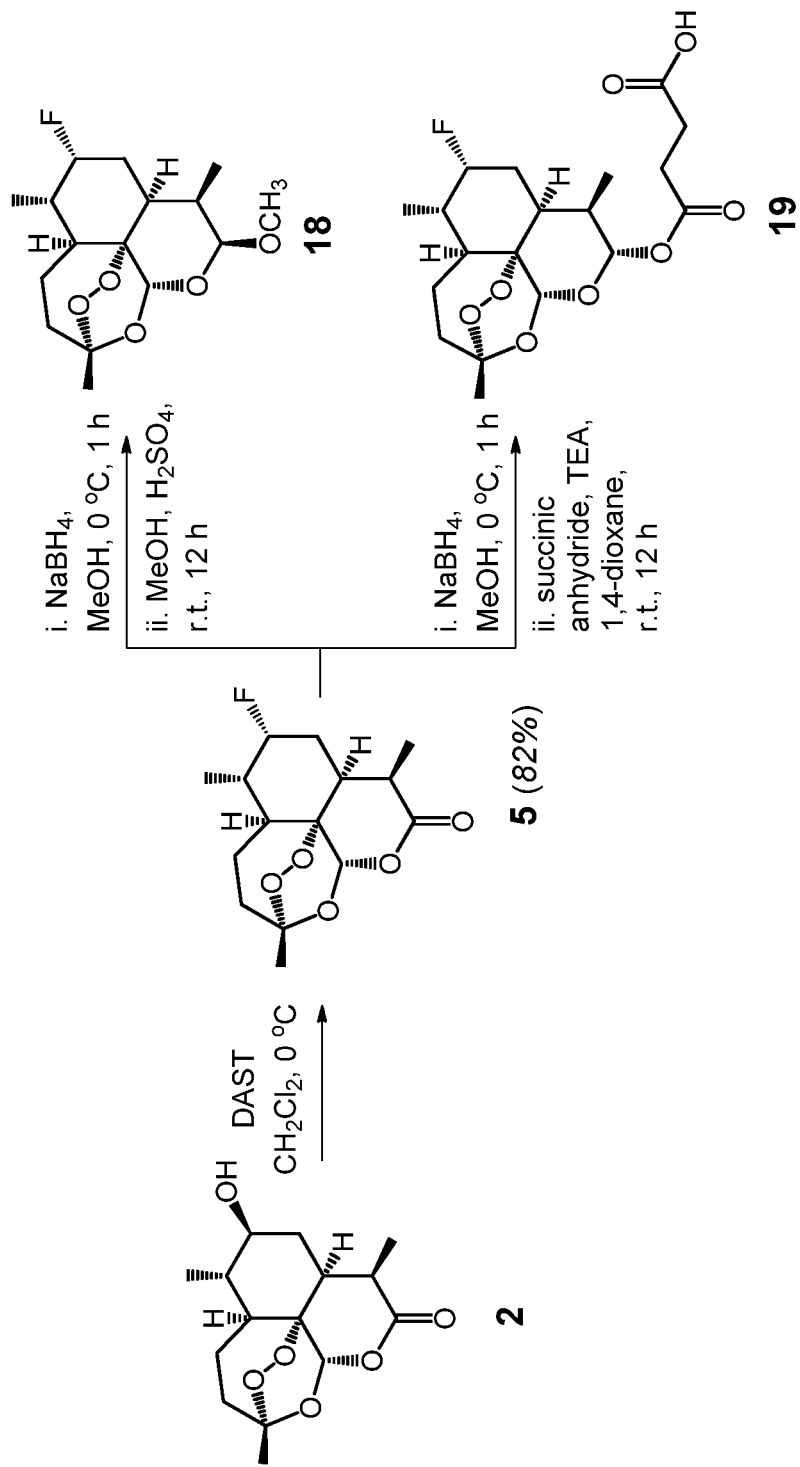

FIG. 6. Synthesis of 7,10-disubstituted derivatives of artemisinin according to one embodiment of the methods disclosed herein.

5. DETAILED DESCRIPTION OF THE INVENTION

Provided herein are derivatives of the antimalarial agent artemisinin, methods and compositions for preparation of the derivatives, and their uses in pharmaceutical compositions intended for the treatment of parasitic infections. Methods are also provided for the production of artemisinin derivatives via functionalization of positions C7 and C6a, and optionally, in some embodiments, in conjunction with modifications at positions C10 and C9, via chemoenzymatic methods. The derivatives of artemisinin prepared according to methods and procedures disclosed herein can be used for the treatment of malaria and other parasitic infections, and optionally, in some embodiments, in combination with other antiparasitic drugs.

Methods are also provided for chemically manipulating metabolically labile positions in artemisinin carbocyclic scaffold, such as positions C7 and C6a, which constitute primary targets of human liver P450-mediated metabolism. These methods are useful to functionalize these positions, and optionally, in some embodiments, in conjunction with functionalizations at the C10 or C9 site, to generate next-generation artemisinin-derived antimalarial agents.

Also provided are methods for the generation of artemisinin derivatives functionalized at positions C7 and C6a. The inventor has discovered that engineered variants of non-human cytochrome P450 enzymes can be used for the hydroxylation of these unactivated, aliphatic sites in artemisinin and derivatives thereof. Thus, in one embodiment, engineered variants of non-human cytochrome P450 enzyme are provided.

According to the methods disclosed herein, these P450-catalyzed C—H hydroxylation reactions, catalyzed, in certain embodiments, by the engineered variants of non-human cytochrome P450 enzymes, can be coupled to chemical transformations of hydroxyl group interconversion in order to install a broad range of novel functionalities at these relevant yet unreactive sites of the molecule. As demonstrated herein, these enzymatic transformations can be carried out using artemisinin as well as semisynthetic artemisinin derivatives, such as 10- or 9-substituted artemisinin derivatives, as substrates. As further demonstrated herein, the methods provided herein can also be applied to enable the production of polyfunctionalized artemisinin derivatives that carry multiple substitutions such as, for example, at a position within the carbocyclic backbone of the molecule (i.e., C7 or C6a) and at a position within the lactone ring (e.g., C10 and/or C9).

Attempts to carry out the oxidation of artemisinin have been reported in the past, these approaches relying on the use of oxidizing microbial strains such as *Beauveria sulfurescens, Aspergillus niger, Cunninghella elegans, Streptomyces griseus* strains (Zhan, Zhang et al. 2002; Parshikov, Muraleedharan et al. 2004; Liu, Chen et al. 2006; Parshikov, Miriyala et al. 2006; Patel, Gaur et al. 2010). See also Ziffer et al., U.S. Pat. No. 5,171,676. However, these biotransformations have typically involved long reaction times (5-20 days) and resulted in mixtures of multiple (over)oxidation products and/or a large extent of artemisinin deoxygenation to give deoxoartemisinin, which lacks the endoperoxide bridge essential for biological activity. In addition, the biological catalyst(s) responsible for artemisinin oxidation in these organisms were not identified or characterized.

Prior to the inventor's discovery, the utility of non-human cytochrome P450 monooxygenases for the oxyfunctionalization of artemisinin or semisynthetic derivative thereof was unknown. The inventor has discovered that engineered variants of natural cytochrome P450 monooxygenase enzymes can be exploited for the purpose of hydroxylating aliphatic positions in the artemisinin carbocyclic backbone (i.e., position C7 and C6a) with high efficiency (i.e., high turnover numbers), with short reaction time (e.g., less than 4 to 24 hours), and, in some cases, with excellent degrees of regio- and stereoselectivity (>90-99%), while preserving the integrity of critical functionalities in the molecule such as the endoperoxide bridge and the lactone ring.

Thus, in another embodiment, a method is provided for hydroxylating aliphatic positions in the artemisinin carbocyclic backbone (i.e., position C7 and C6a).

Methods for synthesizing C7- or C6a-functionalized derivatives of artemisinin and of 10-substituted artemisinin analogs are provided herein. Methods are provided herein to generate derivatives of this type via a two-step chemoenzymatic strategy, in which artemisinin or a derivative thereof, are first hydroxylated to generate 7(S)-hydroxy-, 7(R)-hydroxy-, or 6a-hydroxy derivatives of these compounds by means of one or more engineered P450 monooxygenases. After isolation (e.g., via chromatography or extraction), the hydroxylated derivatives are subjected to chemical reaction conditions suitable for converting the enzymatically installed hydroxyl group (—OH) into a different functional group, such as a halogen, an ether group, a thioether group, an acyloxy group, an amide group, or an amino group. Several reagents and reaction conditions are known in the art to perform the chemical interconversion of a hydroxyl group (—OH), including reagents and reaction conditions for alkylation, acylation, deoxohalogenation, and nucleophilic substitution of a hydroxyl group (—OH). As disclosed herein, using the chemoenzymatic approach and methods provided herein, new classes of singly (7- or 6a-substituted) or doubly (e.g., 6a,7-disubstituted; 7,10-disubstituted; or 6a,10-disubstituted) functionalized artemisinin derivatives can be also produced.

Furthermore, using the methods provided herein, it is also possible to first generate 7- or 6a-substituted artemisinin derivatives chemoenzymatically and then use these enzymatic products as intermediates to synthesize doubly substituted artemisinin derivatives (e.g., 7,10- or 6a,10-disubstituted derivatives), in which the C10 and/or C9 position(s) are modified. Methods that are suitable for the functionalization of artemisinin C10- and/or C9 site(s) (see, e.g., O'Neill and Posner 2004; Chaturvedi, Goswami et al. 2010) can be applied, provided that the reaction conditions involved in these processes are compatible with the functional group(s) contained within the substituent(s) preinstalled in position C7 and/or C6a. Determining the compatibility of such reaction conditions is well known in the art.

For clarity of disclosure, and not by way of limitation, the detailed description of the invention is divided into the subsections set forth below.

5.1 Definitions

The term "functional group" as used herein refers to a contiguous group of atoms that, together, may undergo a chemical reaction under certain reaction conditions. Examples of functional groups are, among many others, —OH, —NH$_2$, —SH, —(C=O)—, —N$_3$, —C≡CH.

The term "contact" as used herein with reference to interactions of chemical units indicates that the chemical units are at a distance that allows short range non-covalent interactions (such as Van der Waals forces, hydrogen bonding, hydrophobic interactions, electrostatic interactions, dipole-dipole interactions) to dominate the interaction of the chemical units. For example, when a protein is 'contacted' with a chemical species, the protein is allowed to interact with the chemical species so that a reaction between the protein and the chemical species can occur.

The term "polypeptide", "protein", and "enzyme" as used herein refers to any chain of two or more amino acids bonded in sequence, regardless of length or post-translational modification. According to their common use in the art, the term "protein" refers to any polypeptide consisting of more than 50 amino acid residues. These definitions are however not intended to be limiting.

In general, the term "mutant" or "variant" as used herein with reference to a molecule such as polynucleotide or polypeptide, indicates that such molecule has been mutated from the molecule as it exists in nature. In particular, the term "mutate" and "mutation" as used herein indicates any modification of a nucleic acid and/or polypeptide which results in an altered nucleic acid or polypeptide. Mutations include any process or mechanism resulting in a mutant protein, enzyme, polynucleotide, or gene. A mutation can occur in a polynucleotide or gene sequence, by point mutations, deletions, or insertions of single or multiple nucleotide residues. A mutation in a polynucleotide includes mutations arising within a protein-encoding region of a gene as well as mutations in regions outside of a protein-encoding sequence, such as, but not limited to, regulatory or promoter sequences. A mutation in a coding polynucleotide such as a gene can be "silent", i.e., not reflected in an amino acid alteration upon expression, leading to a "sequence-conservative" variant of the gene. A mutation in a polypeptide includes but is not limited to mutation in the polypeptide sequence and mutation resulting in a modified amino acid. Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like.

The term "engineer" refers to any manipulation of a molecule that result in a detectable change in the molecule, wherein the manipulation includes but is not limited to inserting a polynucleotide and/or polypeptide heterologous to the cell and mutating a polynucleotide and/or polypeptide native to the cell.

The term "polynucleotide molecule" or "nucleic acid molecule" as used herein refers to any chain of two or more nucleotides bonded in sequence. For example, a polynucleotide molecule or a nucleic acid molecule can be, for example a DNA or a RNA. Other nucleic acid molecules are well known in the art, e.g., artificial nucleic acid analogs.

The terms "vector" and "vector construct" as used herein refer to a vehicle by which a DNA or RNA sequence (e.g., a foreign gene) can be introduced into a host cell, so as to transform the host and promote expression (e.g., transcription and translation) of the introduced sequence. A common type of vector is a "plasmid", which generally is a self-contained molecule of double-stranded DNA that can be readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clontech Laboratories, Inc., Mountain View, Calif.), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. The terms "express" and "expression" refer to allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

The term "fused" as used herein means being connected through one or more covalent bonds. The term "bound" as used herein means being connected through non-covalent interactions. Examples of non-covalent interactions are van der Waals, hydrogen bond, electrostatic, and hydrophobic interactions. The term "tethered" as used herein means being connected through covalent or non-covalent interactions. Thus, a "polypeptide tethered to a solid support" refers to a polypeptide that is connected to a solid support (e.g., surface, resin bead) either via non-covalent interactions or through covalent bonds.

5.2 P450 Monooxygenase Enzymes

Engineered cytochrome P450 polypeptides are provided having the capability to oxidize at least one substrate selected from the group consisting of artemisinin, dehydroartemisinin, and a C10-substituted derivative of artemisinin, wherein the cytochrome P450 polypeptide comprises an amino acid sequence having at least 60% sequence identity to SEQ. ID NO:1, SEQ. ID NO:2, or SEQ. ID NO:3 over a region of at least about 100, 200, 300, 400, 500, 1000, or more residues.

In some embodiments, the capability to oxidize a least one substrate from the group of compounds as defined above corresponds to the capability of the cytochrome P450 polypeptide to hydroxylate a C—H bond attached to the carbon atom C6a in said substrate. In other embodiments, such capability corresponds to the capability of the cytochrome P450 polypeptide to hydroxylate a C—H bond attached to the carbon atom C7 in said substrate, where the resulting hydroxylated product has predominantly (S) or (R) stereochemistry at the hydroxylation site (C7) according to the stereoselectivity of the enzyme.

In some embodiments, the substrate which is hydroxylated by the cytochrome P450 polypeptide is a compound of formula (I),

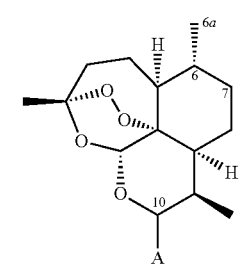

(I)

wherein A represents a carbonyl group (═O), a hydroxy group (—OH), a halogen atom, an optionally substituted alkyloxy, alkenyloxy, or alkynyloxy group, an optionally substituted aryloxy or heteroaryloxy group, or a group —NR$_1$R$_2$, where R$_1$ represents a hydrogen atom or an optionally substituted alkyl, alkenyl, or alkynyl group;

wherein R$_2$ represents an optionally substituted alkyl, alkenyl, alkynyl, aryl, or heteroaryl group; or wherein R$_1$ and R$_2$ are connected together to form an optionally substituted heterocyclic group.

In some embodiments, the substrate of general formula (I) is artemisinin and the products of the oxidation reaction catalyzed by the cytochrome P450 polypeptide comprise one or more compounds from the group consisting of 6a-hydroxy-ART, 7(S)-hydroxy-ART, and 7(R)-hydroxy-ART.

In others embodiments, the substrate of general formula (I) is a C10-substituted analog of artemisinin and the products of the oxidation reaction catalyzed by the cytochrome P450 polypeptide comprise one or more compounds from the group consisting of 6a-hydroxy-, 7(S)-hydroxy-, and 7(R)-hydroxy-derivative of said analog.

Engineered cytochrome P450 polypeptides are provided that are capable of hydroxylating a C—H bond at position 6a, position 7, or both, in artemisinin or analog thereof, and which have an improved property compared with a reference enzyme, such as the naturally occurring enzymes from which they were derived, said naturally occurring enzymes being CYP102A1 from *Bacillus megaterium* (SEQ ID NO.: 1), CYP102A5 *Bacillus cereus* (SEQ ID NO.: 2), or CYP505X from *Aspergillus fumigatus* (SEQ ID NO.: 3), or when compared with other engineered cytochrome P450 enzymes, such as the polypeptide of SEQ ID NO.: 4.

In the characterization of the cytochrome P450 enzymes disclosed herein, the polypeptides can be described in reference to the amino acid sequence of a naturally occurring cytochrome P450 enzyme or another engineered cytochrome P450 enzyme. As such, the amino acid residue is determined in the cytochrome P450 enzymes beginning from the initiating methionine (M) residue (i.e., M represent residue position 1), although it will be understood that this initiating methionine residue may be removed by biological processing machinery such as in a host cell or in vitro translation system, to generate a mature protein lacking the initiating methionine residue. The amino acid residue position at which a particular amino acid or amino acid change is present is sometimes described herein as "Xn", or "position n", where n refers to the residue position.

As described above, the cytochrome P450 enzymes disclosed herein are characterized by an improved enzyme property as compared to the naturally occurring parent enzyme or another engineered cytochrome P450 enzyme Improved enzyme properties are discussed herein below.

Changes to enzyme properties are well known in the art and can include, but are not limited to, improvements in enzymatic activity, regioselectivity, stereoselectivity, and/or reduced substrate or product inhibition. In the embodiments herein, the altered properties are based on engineered cytochrome P450 polypeptides having residue differences at specific residue positions as compared to a reference sequence of a naturally occurring cytochrome P450 enzyme, such as CYP102A1 (SEQ ID NO.: 1), CYP102A5 (SEQ ID NO.: 2), or CYP505X (SEQ ID NO.: 3), or as compared to another engineered cytochrome P450 enzyme, such as the polypeptide of SEQ ID NO.: 4.

In some embodiments, the P450 monooxygenase is an engineered variant of CYP102A1 (SEQ ID NO.: 1), said variant comprising an amino acid change at one or more of the following positions of SEQ ID NO.: 1: X26, X27, X43, X48, X52, X73, X75, X76, X79, X82, X83, X88, X143, X176, X181, X182, X185, X189, X198, X206, X227, X237, X253, X256, X261, X264, X265, X268, X269, X291, X329, X330, X354, X355, X438, and X439.

In some embodiments, the P450 monooxygenase is an engineered variant of CYP102A5 (SEQ ID NO.: 2), said variant comprising an amino acid change at one or more of the following amino acid positions of SEQ ID NO.:2: X28, X29, X45, X50, X54, X75, X77, X78, X81, X83, X85, X90, X145, X178, X183, X184, X187, X191, X208, X229, X239, X255, X256, X263, X266, X267, X270, X271, X293, X331, X332, X356, X357, and X440.

In some embodiments, the P450 monooxygenase is an engineered variant of CYP505X (SEQ ID NO.: 3), said variant comprising an amino acid change at one or more of the following amino acid positions of SEQ ID NO.:3: X29, X30, X46, X51, X55, X76, X78, X79, X82, X84, X86, X91, X146, X179, X184, X185, X188, X192, X209, X230, X240, X256, X257, X264, X267, X268, X271, X272, X294, X332, X333, X364, X365, and X448.

In some embodiments, the cytochrome P450 polypeptides can have additionally one or more residue differences at residue positions not specified by an X above as compared to the sequence SEQ ID NO.: 1, SEQ ID NO.: 2, or SEQ ID NO.: 3. In some embodiments, the differences can be 1-2, 1-5, 1-10, 1-20, 1-30, 1-40, 1-50, 1-75, 1-100, 1-150, or 1-200 residue differences at other amino acid residue positions not defined by X above.

In some embodiments, the cytochrome P450 polypeptides can have additionally one or more residue differences at residue positions not specified by an X above and located within the "heme domain" of the enzyme, as compared to the sequence SEQ ID NO.: 1, SEQ ID NO.: 2, or SEQ ID NO.: 3. In some embodiments, the differences can be 1-2, 1-5, 1-10, 1-20, 1-30, 1-40, 1-50, 1-75, 1-100, 1-150, or 1-200 residue differences at other amino acid residue positions not defined by X above and located within the "heme domain" of the enzyme.

In some embodiments, the engineered cytochrome P450 polypeptides having one or more of the improved enzyme properties described herein, can comprise an amino acid sequence that is at least 60%, 70%, 80%, 85%, 90%, 95%, 99% or more identical to the sequence SEQ ID NO.: 1, SEQ ID NO.: 2, or SEQ ID NO.: 3.

In some embodiments, the engineered cytochrome P450 polypeptides having one or more of the improved enzyme properties described herein, can comprise an amino acid sequence encompassing its heme domain which is at least 60%, 70%, 80%, 85%, 90%, 95%, 99% or more identical to the amino acid sequence encompassing the first 500 amino acids in the sequence SEQ ID NO.: 1, SEQ ID NO.: 2, or SEQ ID NO.: 3 (i.e., residue 1 to residue 500 in these reference sequences).

In some embodiments, the improved cytochrome P450 polypeptide can comprise an amino acid sequence that is at least 60%, 70%, 80%, 85%, 90%, 95%, 99% or more identical to a sequence corresponding to SEQ ID NO.: 4, 5, 6, 7, 8, 9, 10, 11, 12, 13, 14, or 15.

In some embodiments, the improved cytochrome P450 polypeptide can comprise an amino acid sequence encompassing its heme domain that is at least 60%, 70%, 80%, 85%, 90%, 95%, 99% or more identical to the sequence encompassing the first 500 amino acids in SEQ ID NO.: 4, 5, 6, 7, 8, 9, 10, 11, 12, 13, 14, or 15.

In some embodiments, the improved cytochrome P450 polypeptide comprises an amino acid sequence corresponding to the sequence of SEQ ID NO.: 4, 5, 6, 7, 8, 9, 10, 11, 12, 13, 14, or 15.

In some embodiments, the improved enzyme property of the engineered P450 polypeptide is with respect to its catalytic activity, coupling efficiency, regioselectivity and/or stereoselectivity.

The improvement in catalytic activity can be manifested by an increase in the number of total turnovers supported by the P450 polypeptide on a given substrate as compared to the wild-type parental sequence (SEQ ID NO.: 1, SEQ ID NO.: 2, or SEQ ID NO.: 3), or other reference sequences (e.g., SEQ ID NO.: 4). In some embodiments, the cytochrome P450 polypeptides are capable of supporting a number of total turnovers that is at least 1.1-fold, 2-fold, 5-fold, 10-fold, 100-fold, 200-fold, 500-fold, or more higher than the number of total turnovers supported by its respective naturally occurring parental sequence SEQ ID NO.: 1, SEQ ID NO.: 2, or SEQ ID NO.: 3.

The improvement in catalytic activity can be also manifested by an increase in the catalytic efficiency for the oxidation of a given substrate, this catalytic efficiency being conventionally defined by the $k_{cat}/K_M$ ratio, where $k_{cat}$ is the turnover number and $K_M$ is the Michaelis-Menten constant, as compared to the wild-type parental sequence (SEQ ID NO.: 1, SEQ ID NO.: 2, or SEQ ID NO.: 3), or other reference sequences (e.g., SEQ ID NO.: 4).

In some embodiments, the engineered P450 polypeptides having improved catalytic activity on the substrate comprise an amino acid sequence corresponding to SEQ ID NO.: 4, 5, 6, 7, 8, 9, 10, 11, 12, 13, 14, or 15.

The improvement in coupling efficiency can be manifested by an increase in the ratio between the moles of oxidation product formed by the enzyme per unit of time and the moles of cofactor molecules (e.g., NAD(P)H) consumed by the enzyme per unit of time. In some embodiments, the cytochrome P450 polypeptides are capable of oxidizing the substrate with a coupling efficiency that is at least 1%, 2%, 5%, 10%, 20%, 30%, 40%, 50%, 75%, 90%, 98%, 99% or more higher than the coupling efficiency of its respective naturally occurring parental sequence SEQ ID NO.: 1, SEQ ID NO.: 2, or SEQ ID NO.: 3 or the reference sequence SEQ ID NO.: 4.

In some embodiments, the engineered P450 polypeptides having improved coupling efficiency comprise an amino acid sequence corresponding to SEQ ID NO.: 4, 5, 6, 7, 8, 9, 10, 11, 12, 13, 14, or 15.

The improvement in regioselectivity can be manifested by an increase in the selectivity by which a particular C—H bond in the substrate is oxidized by action of the engineered cytochrome P450 polypeptide over the other C—H bonds occurring in the molecule as compared to the wild-type parental sequence (SEQ ID NO.: 1, SEQ ID NO.: 2, or SEQ ID NO.: 3), or other reference sequences (e.g., SEQ ID NO.: 4). In some embodiments, the cytochrome P450 polypeptides are capable of oxidizing the substrate with a regioselectivity that is at least 1%, 2%, 5%, 10%, 20%, 30%, 40%, 50%, 75%, 90%, 98%, 99% or more higher than that exhibited by its respective wild-type parental sequence SEQ ID NO.: 1, SEQ ID NO.: 2, or SEQ ID NO.: 3 or the reference sequence SEQ ID NO.: 4 toward the oxidation of the same C—H bond in the substrate.

In some embodiments, the engineered P450 polypeptides having improved regioselectivity toward oxidation of carbon atom C7 in the substrate comprise an amino acid sequence corresponding to SEQ ID NO.: 4, 5, 6, 7, 8, 9, 10, 11, or 12. In some embodiments, the engineered P450 polypeptides having improved regioselectivity toward oxidation of carbon atom C6a in the substrate comprise an amino acid sequence corresponding to SEQ ID NO.: 13, 14, or 15.

In some embodiments, the improvement in stereoselectivity can be manifested by an increase in the stereoselectivity by which a C—H bond in a prochiral carbon atom of the substrate (e.g., C7) is oxidized by action of the engineered cytochrome P450 polypeptide as compared to the wild-type parental sequence (SEQ ID NO.: 1, SEQ ID NO.: 2, or SEQ ID NO.: 3), or other reference sequences (e.g., SEQ ID NO.: 4). The degree of stereoselectivity can be conventionally described in terms of stereomeric excess, that is in terms of enantiomeric excess (ee) or diastereomeric excess (de) depending on the nature of the substrate. In some embodiments, the improvement in stereoselectivity in the engineered cytochrome P450 polypeptide is with respect to producing the (S) stereoisomer of the hydroxylation product (i.e., stereoisomer in which the absolute configuration of the hydroxylation site is (S)). In some embodiments, such improvement in stereoselectivity is with respect to producing the (R) stereoisomer of the hydroxylation product. In some embodiments, the cytochrome P450 polypeptides are capable of oxidizing the substrate with a (S)- or (R)- stereoselectivity (i.e., stereomeric excess) that is at least 1%, 2%, 5%, 10%, 20%, 30%, 40%, 50%, 75%, 90%, 98%, 99% or more higher than that exhibited by its respective wild-type parental sequence SEQ ID NO.: 1, SEQ ID NO.: 2, or SEQ ID NO.: 3, or the reference sequence SEQ ID NO.: 4, toward the oxidation of the same carbon atom in the substrate.

In some embodiments, the engineered P450 polypeptides having improved stereoselectivity toward oxidation of carbon atom C7 in the substrate comprise an amino acid sequence corresponding to SEQ ID NO.: 4, 5, 6, 7, 8, 9, 10, 11, or 12.

In some embodiments, the engineered cytochrome P450 polypeptides are capable of oxidizing artemisinin and structurally diverse analogs of artemisinin. In some instances, the catalytic activity for the naturally occurring parent enzymes CYP102A1 (SEQ ID NO.: 1), CYP102A5 (SEQ ID NO.: 2), or CYP505X (SEQ ID NO.: 3), on artemisinin or on the structurally different analogs of artemisinin may be insignificant. Accordingly, in some embodiments, the engineered cytochrome P450 polypeptides are characterized by improved catalytic activity for substrate that are not oxidized at significant levels by the polypeptides of SEQ ID NO.: 1, SEQ ID NO.: 2, or SEQ ID NO.: 3.

The capability of the engineered cytochrome P450 polypeptides to oxidize a substrate of general formula (I) can be established according to methods well known in the art. Most typically, such capability can be established by contacting the substrate with the P450 monooxygenase under suitable reaction conditions in which the P450 monooxygenase is catalytically functional, and then determining the formation of an oxidized product of the substrate (e.g., hydroxylated product) by standard analytical methods such as, for example, thin-layer chromatography, HPLC, and/or LC-MS.

Various art-known methods can be applied for measuring the catalytic activity of the engineered cytochrome P450 polypeptide on the substrate of general formula (I), also referred to herein as "substrate activity". Such substrate activity can be measured by measuring the decrease of the amount of substrate, the accumulation of an oxygenation product derived from the substrate (e.g., hydroxylated product), or the accumulation of an oxidation byproduct generated during the enzymatic reaction (e.g., $H_2O_2$), after a given time after contacting the substrate with the P450 monooxygenase under suitable reaction conditions in which the P450 monooxygenase is catalytically functional. Other methods to measure the substrate activity include measuring the consumption of a cofactor (e.g., NADPH or NADH) or cosubstrate ($O_2$) utilized by the enzyme during the oxidation reaction. The choice of the method will vary depending on the specific application such as, for example, according to the nature of the substrate, the nature of the monooxygenase (e.g., its NAD(P)H cofactor specificity), and the number of the P450 monooxygenases that are to be evaluated. A person skilled in the art will be capable of selecting the most appropriate method in each case.

The substrate activity of engineered cytochrome P450 polypeptides can be measured and expressed in terms of number of catalytic turnovers, product formation rate, cofactor consumption rate, $O_2$ consumption rate, $H_2O_2$ consumption rate (e.g., for $H_2O_2$-dependent monooxygenases), and the like. Most conveniently, such substrate activity can be measured and expressed in terms of total turnover numbers (or TTN), which corresponds to the total number of catalytic turnovers supported by the P450 monooxygenase enzyme on this substrate.

In some embodiments, the engineered cytochrome P450 polypeptides disclosed herein are capable of supporting at least 1, 10, 50, 100, or more TTN in the oxidation of the substrate of general formula (I).

The regio- and stereoselectivity of the engineered cytochrome P450 polypeptides for the oxidation of the substrate of general formula (I) can be measured by determining the relative distribution of oxidation products generated by the reaction between the substrate and the cytochrome P450 polypeptide using conventional analytical methods such as, for example, (chiral) normal phase liquid chromatography or (chiral) reverse-phase liquid chromatography. In some instances, the oxidation products can be subjected to a chemical derivatization process to facilitate these analyses. For example, the hydroxylation products obtained from the reaction of the P450 polypeptide with artemisinin or analog thereof can be derivatized using an UV-active acid chloride (e.g., benzoyl chloride) prior to separation and quantification by HPLC.

In some embodiments, the engineered cytochrome P450 polypeptides disclosed herein are capable of hydroxylating a C—H bond connected to the C6a or C7 carbon atom in the substrate of general formula (I) with a regioselectivity of 1%, 5%, 10%, 25%, 50%, 75%, 90%, 95%, 99% or higher.

In some embodiments, the P450 monooxygenase is selected from the group of CYP102A1 (SEQ ID NO: 1)-derived variants consisting of FL#41 (SEQ ID NO. 4), FL#47 (SEQ ID NO. 5), FL#48 (SEQ ID NO. 6), FL#49 (SEQ ID NO. 7), FL#59 (SEQ ID NO. 6), FL#62 (SEQ ID NO. 8). These P450 monooxygenases were found to be capable of hydroxylating compounds of general formula (I), such as artemisinin and analog thereof, with varying catalytic activity (i.e., with varying numbers of total turnovers) and with varying degree of regio- and stereoselectivity. In contrast, wild-type CYP102A1 (SEQ ID NO. 1) exhibits no significant catalytic on these substrates (TTN<1). For example, FL#62 (SEQ ID NO. 8) was found to be capable of hydroxylating artemisinin with high catalytic activity (339 TTN), producing 7(S)-hydroxy-ART (2), 7(R)-hydroxy-ART (3), and 6a-hydroxy-ART (4) in 83:10:7 ratio (FIG. 1). As another example, FL#41 (SEQ ID NO. 4) is capable of hydroxylating artemisinin producing 7(S)-hydroxy-ART (2), 7(R)-hydroxy-ART (3), and 6a-hydroxy-ART (4) in 90:8:2 ratio and supporting about 50 total turnovers.

Compared to its naturally occurring parent enzyme CYP102A1 (SEQ ID NO. 1), FL#62 (SEQ ID NO. 8) carries the following amino acid changes: V79A, F82S, A83V, F88A, P143S, T176I, A181T, A185V, A198V, F206C, S227R, H237Q, E253G, R256S, A291V, L354V.

In some embodiments, the cytochrome P450 polypeptide is selected from the group of FL#62 (SEQ ID NO: 8)-derived variants consisting of IV-H4 (SEQ ID NO. 9), V-H2 (SEQ ID NO. 10), II-H10 (SEQ ID NO.11), III-B1 (SEQ ID NO.12), II-E2 (SEQ ID NO. 13), X-E12 (SEQ ID NO. 14), X-F11 (SEQ ID NO. 15). These cytochrome P450 polypeptides were prepared by mutagenesis of FL#62 (SEQ ID NO. 8) at one or more of the residues selected from the group consisting of residue X26, X27, X43, X48, X52, X73, X75, X76, X79, X82, X83, X88, X143, X176, X181, X182, X185, X189, X198, X206, X227, X237, X253, X256, X261, X264, X265, X268, X269, X291, X329, X330, X354, X355, X438, and X439. These cytochrome P450 polypeptides exhibit improved catalytic activity and/or regio- and stereoselectivity toward the hydroxylation of artemisinin compared to the wild-type enzyme CYP102A1 (SEQ ID NO. 1) or to FL#62 (SEQ ID NO. 8). As an example, IV-H4 (SEQ ID NO. 9), which carries the amino acid mutations A78S, S81V, V82A compared to FL#62 (SEQ ID NO. 8), exhibits improved regio- and stereoselectivity for C7 hydroxylation (>99.9% regioselectivity, >99.9% (S)-stereoselectivity) as well as improved catalytic activity (TTN: 362).

In some embodiments, the cytochrome P450 polypeptide is capable of oxidizing a C10-substituted artemisinin analog selected from the group consisting of dihydroartemisinin, artemether, artesunate methyl ester, and 10-trimethylsylylether-artemisinin. These substrates corresponding to compounds of general formula (I), where A is —OH, —OCH$_3$, —OC(O)CH$_2$—CH$_2$C(O)OCH$_3$, or —OSi(CH$_3$)$_3$, respectively.

In some embodiments, the improved engineered cytochrome P450 polypeptides comprise deletions of the engineered cytochrome P450 polypeptides disclosed herein. Accordingly, for each of the embodiment of the cytochrome P450 polypeptides disclosed herein, the deletions can comprise 1, 2, 5, 10, 50, 100 or more amino acids, as long as the functional activity and/or improved properties of the P450 polypeptide is maintained.

In some embodiments, the improved engineered cytochrome P450 polypeptides can comprise fragments of the engineered cytochrome P450 polypeptides disclosed herein. In some embodiments, the polypeptide fragments can be 50%, 60%, 70%, 80%, 90%, 95%, 98%, or 99% of the full-length cytochrome P450 polypeptide, such as the polypeptides of SEQ ID NO. 4 through 15.

In some embodiments, the improved engineered cytochrome P450 polypeptides can comprise only the heme domain of the engineered cytochrome P450 polypeptides disclosed herein. Typically, albeit not necessarily, such heme domain is encompassed by the first (i.e., N-terminal) 500 amino acid residues of the engineered cytochrome P450 polypeptides. The heme domain comprises the active site in which the substrate binds and is oxidized. The amino acid mutations comprised within the heme domain are therefore primarily responsible for the improved substrate recognition properties and/or regio- and stereoselectivity properties of the engineered cytochrome P450 polypeptides. The remainder of the polypeptide sequence comprises the reductase component of the enzyme (FMN/FAD diflavin-dependent reductase domain), whose role is to transfer electrons from a soluble cofactor (i.e., NADPH) to the heme domain to drive the catalytic cycle.

It is known in the art that the heme domain in catalytically self-sufficient cytochrome P450 enzymes such as CYP102A1 (SEQ ID NO: 1), CYP102A5 (SEQ ID NO: 2), and CYP505X (SEQ ID NO: 3) can be covalently or non-covalently linked to a non-native electron-transfer system resulting in a functional, artificial P450 system. For example, the non-native electron-transfer system may be the reductase domain of a P450 enzyme from the same CYP subfamily (Landwehr, Carbone et al. 2007), the reductase domain of a P450 enzyme from a different CYP subfamily (e.g., RhF reductase)(Li, Podust et al. 2007), or the redox partners of a class I P450 system (e.g., ferrodoxin and ferrodoxin reductase)(Hirakawa and Nagamune 2010). Alternatively, the non-native electron-transfer system can be an electrode or light in combination or not with redox active compounds, which deliver one or more electrons to the P450 heme domain to drive catalysis. Alternatively, the non-native electron-transfer system can be a chemical reagent, such as H$_2$O$_2$ or an organic peroxide, which can react with the heme cofactor in the heme domain of the P450 polypeptide and drive catalysis through the peroxide shunt pathway, thereby serving as a source of both oxygen and electrons and bypassing the need for a reductase component.

Accordingly, in some embodiments, the improved engineered cytochrome P450 polypeptide or a fragment thereof (e.g., its heme domain), is comprised in an artificial P450 system, that is, a system that comprises the full-length cytochrome P450 polypeptide or a fragment thereof and an exogenous electron-transfer system, this exogenous electron-transfer system being one or more protein-based, chemical, or physical agents, which can deliver one or more electrons to the heme cofactor in the P450 polypeptide.

In some embodiments, the improved engineered cytochrome P450 polypeptides can comprise one or more non-natural amino acids. The non-natural amino acid can be present at one or more of the positions defined by "Xn" above for the purpose of modulating the enzyme properties of the polypeptide. Alternatively, the non-natural amino acid can be introduced in another position of the polypeptide sequence for the purpose, for example, of linking the P450 polypeptide to another protein, another biomolecule, or a solid support. Several methods are known in the art for introducing an unnatural amino acid into a polypeptide. These include the use of the amber stop codon suppression methods using engineered tRNA/aminoacyl-tRNA synthetase (AARS) pairs such as those derived from *Methanococcus jannaschi* tRNA/AARS and *Metanosarcina* sp. tRNA/AARS (Liu, C. C. & Schultz, P. G. Annu. Rev. Biochem., 2010, 79, 413). Alternatively, natural or engineered frameshift suppressor tRNAs and their cognate aminoacyl-tRNA synthetases can also be used for the same purpose (Rodriguez et al. Proc. Natl. Acad. Sci. U.S.A., 2006, 103, 8650; Neumann et al., J. Am. Chem. Soc., 2010, 132, 2142). Alternatively, an unnatural amino acid can be incorporated in a polypeptide using chemically (Dedkova et al., J. Am. Chem. Soc., 2003, 125, 6616) or enzymatically (Bessho et al. Nat. Biotechnol., 2002, 20, 723) aminoacylated tRNA molecules and using a cell-free protein expression system in the presence of the aminoacylated tRNA molecules (Murakami, H.; Ohta, A.; Ashigai, H.; Suga, H. Nat Methods, 2006, 3, 357; Kourouklis, D.; Murakami, H.; Suga, H. Methods, 2005, 36, 239). Examples of non-natural amino acids include but are not limited to, para-acetyl-phenylalanine, meta-acetyl-phenylalanine, para-butyl-1,3-dione-phenylalanine, 0-allyl-tyrosine, 0-propargyl-tyrosine, para-azido-phenylalanine, para-borono-phenylalanine, para-bromo-phenylalanine, para-iodo-phenylalanine, 3-iodo-tyrosine, para-benzoyl-phenylalanine, para-benzoyl-phenyl-alanine, E-N-allyloxycarbonyl-lysine, E-N-propargyloxycarbonyl-lysine, E-N-azidoethyloxycarbonyl-lysine, and E-N-(o-azido-benzyl)-oxycarbonyl-lysine In some embodiments, the polypeptide described herein can be provided in form of a kit. These kits may contain an individual enzyme or a plurality of enzymes. The kits can further include reagents for carrying out the enzymatic reactions, substrates for assessing the activity of the enzymes, and reagents for detecting the products. The kits can also include instructions for the use of the kits.

In some embodiments, the polypeptides described herein can be covalently or non-covalently linked to a solid support for the purpose, for example, of screening the enzymes for activity on a range of different substrates or for facilitating the separation of reactants and products from the enzyme after the enzymatic reactions. Examples of solid supports include but are not limited to, organic polymers such as polystyrene, polyacrylamide, polyethylene, polypropylene, polyethyleneglycole, and the like, and inorganic materials such as glass, silica, controlled pore glass, metals. The configuration of the solid support can be in the form of beads, spheres, particles, gel, a membrane, or a surface.

5.3 Polynucleotides and Host Cells for Expression of P450 Monooxygenase Enzymes In another embodiment, recombinant or engineered polynucleotide molecules are provided that encode for the improved cytochrome P450 polypeptides. The recombinant or engineered polynucleotides may be linked to one or more regulatory sequences controlling the expression of the cytochrome P450 polypeptide-encoding gene to form a recombinant polynucleotide capable of expressing the polypeptide.

Since the correspondence of all the possible three-base codons to the various amino acids is known, providing the amino acid sequence of the P450 polypeptide provides also a description of all the polynucleotide molecules encoding for such polypeptide. Thus, a person skilled in the art will be able, given a certain polypeptide sequence, to easily generate any number of different polynucleotides encoding for the same polypeptide. Preferably, the codons are selected to fit the host cell in which the polypeptide is being expressed. For example, preferred codons used in bacteria are preferably used to express the polypeptide in a bacterial host.

In some embodiments, the recombinant or engineered polynucleotide molecule comprises a nucleotide sequence encoding for a cytochrome P450 polypeptide with an amino acid sequence that is at least 60%, 70%, 80%, 85%, 90%, 95%, 99% or more identical to SEQ ID NO.: 1, 2, or 3.

In some embodiments, the recombinant or engineered polynucleotide molecule encoding for the improved cytochrome P450 polypeptide is comprised in a recombinant expression vector. Examples of suitable recombinant expression vectors include but are not limited to, chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used. A large number of expression vectors and expression hosts are known in the art, and many of these are commercially available. A person skilled in the art will be able to select suitable expression vectors for a particular application, e.g., the type of expression host (e.g., in vitro systems, prokaryotic cells such as bacterial cells, and eukaryotic cells such as yeast, insect, or mammalian cells) and the expression conditions selected.

In another embodiment, an expression host system is provided comprising a polynucleotide molecule encoding for the improved cytochrome P450 polypeptides. Expression host systems that may be used within the invention include any systems that support the transcription, translation, and/or replication of a polynucleotide molecule of the invention. Preferably, the expression host system is a cell. Host cells for use in expressing the polypeptides encoded by the expression vector disclosed herein are well known in the art and include but are not limited to, bacterial cells (e.g., *Escherichia coli, Streptomyces*); fungal cells such as yeast cells (e.g., *Saccharomyces cerevisiae, Pichia pastoris*); insect cells; plant cells; and animal cells. The expression host systems also include lysates of prokaryotic cells (e.g., bacterial cells) and lysates of eukaryotic cells (e.g., yeast, insect, or mammalian cells). These systems also include in vitro transcription/translation systems, many of which are commercially available. The choice of the expression vector and host system depends on the type of application intended for the methods of the invention and a person skilled in the art will be able to select a suitable expression host based on known features and application of the different expression hosts.

5.4 Methods of Preparing and Using the Engineered Cytochrome P450 Polypeptides The engineered cytochrome P450 polypeptides can be prepared via mutagenesis of the polynucleotide encoding for the naturally occurring cytochrome P450 enzymes (SEQ ID NO: 1, 2, or 3) or for an engineered variant thereof. Many mutagenesis methods are known in the art and these include, but are not limited to, site-directed mutagenesis, site-saturation mutagenesis, random mutagenesis, cassette-mutagenesis, DNA shuffling, homologous recombination, non-homologous recombination, site-directed recombination, and the like. Detailed description of art-known mutagenesis methods can be found, among other sources, in U.S. Pat. No. 5,605,793; U.S. Pat. No. 5,830,721; U.S. Pat. No. 5,834,252; WO 95/22625; WO 96/33207; WO 97/20078; WO 97/35966; WO 98/27230; WO 98/42832; WO 99/29902; WO 98/41653; WO 98/41622; WO 98/42727; WO 00/18906; WO 00/04190; WO 00/42561; WO 00/42560; WO 01/23401; WO 01/64864.

Numerous methods for making nucleic acids encoding for polypeptides having a predetermined or randomized sequence are known to those skilled in the art. For example, oligonucleotide primers having a predetermined or randomized sequence can be prepared chemically by solid phase synthesis using commercially available equipments and reagents. Polynucleotide molecules can then be synthesized and amplified using a polymerase chain reaction, digested via endonucleases, ligated together, and cloned into a vector according to standard molecular biology protocols known in the art (e.g., Sambrook et al. *Molecular Cloning: A Laboratory Manual* (Third Edition), Cold Spring Harbor Press, 2001). These methods, in combination with the mutagenesis methods mentioned above, can be used to generate polynucleotide molecules that encode for engineered cytochrome P450 polypeptides as well as suitable vectors for the expression of these polypeptides in a host expression system.

Engineered cytochrome P450 polypeptides expressed in a host expression system, such as, for example, in a host cell, can be isolated and purified using any one or more of the well known techniques for protein purification, including, among others, cell lysis via sonication or chemical treatment, filtration, salting-out, and chromatography (e.g., ion-exchange chromatography, gel-filtration chromatography, etc.).

The recombinant P450 polypeptides obtained from mutagenesis of a parental P450 enzyme sequences (e.g., SEQ ID NO: 1, 2, 3 or engineered variants thereof) can be screened for identifying engineered P450 polypeptides having improved enzyme properties, such as improvements with respect to their catalytic activity, coupling efficiency, regioselectivity and/or stereoselectivity for the oxidation of substrates of general formula (I). The improvement resulting from the introduced amino acid mutation(s) in any one or more of these enzyme properties can be then measured according to methods known in the art, as described above.

In some embodiments, a method is provided for hydroxylating a substrate of general formula (I) as defined above, the method comprising the steps of:
a. contacting said substrate with an engineered cytochrome P450 polypeptide;
b. allowing for the engineered cytochrome P450 enzyme to catalyze the hydroxylation of a C—H bond within said substrate, while preserving the endoperoxide bond therein, thereby producing a hydroxylated derivative of said substrate; and
c. isolating said hydroxylated derivative of said substrate.

In some embodiments, the C—H bond hydroxylated by the engineered cytochrome P450 polypeptide within the method is attached to carbon 6a in the substrate.

In some embodiments, the C—H bond hydroxylated by the engineered cytochrome P450 polypeptide within the method is attached to carbon 7 in the substrate. In this case, and in some embodiment, either the 7(S)- or the 7(R)-hydroxy product is produced in stereomeric excess.

In some embodiments, the engineered cytochrome P450 polypeptide used in the method comprises an amino acid sequence that is at least 60%, 70%, 80%, 85%, 90%, 95%, 99% or more identical to the sequence SEQ ID NO.: 1, 2, 3, 4, 5, 6, 7, 8, 10, 11, 12, 13, 14, or 15.

In some embodiments, the amino acid sequence encompassing the heme domain of the engineered cytochrome P450 polypeptide used in the method comprises has an amino acid sequence that is at least 60%, 70%, 80%, 85%, 90%, 95%, 99% or more identical to the amino acid sequence encompassing the first 500 amino acids in the sequences SEQ ID NO.: 1, 2, 3, 4, 5, 6, 7, 8, 10, 11, 12, 13, 14, or 15 (i.e., residue 1 to residue 500 in these sequences).

As it is known in the art, P450-catalyzed reactions typically require a source of oxygen (as cosubstrate) as well as a source of reducing equivalents (i.e., electrons) to drive catalysis. Most typically, and in preferred embodiments, oxygen is provided in the form of air oxygen. The source of reducing equivalents can be provided in the form of a soluble cofactor, and in most preferred embodiments, it is provided in the form of reduced nicotinamide adenine dinucleotide phosphate (NADPH), which is the cofactor utilized by the wild-type P450 enzymes (SEQ ID NO. 1, 2, and 3) from which the engineered P450 polypeptide disclosed herein are derived.

Alternative sources of reducing equivalents include but are not limited to, reduced nicotinamide adenine dinucleotide (NADH) or an electrode. Alternatively, chemical compounds that can serve as source of both oxygen and electrons such as for example, hydrogen peroxide ($H_2O_2$) or organic peroxides may also be used.

In some embodiments, the P450 reactions are carried out in the presence of a NADPH cofactor regeneration system or a NADH cofactor regeneration system. Suitable NADPH regeneration systems include but are not limited to, those based on glucose-6-phosphate dehydrogenase or on $NADP^+$-utilizing phosphite dehydrogenase variants. Suitable NADH regeneration systems include but are not limited to, those based on glucose dehydrogenase, phosphite dehydrogenase, or formate dehydrogenase.

Typically, the P450 reactions are carried out in a buffered aqueous solution. Various buffering agents such as phosphate, acetate, TRIS, MOPS, HEPES, etc. can be used. An organic cosolvent such as, for example, methanol, ethanol, dimethylsulfoxide, dimethylformamide, etc. can be added, provided these cosolvent and their relative concentration in the cosolvent system does not completely inactivate the P450 enzyme.

In carrying out the P450 reactions described herein, the engineered P450 enzymes may be added to the reaction mixture in the form of purified enzymes, whole cells containing the P450 enzymes, and/or cell extracts and/or lysates of such cells.

Typically, the P450 reactions are allowed to proceed until a substantial amount of the substrate is transformed into the product. Product formation (or substrate consumption) can be monitored using standard analytical methods such as, for example, thin-layer chromatography, HPLC, or LC-MS. Experimental parameters such as amount of P450 enzyme added to the reaction mixture, temperature, solvent composition, cofactor concentration, composition of the cofactor regeneration system, etc. can be readily optimized by routine experimentation and a person skilled in the art will be able to identify most suitable reaction conditions according to the substrate and the P450 enzyme utilized in the process.

5.5 Artemisinin Derivatives

Figure 3:
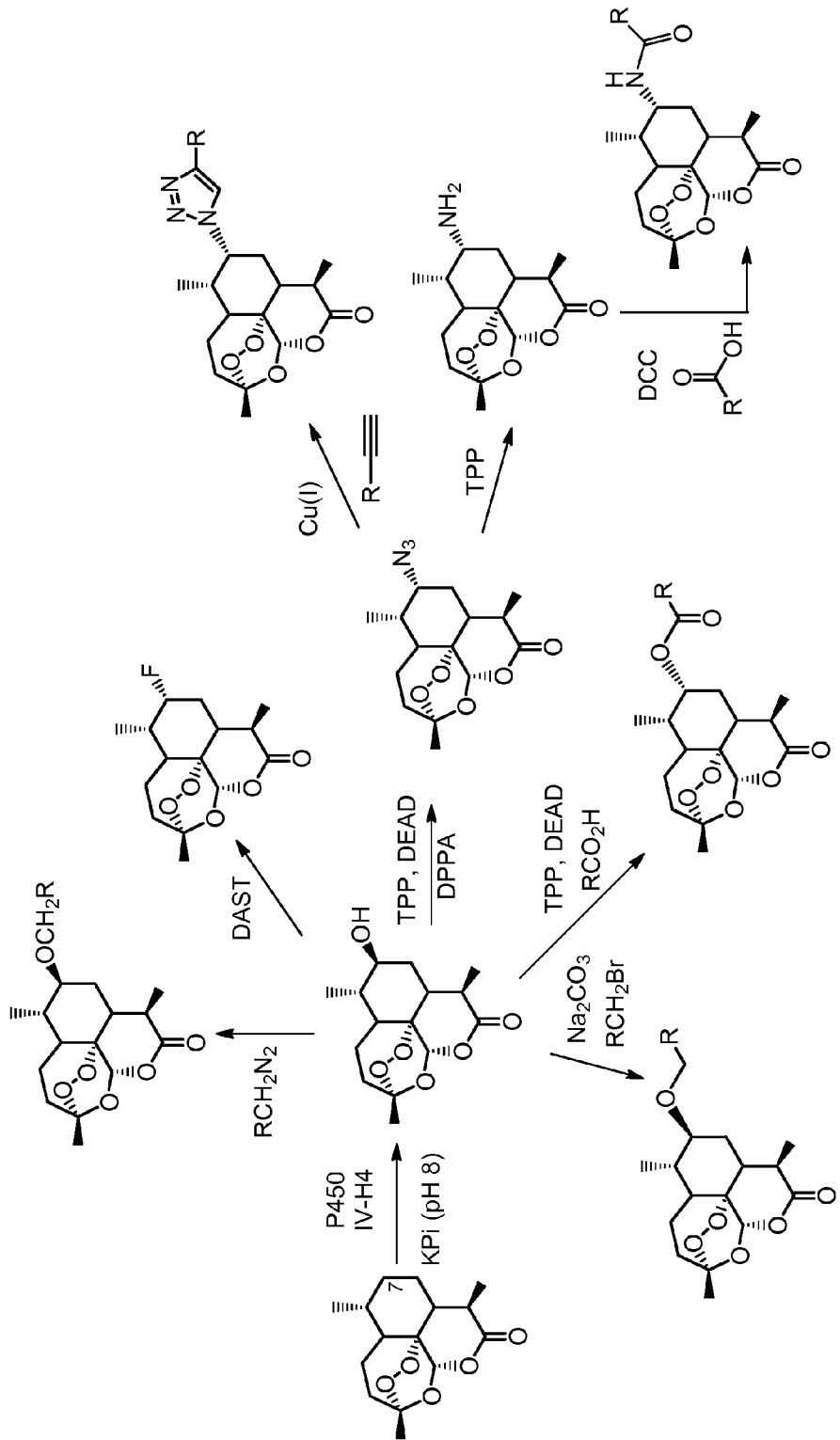

The engineered P450 polypeptides of the invention provide a means for introducing a hydroxyl group (—OH) in relevant positions of the carbocyclic backbone of artemisinin and analogs thereof, such as position C6a or position C7, which have remained so far inaccessible via chemical routes. Conveniently, the enzymatically installed hydroxyl group can be converted into a variety of other functional groups through versatile chemical transformation such as nucleophilic substitution reactions (e.g., Mitsunobu substitution), alkylation reactions, acylation reactions, deoxyhalogenation reactions, etc. (FIG. 3).

Derivatives of artemisinin or of C10-functionalized analogs thereof are provided, which carry substitutions at positions C6a or C7. Notably, some of these derivatives were found to possess significant antiplasmodial and antimalarial activity when tested in cellular and animal models of human malaria, making them promising candidates for the treatment of this important parasitic disease.

In one embodiment, a compound of general formula (II) or salt thereof is provided:

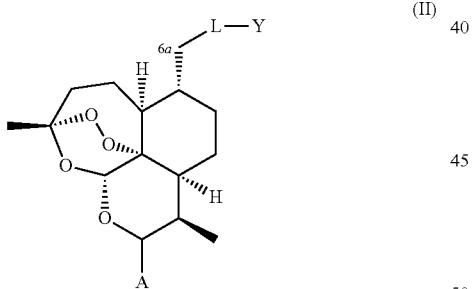

(II)

wherein:
A represents a carbonyl group (═O), a hydroxy group (—OH), a halogen atom, an optionally substituted alkyloxy, alkenyloxy, or alkynyloxy group, an optionally substituted aryloxy or heteroaryloxy group, or a group —$NR_1R_2$,
where
the $R_1$ of the group —$NR_1R_2$ represents a hydrogen atom or an optionally substituted alkyl, alkenyl, or alkynyl group,
the $R_2$ of the group —$NR_1R_2$ represents an optionally substituted alkyl, alkenyl, alkynyl, aryl, or heteroaryl group, or
the $R_1$ and the $R_2$ are connected together to form an optionally substituted heterocyclic group,
L represents —O—, —$OCH_2$—, —NH—, —OC(O)—, —NHC(O)—, —S—, —SO—, —$SO_2$—, —PO—, or a chemical bond connecting the carbon atom 6a to Y;

Y represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group.

A compound of general formula (III) or salt thereof is also provided:

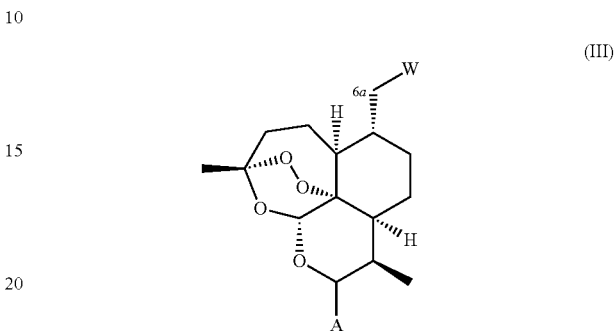

(III)

wherein:
A represents a carbonyl group (═O), a hydroxy group (—OH), a halogen atom, an optionally substituted alkyloxy, alkenyloxy, or alkynyloxy group, an optionally substituted aryloxy or heteroaryloxy group, or a group —$NR_1R_2$, where $R_1$ of the group —$NR_1R_2$ represents a hydrogen atom or an optionally substituted alkyl, alkenyl, or alkynyl group; $R_2$ of the group —$NR_1R_2$ represents an optionally substituted alkyl, alkenyl, alkynyl, aryl, or heteroaryl group; or where $R_1$ and $R_2$ are connected together to form an optionally substituted heterocyclic group;
W represents a halogen atom, an azido group (—$N_3$), an optionally substituted triazole group, or a group —$NR_1R_2$, where $R_1$ of the group —$NR_1R_2$ represents a hydrogen atom or an optionally substituted alkyl, alkenyl, or alkynyl group; $R_2$ of the group —$NR_1R_2$ represents an optionally substituted alkyl, alkenyl, alkynyl, aryl, or heteroaryl group; or where $R_1$ and $R_2$ are connected together to form an optionally substituted heterocyclic group.

In one embodiment, a compound of general formula (IV) or salt thereof is provided:

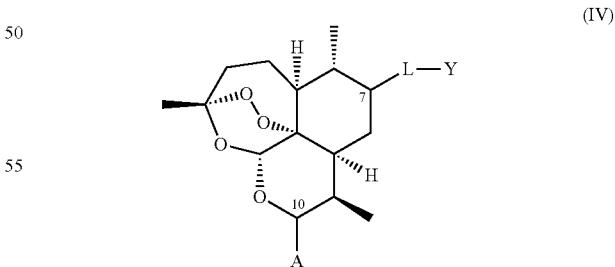

(IV)

wherein
A represents a carbonyl group (═O), a hydroxy group (—OH), a halogen atom, an optionally substituted alkyloxy, alkenyloxy, or alkynyloxy group, an optionally substituted aryloxy or heteroaryloxy group, or a group —$NR_1R_2$, where $R_1$ of the group —$NR_1R_2$ represents a hydrogen atom or an optionally substituted alkyl, alkenyl, or alkynyl group; R₂ of the group —NR₁R₂ represents an optionally substituted alkyl, alkenyl, alkynyl, aryl, or heteroaryl group; or where R₁ and R₂ are connected together to form an optionally substituted heterocyclic group;

L represents —O—, —OCH₂—, —NH—, —OC(O)—, —NHC(O)—, —S—, —SO—, —SO₂—, —PO—, or a chemical bond connecting carbon atom 7 to Y;

Y represents a hydrogen atom, an optionally substituted alkyl, alkenyl, or alkynyl group, an optionally substituted heteroalkyl, heteroalkenyl, or heteroalkynyl group, an optionally substituted aryl group, an optionally substituted heteroaryl group, or an optionally substituted heterocyclic group.

A compound of general formula (V) or salt thereof is also provided:

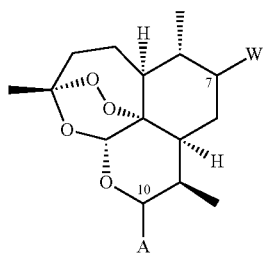

(V)

wherein

A represents a carbonyl group (=O), a hydroxy group (—OH), a halogen atom, an optionally substituted alkyloxy, alkenyloxy, or alkynyloxy group, an optionally substituted aryloxy or heteroaryloxy group, or a group —NR₁R₂, where R₁ of the group —NR₁R₂ represents a hydrogen atom or an optionally substituted alkyl, alkenyl, or alkynyl group; R₂ of the group —NR₁R₂ represents an optionally substituted alkyl, alkenyl, alkynyl, aryl, or heteroaryl group; or where R₁ and R₂ are connected together to form an optionally substituted heterocyclic group;

W represents a halogen atom, an azido group (—N₃), an optionally substituted triazolyl group, or a group —NR₁R₂, where R₁ of the group —NR₁R₂ represents a hydrogen atom or an optionally substituted alkyl, alkenyl, or alkynyl group; R₂ of the group —NR₁R₂ represents an optionally substituted alkyl, alkenyl, alkynyl, aryl, or heteroaryl group; or where R₁ and R₂ are connected together to form an optionally substituted heterocyclic group.

A compound of general formula (VI) or salt thereof is also provided:

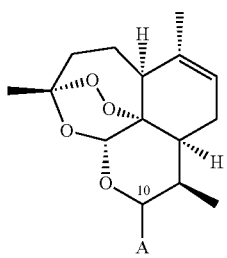

(VI)

wherein

A represents a carbonyl group (=O), a hydroxy group (—OH), a halogen atom, an optionally substituted alkyloxy, alkenyloxy, or alkynyloxy group, an optionally substituted aryloxy or heteroaryloxy group, or a group —NR₁R₂, where R₁ of the group —NR₁R₂ represents a hydrogen atom or an optionally substituted alkyl, alkenyl, or alkynyl group; R₂ of the group —NR₁R₂ represents an optionally substituted alkyl, alkenyl, alkynyl, aryl, or heteroaryl group; or where R₁ and R₂ are connected together to form an optionally substituted heterocyclic group.

Suitable salts include acid addition salts and these may be formed by reaction of a suitable compound of formula (II), (III), (IV), (V) or (VI) with a suitable acid, such as an organic acid or a mineral acid. Acid addition salts formed by reaction with a mineral acid are preferred, in particular those formed by reaction with hydrochloric or hydrobromic acid.

Any alkyl, alkenyl, or alkynyl group may be linear, branched, or cyclic and may contain up to 15, preferably up to 8, and most preferably up to 5 carbon atoms. Preferred alkyl groups include methyl, ethyl, propyl, cyclopropyl, butyl, cyclobutyl, pentyl, and cyclopentyl groups. Preferred alkenyl groups include propenyl, butenyl, and pentenyl groups. Preferred alkynyl groups include propynyl, butynyl, and pentynyl groups.

The term "aryl" and "aryl group" as used herein refers to an aromatic substituent containing a single aromatic or multiple aromatic rings that are fused together, directly linked, or indirectly linked (such as linked through a methylene or an ethylene moiety). An aryl group may contain from 5 to 24 carbon atoms, preferably 5 to 18 carbon atoms, and most preferably 5 to 14 carbon atoms.

The term "heteroaryl" as used herein refer to an aryl group in which at least one carbon atom is replaced with a heteroatom. Preferably, a heteroaryl group is a 5- to 18-membered, particularly a 5- to 14-membered, and especially a 5- to 10-membered aromatic ring system containing at least one heteroatom selected from oxygen, sulphur, and nitrogen atoms. Preferred heteroaryl groups include pyridyl, pyrrolyl, furyl, thienyl, indolyl, isoindolyl, indolizinyl, imidazolyl, pyridonyl, pyrimidyl, pyrazinyl, oxazolyl, thiazolyl, purinyl, quinolinyl, isoquinolinyl, benzofuranyl, and benzoxazolyl groups.

A heterocyclic group may be any monocyclic or polycyclic ring system which contains at least one heteroatom and may be unsaturated or partially or fully saturated. The term "heterocyclic" thus includes heteroaryl groups as defined above as well as non-aromatic heterocyclic groups. Preferably, a heterocyclic group is a 3- to 18-membered, particularly a 3- to 14-membered, and especially a 3- to 10-membered, ring system containing at least one heteroatom selected from oxygen, sulphur, and nitrogen atoms. Preferred heterocyclic groups include the specific heteroaryl groups listed above as well as pyranyl, piperidinyl, pyrrolidinyl, dioaxanyl, piperazinyl, morpholinyl, thiomorpholinyl, morpholinosulfonyl, tetrahydroisoquinolinyl, and tetrahydrofuranyl groups.

A halogen atom may be a fluorine, chlorine, bromine, or an iodine atom.

By optionally "substituted", it is intended that in the any of the chemical groups listed above (i.e., alkyl, alkenyl, alkynyl, heteroalkyl, heteroalkenyl, heteroalkynyl, aryl, heteroaryl, heterocyclic, triazolyl groups), one or more hydrogen atoms are optionally replaced with an atom or chemical group other than hydrogen. Specific examples of such substituents include, without limitation, halogen atoms, hydroxyl (—OH), sulfhydryl (—SH), substituted sulfhydryl, carbonyl (—CO—), carboxy (—COOH), amino (—NH$_2$), nitro (—NO$_2$), sulfo (—SO$_2$—OH), cyano (—C≡N), thiocyanato phosphono (—P(O)OH$_2$), alkyl, alkenyl, alkynyl, heteroalkyl, heteroalkenyl, heteroalkynyl, aryl, heteroaryl, heterocyclic, alkylthiol, alkyloxy, alkylamino, arylthiol, aryloxy, or arylamino groups.

In preferred embodiments, the substituent A in the compounds of general formula (II), (III), (IV), (V) and (VI) is selected from carbonyl group (═O), hydroxyl group (—OH), methoxy group (—OCH$_3$), ethoxy group (—OCH$_2$CH$_3$), a thiomorpholine 1,1-dioxide group, or —OC(O)(CH$_2$)—COOH, with n being an integer number from 1 to 4.

The present invention also provides an artemisinin derivative with chemical structure corresponding to that of compound 17 in FIG. 4.

A person skilled in the art will promptly recognize that several different chemical methods, including different chemical reagents and reaction conditions, are available for synthesizing the compounds of general formula (II), (III), (IV), (V) or (VI) once a C6a-hydroxylated or a C7-hydroxylated derivative of a compound of formula (I) is made available. Accordingly, this invention focuses on the products of these transformations rather than on the specific chemical methods applied to achieve them, which of course can vary. It should be noted, however, that the examples disclosed herein demonstrate the feasibility of applying most common and versatile chemical transformations for hydroxyl group functional interconversion for the preparation of compounds of general formula (II), (III), (IV), (V) or (VI). These include substitution or functionalization of the (enzymatically installed) hydroxyl group via alkylation, methylation, acylation, nucleophilic substitution (e.g., Mitsunobu substitution), and deoxohalogenation (e.g., deoxofluorination) (FIG. 3). Furthermore, and as demonstrated by the examples, the products of these transformations, such as, for example, the 6a-azido- or 7-azido derivatives, can be further modified by chemical means to introduce N-linked substituents in position C6a or C7, such as unsubstituted or substituted amino groups, substituted amido groups, unsubstituted or substituted triazolyl groups (FIG. 3). Also in this case, it is demonstrated that versatile chemical transformations such as reductive amination, amide coupling, and azide-alkyne 1,3-dipolar cycloaddition reactions are viable for the preparation of the compounds described herein.

In preferred embodiments, the compounds of general formula (II), (III), (IV), (V) and (VI) are prepared by first subjecting artemisinin to a reaction with a suitable P450 polypeptide in order to generate a C6a-hydroxylated (i.e., compound 4) or a C7-hydroxylated (i.e., compound 2 or 3) derivative of artemisinin After isolation using methods well known in the art (e.g., normal phase or reverse phase chromatography), these derivatives can be subjected to suitable chemical reagents and reaction conditions to functionalize or substitute the hydroxyl group in C6a or C7 with a different substituent. These chemoenzymatic products can be then optionally modified at position C10 according to chemical methods and procedures well known in the art. Procedures that are useful for modification of position C10 in these compounds can be found, among other sources, in O'Neill et al. (O'Neill and Posner 2004), Chaturvedi et al. (Chaturvedi, Goswami et al. 2010), Venugopalan et al., U.S. Pat. No. 5,225,427 (1993); McChesney et al., U.S. Pat. No. 5,225,562 (1993); Posner et al., U.S. Pat. No. 6,156,790 (2000); Li et al., U.S. Pat. No. 6,307,068 (2001); Posner et al., U.S. Pat. No. 6,586,464 (2003); Begue et al. U.S. Pat. No. 7,417,155 (2008); Posner et al., U.S. Pat. No. 7,417,156 (2008); Begue et al., U.S. Pat. No. 7,696,362 (2010); Haynes et al., U.S. Pat. No. 7,439,238 (2008); Li et al., U.S. Pat. No. 7,910,750 (2011). Preferably, these procedures for modification of position C10 are chosen so that they do not alter or react with any of the functional groups comprised by the substituents in position C6a or C7 of the chemoenzymatic artemisinin derivatives. A person skilled in the art will be able to choose or adapt, if necessary, suitable procedures for this purpose.

Alternatively, albeit less preferably, the compounds of general formula (II), (III), (IV), (V) and (VI) are prepared by subjecting an artemisinin analog of general formula (I), where A is other than a carbonyl (═O) group, to a reaction with a suitable P450 polypeptide in order to generate a C6a-hydroxylated (i.e., compound 4) or a C7-hydroxylated (i.e., compound 2 or 3) derivative of this artemisinin analog. These hydroxylated derivatives can be then subjected to suitable chemical reagents and reaction conditions to functionalize or substitute the hydroxyl group in C6a or C7 with a different substituent as exemplified herein. Preferably, the chemical reagents and reaction conditions for modification of position C6a or C7 in these compounds are chosen so that they do not alter or react with any of the functional groups comprised by the substituent in position C10. A person skilled in the art will be able to choose or adapt, if necessary, suitable procedures for this purpose.

The invention also includes artemisinin derivatives of the general formula (II), (III), (IV), (V) and (VI) as defined above for use in the treatment and/or prophylaxis of a disease caused by infection with a parasite of the genus *Plasmodium* and use of said compounds for the manufacture of a medicament for the treatment and/or prophylaxis of a disease caused by infection with a parasite of the genus *Plasmodium*.

The invention also provides methods for treating a disease by infection with a parasite of the genus *Plasmodium* which comprises administering to a host in need of such treatment a therapeutically effective dose amount of a compound of the general formula (II), (III), (IV), (V) and (VI) as defined above. In various embodiments, the host can be a mammal, such as a human or a non-human mammal (e.g., cat, dog, horse, cow, sheep, goat, etc.). Therapeutically effective doses for human and non-human mammals can be established using methods known in the art.

The compounds encompassed by the invention may contain one or more chiral centers. Accordingly, the compounds are intended to include racemic mixtures, diastereomers, enantiomers, and mixture enriched in one or more stereoisomer. When a group of substituents is disclosed herein, all the individual members of that group and all subgroups, including any isomers, enantiomers, and diastereomers are intended to be included within the scope of the invention. Additionally, all isotopic forms of the compounds disclosed herein are intended to be included within the scope of the invention. For example, it is understood that any one or more hydrogens in a molecule disclosed herein can be replaced with deuterium or tritium.

5.6 Pharmaceutical Compositions

Pharmaceutical compositions are also provided. Such compositions can comprise a therapeutically effective amount of a pharmaceutical composition of the invention, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. The composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In one embodiment, a pharmaceutical composition can comprise a therapeutically effective amount of an artemisinin derivative; and a pharmaceutically acceptable carrier.

A person skilled in the art will also appreciate that starting materials, biological materials, reagents, synthetic methods, purification methods, analytical methods, assay methods, and biological methods other than those specifically exemplified can be employed in the practice of the invention. All art-known functional equivalents of any such materials and methods are intended to be included in the invention.

Unless defined otherwise herein, all technical and scientific terms used herein have the same meaning as commonly understood by one of ordinary skill in the art to which the disclosure pertains.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

The invention is further illustrated by the following examples and drawings.

6. EXAMPLES

6.1 Example 1: Generation and Identification of Engineered P450 Polypeptides for Artemisinin Hydroxylation This example demonstrates how engineered P450 polypeptides derived from CYP102A1 (SEQ ID NO. 1) having improved enzyme properties for hydroxylation of artemisinin can be generated, characterized and identified. Furthermore, it demonstrates how these enzymes can be applied to generate and isolate hydroxylated derivatives of artemisinin, such as 6a-hydroxy-artemisinin, 7(S)-hydroxyartemisin, and 7(R)-hydroxyartemisin, in preparative scale and in high isolated yields.

In initial experiments, P450 variant FL#62 (SEQ ID NO. 8) was found to be capable of hydroxylating ART with high activity, i.e., supporting about 340 total turnovers (TTN) in the presence of a NADPH cofactor regeneration system and producing a mixture of 7(S)-hydroxy-ART (2), 7(R)-hydroxy-ART (3), and 6a-hydroxy-ART (4) in 83:10:7 ratio (FIG. 1). Despite the limited site-selectivity of this variant, the aliphatic C—H bonds targeted by this enzyme were of highest interest as they overlap with those targeted by human liver P450s, making FL#62 (SEQ ID NO: 8) a promising starting point toward evolving selective P450 catalysts for the oxidative activation of each of these sites. To this end, our first step involved altering FL#62 (SEQ ID NO: 8) active site via mutagenesis. Accordingly, a series of active site libraries were constructed via site-saturation mutagenesis (NNK) of first-sphere residues 74, 78, 81, 82, 87, 181, and 184, which lie within 12 Å from the heme iron and within 5 Å from the terminal carbons of N-palmitoylglycine in the substrate-bound structure of $P450_{BM3}$ heme domain (PDB code 1JPZ). To rapidly identify the functionally diverse P450 variants in these libraries, our recently reported method for high-throughput P450 fingerprinting was applied (Zhang et al., *J. Am. Chem. Soc.* 2011; 133(10):3242-5). Accordingly, a total of 12,500 recombinants from the mutagenesis libraries were fingerprinted in 96-well plates. The acquired fingerprints were then compared against each other in order to identify the P450 variants with a unique profile, this feature indicating that the corresponding enzyme possesses a unique active site configuration. Using this approach, 522 variants were established to be functionally unique and thus worthy of further consideration. These 522 engineered P450 variants were then ranked based on their predicted reactivity on artemisinin using multivariate fingerprint analysis Briefly, a training set of 20 P450s was assembled using FL#62 (SEQ ID NO: 8) and 19 randomly chosen variants from the 522-member P450 collection. The ART-hydroxylating activity for each of these enzymes was measured in TTN from small-scale reactions. A fingerprint-based model predictive of ART reactivity was then obtained by correlating the experimental ART activities with the fingerprints of the corresponding P450s across the training set via multiple linear regression analysis. The resulting fingerprint-based model was then applied to rank the remaining P450s in the collection according to their predicted ART reactivity (high-scoring=predicted ART active, low-scoring=predicted ART inactive).

Guided by these predictions, the 50 best-scoring P450 variants from the ranking list were selected for characterization of their ART hydroxylation activity. 78% of these variants showed ART-hydroxylation activity at synthetically useful levels (>100 TTN; average=323 TTN). Among these enzymes, five P450 variants were found to exhibit >95% selectivity for C7 hydroxylation with S-stereoselectivity. Among these, the triple mutant IV-H4 (SEQ ID NO. 9) displayed the desired absolute regio- and stereoselectivity for this transformation, in addition to supporting higher TTN than the parent enzyme (Table 1). On the other hand, three variants showed much improved (>70%) selectivity for 7(R)-hydroxylation. Among these, variant II-H10 (SEQ ID NO. 11) displayed absolute regio- and R-stereoselectivity for hydroxylation of this site, thereby providing a second, exquisitely selective P450 catalyst for C7-oxyfunctionalization with complementary stereoselectivity compared to IV-H4 (SEQ ID NO. 9). Finally, P450 catalysts with improved 6a-hydroxylation activity were also captured through the strategy, with the best variant (II-E2 (SEQ ID NO. 13)) hydroxylating this position with considerably higher (48%), albeit still suboptimal, regioselectivity compared to FL#62 (SEQ ID NO: 8) (7%) (Table 1). Importantly, the improvement in 6a-selectivity in II-E2 (SEQ ID NO: 13) was accompanied by an increase in catalytic activity (338→393 TTN, Table 1), making this variant a promising intermediate toward further refining 6a-selectivity via another round of protein engineering.

II-E2 (SEQ ID NO: 13) was found to carry three active site mutations (A78N/S81F/V82A) compared to the parent enzyme FL#62 (SEQ ID NO: 8). Additional first-sphere active site positions were thus available for mutagenesis. Accordingly, a triple site-saturation library (74/181/184) was constructed based on this enzyme, from which 3,000 recombinants were subjected to high-throughput fingerprinting followed by fingerprint comparative analysis according to the procedure outlined above. This step revealed the occurrence of just 50 unique-fingerprint P450s out of a total of 120 catalytically active variants. These 50 variants were scored based on their predicted ART reactivity according to the multivariate fingerprint analysis. Upon evaluation of the 25 top-scoring variants, about half (52%) were found to be capable of hydroxylating ART, supporting up to 474 TTN (avg.: 146 TTN). Furthermore, nearly two thirds (8/13) of the correctly identified ART-active variants exhibited significantly improved 6a-selectivity (>80%) compared to II-E2 (SEQ ID NO: 13). Most importantly, this approach enabled the identification of two highly regioselective P450 catalysts for C6a hydroxylation, namely X-E12 (SEQ ID NO:14) and X-F11 (SEQ ID NO:15), which exhibited 94% and 92% regioselectivity toward hydroxylation of this position (Table 1). For X-E12 (SEQ ID NO: 14), the improvement in 6a-selectivity was accompanied by a reduction in catalytic activity (113 vs. 393 TTN in II-E2 (SEQ ID NO: 13)). In contrast, X-F11 (SEQ ID NO: 15) was found to support nearly as many turnovers as II-E2 (SEQ ID NO: 13) and higher TTN than the initial enzyme FL#62 (SEQ ID NO: 8) (Table 1).

The P450 variants isolated from the procedure described above were further characterized with respect to their catalytic and substrate binding properties. Interestingly, the two most selective 7(S)-hydroxylating variants were found to share a similar mutational pattern (Table 1), both carrying three active site mutations with two identical substitutions at position 78 and 82 and a similar 'solution' (Val vs. Ile) at the neighbouring site 81. In comparison, refinement of 7(R)- and C6a-selectivity required a more extensive remodelling of the enzyme active site as judged by the five to six mutations occurring in II-H10 (SEQ ID NO: 11), X-E12 (SEQ ID NO: 14) and X-F11 (SEQ ID NO: 15) (Table 1). Upon incubation with ART, all the P450 variants were found to exhibit a 5 to 20% shift of the heme iron spin-state equilibrium, which is indicative of the ability of this substrate to displace the heme-bound water ligand upon complex formation. This property also enabled estimation of the binding affinity ($K_D$) of these variants for ART via titration experiments. The 7(S)- and the 7(R)-selective variants showed $K_D$ values similar to that of FL#62 (SEQ ID NO: 8) (30-60 µM; Table 1), indicating that the acquired mutations had little impact on ART binding affinity compared to the parent enzyme. Five- to ten-fold higher $K_D$ values were observed instead for variants X-E12 (SEQ ID NO: 14) and X-F11 (SEQ ID NO: 15) as well as for II-E2 (SEQ ID NO: 13), indicating that the mutations responsible for improving 6a-hydroxylation selectivity resulted in a somewhat weaker interaction with ART. These equilibrium dissociation constants fall however in the range of that observed for wild-type $P450_{BM3}$ and the fatty acid laurate (270 µM). Further experiments were carried out to analyze the impact of the mutations on the catalytic rates of the enzymes. These analyses revealed that all the selective 7(S)-, 7(R)-, and 6a-hydroxylating variants exhibited a 3- to 10-fold lower initial product formation rate compared to FL#62 (SEQ ID NO: 8) and the less selective II-E2 (SEQ ID NO: 13) (Table 1). This trade-off between oxidation rate and site-selectivity can be rationalized here considering that the improved site-selectivity in the former enzymes must inherently involve a more specific enzyme-substrate interaction and thus a restriction of the (productive) binding orientations available to ART during oxidation. In the case of II-H10 (SEQ ID NO: 11) and V-H2 (SEQ ID NO: 10), the observed reduction in product formation rate is likely to result also from a reduction in their coupling efficiency (=ratio of product formation rate/NADPH oxidation rate) as compared to the parent enzyme. For all the other selective P450 variants (IV-H4 (SEQ ID NO: 9), X-E12 (SEQ ID NO: 14), X-F11 (SEQ ID NO: 15)), however, the improvement in regio/stereoselectivity came at no costs of the coupling efficiency, as evidenced by the values reported in Table 1. Notably, for both the 6a-hydroxylating variant X-F11 (SEQ ID NO: 15) and the 7(S)-hydroxylating variant IV-H4 (SEQ ID NO: 9) the coupling efficiency significantly improved compared to FL#62 (SEQ ID NO: 8), exceeding values of 55% and 70%, respectively.

The catalytic turnovers achieved in analytical-scale settings indicated that the evolved P450 variants could be valuable for synthetic purposes. To assess the synthetic utility of these engineered P450s, large-scale reactions involving up to 0.4 g ART were carried out for 12 hours using IV-H4 (SEQ ID NO: 9) (0.19 mol %), II-H10 (SEQ ID NO: 11) (0.25 mol %), and X-F11 (SEQ ID NO: 15) (0.28 mol %) in buffer (50 mM KPi, pH 8.0) in the presence of a cost-effective NADPH regeneration system consisting of phosphite dehydrogenase and sodium phosphite as sacrificial reductant. From these reactions, 0.26 to 0.41 g of the three desired products (7(S)-, 7(R)-, and 6a-hydroxy-ART, respectively) could be isolated in over 90% yields. Interestingly, both IV-H4 (SEQ ID NO: 9) and II-H10 (SEQ ID NO: 11) were found to support higher total turnovers under these settings (485 and 350 TTN, respectively), likely due to more favourable oxygen transfer conditions Importantly, access to preparative amounts of 2, 3, and 4 enabled for the direct modification of two metabolically labile sites in artemisinin and derivatives thereof via hydroxyl group functionalizations (e.g., alkylation, acylation, deoxyhalogenation) as illustrated by the following Examples.

colonies from the P450 libraries and shaken overnight at 37° C. and 200 rpm. A row (8 wells) in each plate was inoculated with DHα cells expressing FL#62 (SEQ ID NO: 8) (or II-E2 (SEQ ID NO: 13) in the case of II-E2 (SEQ ID NO: 13)-based libraries) as a reference. After overnight growth, the LB plates were used to inoculate a second set of 96-deep well plates containing 900 μL Terrific Broth (TB) medium (100 mg ampicillin $L^{-1}$). At $OD_{600}=1.0$, the TB cultures were induced with 0.25 mM β-D-1-thiogalactopyranoside (IPTG) and 0.3 mM δ-aminolevulinic acid (ALA). After incubation at 30° C. and 200 rpm for 18 hrs, the plates were centrifuged at 3500 rpm and the pellets were separated from the supernatant and frozen at −80° C. Cell lysates were prepared by adding 400 μL lysis solution (4 U deoxyribo-

TABLE 1

Catalytic and substrate binding properties of most representative ART-hydroxylating CYP102 variants. Mean values and standard deviations are calculated from triplicate experiments.

| Variant | Amino acid substitutions[a] | | | | | | | Product distribution (%) | | | TTN | $K_D$ (μM) | Product formation rate[b] | Coupling efficiency (%)[c] |
|---|---|---|---|---|---|---|---|---|---|---|---|---|---|---|
| | 74 | 78 | 81 | 82 | 87 | 181 | 184 | 2 | 3 | 4 | | | | |
| FL#62 (SEQ ID NO: 8) | A | A | S | V | A | L | V | 83 | 10 | 7 | 339 ± 12 | 29 ± 5 | 316 ± 20 | 41.9 |
| IV-H4 (SEQ ID NO: 9) | | S | V | A | | | | 100 | 0 | 0 | 362 ± 15 | 53 ± 11 | 100 ± 4 | 71.4 |
| V-H2 (SEQ ID NO: 10) | | S | I | A | | | | 96 | 0 | 4 | 434 ± 21 | 45 ± 10 | 41 ± 2 | 23.5 |
| II-H10 (SEQ ID NO: 11) | | N | F | T | F | F | T | 0 | 100 | 0 | 270 ± 8 | 61 ± 2 | 32 ± 2 | 12.8 |
| III-B1 (SEQ ID NO: 12) | | F | F | A | | | | 19 | 81 | 0 | 403 ± 17 | 38 ± 2 | 72 ± 2 | 23.3 |
| II-E2 (SEQ ID NO: 13) | | N | F | A | | | | 22 | 30 | 48 | 393 ± 25 | 164 ± 18 | 148 ± 3 | 38.2 |
| X-E12 (SEQ ID NO: 14) | V | N | F | A | | A | T | 4 | 2 | 94 | 113 ± 12 | 300 ± 24 | 72 ± 3 | 45.1 |
| X-F11 (SEQ ID NO: 15) | T | N | F | A | | | S | 0 | 8 | 92 | 376 ± 19 | 234 ± 29 | 56 ± 2 | 56.3 |

[a]Mutations in FL#62 (SEQ ID NO: 8) vs. CYP102A1 (SEQ ID NO: 1) are: V78A, F81S, A82V, F87A, P142S, T175I, A180T, A184V, A197V, F205C, S226R, H236Q, E252G, R255S, A290V, L353V.
[b]Mole product per mole P450 per minute. Rates are measured over initial 30 seconds.
[c]Ratio between product formation rate and NADPH oxidation rate in the presence of artemisinin.

Experimental Details

Construction and Cloning of the P450 Libraries.

Multiple site-saturation (NNK) mutagenesis libraries were prepared using pCWori_FL#62 (SEQ ID NO: 8) as template, primers BamHI_2_fwd (5'-GGAAACAGGATCCATCGATGC-3') (SEQ ID NO: 16) and SacI_2_rev (5'-AATATCGAGCTCGTAGTTTGTATGATC-3') (SEQ ID NO: 17) as megaprimers, and the oligonucleotides of Table 1 as mutagenizing primers. Site-saturation mutagenesis libraries 78/87, 78/81/87, 78/87/181, 78/87/184, 78/81/82/87, 81/82/87/184, 78/81/82/87/181/184 and 74/81/82/87/181/184 were constructed by PCR overlap extension mutagenesis using the megaprimers listed above and appropriate mutagenizing primers. The SOE products (1.5 Kbp) were digested with BamH I and Sac I restriction enzymes and ligated to BamH I/Sac I double-digested pCWori_FL#62 (SEQ ID NO: 8) vector. The ligation mixtures were transformed in chemically competent DH5α cells and plated on LB agar plates containing ampicillin (100 mg $L^{-1}$) followed by overnight incubation at 37° C.

Expression and Fingerprinting of P450 Libraries in 96-Well Plates.

96-deep well plates containing 400 μL LB medium (100 mg ampicillin $L^{-1}$) per well were inoculated with single nuclease I, 0.8 mg/mL lysozyme, 10 mM $MgCl_2$, 50 mM phosphate buffer, pH 7.5) to each well. After incubation at 37° C. for 70 mM, clarified lysates for the screening were obtained by centrifuging the plates at 4,000 rpm. P450 demethylation activity on probe P1-P5 (Zhang et al., J. Am. Chem. Soc. 2011; 133(10):3242-5) was measured in parallel reactions with the aid of a Beckman Coulter Multimek 96 automated pipettor and a TECAN Infinity plate reader. Reactions were carried out by mixing 50 μL clarified cell lysate with 150 μL 50 mM phosphate buffer (pH 7.5) containing the probe (final conc.: 1 mM) and a phosphite dehydrogenase (PTDH)-based cofactor regeneration system (final concentrations: 1.8 μM PTDH, 50 mM sodium phosphite, 150 μM $NADP^+$). After incubation for 1 hour at room temperature, each well was added with 50 μL 2 M NaOH containing 150 mM Purpald following by reading of the absorbance at 550 nm with the plate reader. The measured demethylation activity of each member of the library on the probes P1-P5 was then normalized to the activity of the parent enzyme from the same plate.

Protein Expression and Purification.

The P450 enzymes were expressed from pCWori-based vectors and purified by ion-exchange chromatography as described previously applied (Zhang et al., J. Am. Chem.

Soc. 2011; 133(10):3242-5). P450 concentration was determined from CO binding difference spectra ($\epsilon_{450-500}$=91,000 $M^{-1}$ $cm^{-1}$).

Isolation and Characterization of Artemisinin Hydroxylation Products.

A 200 mL-scale reaction was set up adding FL#62 (SEQ ID NO: 8) (1 µM) to a buffered solution (50 mM potassium phosphate, pH 8.0) containing 32 mg artemisinin (0.53 mM), PTDH (2 µM), NADP+ (150 µM), and sodium phosphite (50 mM). The reaction mixture was stirred overnight at room temperature and then extracted with dichloromethane (3×30 mL). The collected organic layers were dried with $Na_2SO_4$, concentrated in vacuum, and purified by flash chromatography (dichloromethane/hexanes/ethyl acetate: 1/1/1) to afford 2 (18 mg), 3 (2 mg), and 4 (1 mg) and recovered artemisinin (10 mg).

7(S)-hydroxy-artemisinin (2)

$^1$H NMR (500 MHz, $CDCl_3$): δ=1.18 (3H, d, J=7.2 Hz), 1.23 (1H, m), 1.27 (3H, d, J=7.2 Hz), 1.44 (1H, m), 1.50 (3H, s), 1.57 (2H, m), 1.79 (OH, br), 1.95 (1H, m), 2.02-2.20 (3H, m), 2.48 (1H, m), 3.32 (1H, ddd, J=10.6 Hz, J=10.6 Hz, J=4.5 Hz), 3.42 (1H, m), 5.98 (1H, s); $^{13}$C NMR (100 MHz, $CDCl_3$): δ=12.6, 15.5, 24.8, 25.1, 32.1, 32.6, 35.8, 42.3, 44.5, 47.9, 73.5, 78.8, 93.5, 105.5, 171.6; MS (ESI) calcd for $C_{15}H_{23}O_6[M+H]^+$ m/z: 299.15; found: 299.47. The 7(S) configuration of 2 was confirmed based on the $^3$J coupling constant between the 7(H) proton and 6(H) and 8(H) protons and the known chair conformation of the cyclohexyl ring in artemisinin.[30] The observed coupling constants ($^3J^{6ax,7}$=10.6 Hz; $^3J^{8ax,7}$=10.6 Hz; $^3J^{8eq,7}$=4.5 Hz) are consistent with 7(H) being in trans to 6(H) and thus with C7 atom having S configuration.

7(R)-hydroxy-artemisinin (3)

$^1$H NMR (500 MHz, $CDCl_3$): δ=1.12 (3H, d, J=6.7 Hz), 1.23 (3H, d, J=7.3 Hz), 1.34 (1H, dd, J=13.7 Hz, J=2.1 Hz), 1.46-1.51 (4H, m), 1.56 (1H, m), 1.81 (OH, br), 1.95 (2H, m), 2.10 (2H, m), 2.40-2.53 (2H, m), 3.45 (1H, m), 3.89 (1H, ddd, J=2.8 Hz, J=2.8 Hz, J=2.5 Hz), 5.90 (1H, s); $^{13}$C NMR (100 MHz, $CDCl_3$): δ=12.5, 15.8, 24.6, 25.2, 30.7, 32.4, 36.0, 37.6, 41.3, 43.4, 69.1, 79.3, 93.4, 105.5, 172.4; MS (ESI) calcd for $C_{15}H_{23}O_6$ m/z: 299.15; found: 299.41. The 7(R) configuration of 3 was confirmed based on the $^3$J coupling constant between the 7(H) proton and 6(H) and 8(H) protons and the known chair conformation of the cyclohexyl ring in artemisinin.[30] The observed coupling constants ($^3J^{6ax,7}$=2.8 Hz; $^3J^{8ax,7}$=2.8 Hz; $^3J^{8eq,7}$=2.5 Hz) are consistent with 7(H) being in cis to 6(H) and thus with C7 atom having R configuration.

6a-hydroxy-artemisinin (4)

$^1$H NMR (500 MHz, $CDCl_3$): δ=1.15 (1H, m), 1.26 (3H, d, J=6.6 Hz), 1.36-1.49 (4H, m), 1. 1.54-1.61 (3H, m), 1.65 (OH, br), 1.76-1.85 (2H, m), 1.95-2.14 (3H, m), 2.50 (1H, ddd, J=17.3 Hz, J=13.3 Hz, J=3.9 Hz), 3.45 (1H, m), 3.68 (1H, dd, J=10.6 Hz, J=5.6 Hz), 3.79 (1H, dd, J=10.6 Hz, J=3.0 Hz), 5.93 (1H, s); $^{13}$C NMR (100 MHz, $CDCl_3$): δ=12.6, 23.0, 24.5, 25.2, 27.9, 32.9, 35.9, 44.2, 44.5, 44.8, 64.1, 79.5, 93.6, 105.4, 172.0; MS (ESI) calcd for $C_{15}H_{23}O_6$ $[M+H]^+$ m/z: 299.15; found: 299.39.

Determination of Total Turnovers and Regio- and Stereoselectivity of the P450 Variants.

Analytical-scale reactions (1 mL) were carried using 0.5-1 µM P450, 0.5 mM artemisinin, 2 µM PTDH, 100 µM NADP+, and 50 mM sodium phosphite in potassium phosphate buffer (50 mM, pH 8.0). After 12 hours, 9-fluorenone was added to the mixtures as internal standard. The hydroxylation products were functionalized with benzoyl chloride followed by HPLC analysis. TTN values were calculated based on the total amount of hydroxylated products in the reactions as quantified based on the calibration curves generated using purified 2-4. The enzyme regio- and stereoselectivity was determined based on the area under the curve of the chromatographic peaks corresponding to the hydroxylation products 2, 3, and 4. Mean and standard deviation values reported for P450 variants in Table 1 were calculated from experiments performed at least in triplicate.

Measurement of Product Formation Rates and Coupling Efficiency.

Initial product formation rates were measured from 1 mL-scale reactions containing 250 µM artemisinin, 0.1-0.5 µM purified P450, and 200 µM NADPH in potassium phosphate buffer (50 mM, pH 8.0) at room temperature. After 30 seconds, the samples were extracted with dichloromethane and subjected to benzoyl chloride derivatization followed by HPLC analysis as described above. Cofactor oxidation rate in the presence of artemisinin was measured by monitoring NADPH depletion at 340 nm ($\epsilon$=6.22 $mM^{-1}$ $cm^{-1}$) using 0.1 µM purified P450, 250 µM artemisinin, and 200 µM NADPH. Coupling efficiency was calculated from the ratio between the initial product formation rate and the initial NADPH oxidation rate. Reported mean and standard deviation values were calculated from experiments performed at least in triplicate.

Determination of $K_D$ Values for Artemisinin Binding.

Binding experiments were performed using 3 µM purified P450 in potassium phosphate buffer (50 mM, pH 8.0) by titrating increasing amounts of artemisinin (5 µM to 1 mM) from an ethanol stock solution (50 mM). At each concentration, a difference spectrum from 350 to 500 nm was recorded and binding curves were generated by plotting the change in absorbance at 390 nm and 420 nm corresponding to the high-spin and low-spin state of the enzyme, respectively, against the artemisinin concentration. $K_D$ values were calculated using Sigma Plot via non-linear fitting of the experimental binding curves to an equation describing a standard 1:1 binding interaction. Reported mean and standard deviation values were calculated from experiments performed at least in triplicate.

Fingerprint Comparative Analysis and Trained Predictions.

After high-throughput fingerprinting (Zhang et al., J. Am. Chem. Soc. 2011; 133(10):3242-5), P450 variants displaying a unique fingerprint were identified by selecting the parent-normalized fingerprints according to the following criteria: (a) >10% of parent activity on at least one probe; and (b) larger than 20% variation in activity on at least one probe compared to the parent or any other member of the library. The P450 variants with a unique fingerprint were transferred from the library plates to new 96-well plates containing $P450_{BM3}$(F87A) as the reference enzyme. The P450 variants of this collection were then fingerprinted in triplicate using the probe activity of $P450_{BM3}$(F87A) for fingerprint normalization. To generate the fingerprint-based model predictive of artemisinin reactivity, 19 randomly chosen P450 variants from the collection were characterized for artemisinin hydroxylation activity measuring their TTN values. After normalization against the activity of the parent enzyme (TTN(P450 variant)/TTN(FL#62) (SEQ ID NO: 8)), the normalized activities were then correlated with the corresponding fingerprints using multiple linear regression (MLR) analysis using the equation: $y=b_0+b_1x_1+b_2x_2+b_4x_4+b_4x_4+b_5x_5$, where y corresponds to relative artemisinin reactivity, $x_1$ to $x_5$ correspond to the five fingerprint components (Zhang et al., *J. Am. Chem. Soc.* 2011; 133(10):3242-5), and $b_1$ to $b_5$ correspond to the regression coefficients for the five independent variables $x_1$ to $x_5$. The calculated regression coefficients were $b_1=-0.0109$, $b_2=0.0016$, $b_3=-0.0551$, $b_4=0.0338$, and $b_5=0.01271$ and the corresponding model was used to rank the P450 variants of the collection according to their predicted artemisinin reactivity. The same method was applied for generating a fingerprint-based predictive model for ranking the second-generation variants derived from II-E2 (SEQ ID NO: 13).

Preparative-Scale Synthesis of 7(S)-, 7(R)-, and 6a-Hydroxy-Artemisinin.

To prepare 2, purified P450 variant IV-H4 (SEQ ID NO: 9) (final conc: 1 µM; 0.19 mol %) was dissolved in 1 L 50 mM phosphate buffer (pH 8.0) in the presence of artemisinin (150 mg, final conc.: 0.53 mM), PTDH (2 µM), NADP⁺ (150 µM), and sodium phosphite (50 mM). The reaction mixture was stirred for 12 hours at room temperature. The crude product was extracted with dichloromethane (3×100 mL). The collected organic layers were dried with Na₂SO₄, concentrated under vacuum, and purified by flash chromatography (dichloromethane/hexanes/ethyl acetate: 1/1/1.5) to afford 2 (138 mg, 92%). The same procedure was repeated two more times to yield a total of 410 mg of 2. To prepare 3, purified P450 variant II-H10 (SEQ ID NO: 11) (final conc: 1 µM; 0.25 mol %) was dissolved in 1 L 50 mM phosphate buffer (pH 8.0) in the presence of artemisinin (110 mg, final conc.: 0.39 mM), PTDH (2 µM), NADP (150 µM), and sodium phosphite (50 mM). The reaction mixture was stirred for 12 hours at room temperature. The crude product was extracted with dichloromethane (3×100 mL). The collected organic layers were dried with Na₂SO₄, concentrated under vacuum, and purified by flash chromatography (dichloromethane/hexanes/ethyl acetate: 1/1/1.5) to afford 2 (100 mg, 91%, TTN: 350). The same procedure was repeated two more times to yield a total of 305 mg of 2. To prepare 4, purified P450 variant X-F11 (SEQ ID NO: 15) (final conc: 1 µM; 0.28 mol %) was dissolved in 1 L 50 mM phosphate buffer (pH 8.0) in the presence of artemisinin (100 mg, final conc.: 0.35 mM), PTDH (2 µM), NADP (150 µM), and sodium phosphite (50 mM). The reaction mixture was stirred for 12 hours at room temperature. The crude product was extracted with dichloromethane (3×100 mL). The collected organic layers were dried with Na₂SO₄, concentrated in vacuum, and purified by flash chromatography (dichloromethane/hexanes/ethyl acetate: 1/1/2) to afford 4 (90 mg, 90%). The same procedure was repeated two more times to yield a total of 260 mg of 4.

6.2 Example 2: Hydroxylation of C10-Substituted Artemisinin Analogs

This example demonstrates how engineered P450 polypeptides provided herein are useful for carrying out the hydroxylation of compounds of general formula (I), and specifically, C10-substituted analogs of artemisinin P450 variant FL#62 (SEQ ID NO. 8), which possesses high activity on artemisinin (TTN: 339), was made react with three different C10-substituted analogs of artemisinin, namely dihydroartemisinin (Formula I; A=—OH), 10-trimethylsylylether-artemisinin (Formula I; A=—Si(CH₃)₃), and artesunate methyl ester (Formula I; A=—OC(O)CH₂—CH₂C(O)OCH₃). Reaction conditions were: 0.5 mM substrate, 1 µM FL#62 (SEQ ID NO: 8), 2 µM PTDH, 100 µM NADP⁺, and 50 mM sodium phosphite in potassium phosphate buffer (50 mM, pH 8.0). After 12 hours, the hydroxylation products formed in these reactions were extracted with dichloromethane and quantified by HPLC and LC-MS. As illustrated in FIG. 2, the enzyme was found to be capable of hydroxylating each of these substrates with varying efficiency. Most notably, the catalytic activity of the enzyme for the hydroxylation of artesunate methyl ester was comparable (ca. 80%) of that displayed in the presence of artemisinin

6.3 Example 3: Synthesis of 7-Substituted Artemisinin Derivatives

This example describes and demonstrates the preparation of compounds of general formula IV and V according to the methods of the invention.

Synthesis of Compound 5 (FIG. 4).

Under argon atmosphere, to the solution of 7(S)-hydroxy-artemisinin (50 mg, 0.17 mmol) in anhydrous CH₂Cl₂ (5 mL) was added (diethylamino)sulfur trifluoride (55 mg, 0.34 mmol) dropwise at −78° C. The reaction was warmed up to 0° C. and stirred until completion. The reaction mixture was quenched with 60 µL triethylamine and extracted with CH₂Cl₂ (2×5 mL). The collected organic layers was dried with sodium sulfate, concentrated in vacuum, and purified by flash chromatography (hexanes/ethyl acetate: 3/1) to afford 7(R)-fluoro-artemisinin (compound 5, 33 mg, 65%). ¹H NMR (500 MHz, CDCl₃): δ=1.20 (d, 3H, J=7.0 Hz), 1.27 (d, 3H, J=7.4 Hz), 1.25-1.32 (m, 1H), 1.51 (s, 3H), 1.48-1.54 (m, 1H), 1.94 (m, 1H), 2.03 (m, 1H), 2.14 (m, 1H), 2.29-2.36 (m, 2H), 2.53 (m, 1H), 3.49 (m, 1H), 4.67 (m, 1H), 5.87 (s, 1H); ¹³C NMR (100 MHz, CDCl₃): δ=12.4, 15.3 (d, J=3.9 Hz), 24.7, 25.2, 28.7 (d, J=21.8 Hz), 32.3, 35.9, 37.9, 40.7 (d, J=20.6 Hz), 43.9, 78.8, 90.6 (d, J=166.0 Hz), 93.0, 105.5, 171.9; ¹⁹F-NMR (376.5 MHz, CDCl₃): δ=−133.9. MS (ESI) calcd for $C_{15}H_{22}FO_5$ [M+H]⁺ m/z: 301.15; found: 301.42.

Synthesis of Compound 6 (FIG. 4).

TMSCHN₂ (0.067 mmol, 1M in Et₂O) was added dropwise to a vigorously stirred ice-cold solution of 7(S)-hydroxy-artemisinin (20 mg, 0.067 mmol) and HBF₄ (0.067 mmol, 48 wt. % in H₂O) in Et₂O (2 mL) over 20 min Three further additions of TMSCHN₂ (0.5 mmol/0.25 mmol/0.25 mmol) were made at intervals of 20 min. The mixture was stirred for further 30 min, neutralized with Et₃N and concentrated. The residue was redissolved in Et₂O and washed with cold H₂O. After drying (Na₂SO₄) and concentration to dryness the respective methyl ether was purified by flash chromatography to yield 7(S)-methoxy-artemisinin 6 (9 mg, 45%). ¹H NMR (500 MHz, CDCl₃): δ=1.05 (m, 1H), 1.13 (d, 3H, J=5.7 Hz), 1.29 (d, 3H, J=7.5 Hz), 1.31 (m, 1H), 1.50 (s, 3H), 1.45-1.57 (m, 2H), 1.88 (m, 1H), 2.04-2.17 (m, 2H), 2.32 (m, 1H), 2.48 (m, 1H), 2.82 (m, 1H), 3.42 (s, 3H), 3.45 (m, 1H), 5.96 (s, 1H); ¹³C NMR (100 MHz, CDCl₃): δ=12.7, 15.6, 24.9, 25.2, 27.3, 32.7, 35.8, 42.1, 43.0, 48.2, 57.1, 78.9, 82.3, 93.4, 105.6, 171.5; MS (ESI) calcd for $C_{16}H_{25}O_6$ [M+H]⁺ m/z: 313.17, found: 313.24.

Synthesis of Compound 7 (FIG. 4).

Under argon atmosphere, to the solution of 7(S)-hydroxy-artemisinin (10 mg, 0.034 mmol), triphenylphosphine (36 mg, 0.136 mmol) and 4-chloro-3-nireobenzoic acid (28 mg, 0.139 mmol) in tetrahydrofuran (3 mL), diethyl azodicarboxylate (24 mg, 0.136 mmol) was added dropwise at 0° C. The reaction mixture was warmed up to room temperature and stirred for 12 hours before adding 5 mL saturated sodium bicarbonate solution. The reaction was extracted with dichloromethane (2×10 mL). The combined organic layers were dried with sodium sulfate, concentrated and purified by flash chromatography (hexane/ethyl acetate: 2/1) to provide the 7-ester derivative 7 (12 mg, yield: 75%). $^1$H NMR (500 MHz, CDCl$_3$): δ=1.12 (d, 3H, J=6.6 Hz), 1.20 (d, 3H, J=7.3 Hz), 1.27-1.36 (m, 1H), 1.52-1.56 (m, 4H), 1.86 (m, 1H), 1.99-2.10 (m, 2H), 2.17-2.34 (m, 3H), 2.57 (m, 1H), 3.49 (m, 1H), 5.36 (m, 1H), 5.96 (s, 1H), 7.74 (d, 1H, J=8.6 Hz), 8.18 (dd, 1H, J=8.6 Hz, J=1.9 Hz), 8.49 (d, 1H, J=1.9 Hz); $^{13}$C NMR (100 MHz, CDCl$_3$): δ=12.6, 15.7, 24.7, 25.2, 28.2, 32.3, 35.9, 37.8, 38.9, 40.1, 44.9, 73.4, 78.7, 92.9, 105.6, 126.4, 129.7, 132.2, 132.4, 133.4, 148.2, 162.9, 171.4; MS (ESI) calcd for $C_{22}H_{25}ClNO_9$ [M+H]$^+$ m/z: 482.12; found: 482.26.

Synthesis of Compound 8 (FIG. 4).

Under argon atmosphere, to the solution of 7(S)-hydroxy-artemisinin (26 mg, 0.087 mmol), triphenylphosphine (46 mg, 0.174 mmol) and diphenylphosphoryl azide (48 mg, 0.174 mmol) in tetrahydrofuran (4 mL), diethyl azodicarboxylate (30 mg, 0.174 mmol) was added dropwise at 0° C. The reaction mixture was warmed up to room temperature and stirred for 12 hours. The reaction was concentrated and purified by flash chromatography (hexane/ethyl acetate: 3/1) to provide 7(R)-azido-artemisinin 8 (25 mg, yield: 89%). $^1$H NMR (500 MHz, CDCl$_3$): δ=1.15 (d, 3H, J=6.6 Hz), 1.27 (d, 3H, J=7.1 Hz), 1.41-1.52 (m, 2H), 1.49 (s, 3H), 1.71 (m, 1H), 1.84 (m, 1H), 1.96 (m, 1H), 2.11 (m, 1H), 2.19 (m, 1H), 2.26 (m, 1H), 2.49 (m, 1H), 3.47 (m, 1H), 3.78 (dd, 1H, J=6.0 Hz, J=3.1 Hz), 5.86 (s, 1H); $^{13}$C NMR (100 MHz, CDCl$_3$): δ=12.5, 16.4, 24.4, 25.2, 28.1, 32.2, 35.6, 38.5, 40.9, 44.1, 62.7, 78.9, 93.2, 105.5, 171.7; MS (ESI) calcd for $C_{15}H_{22}N_3O_5$ [M+H]$^+$ m/z: 324.16, found: 324.31.

Synthesis of Compound 9 (FIG. 4).

A solution of 7(R)-azido-artemisinin 8 (10 mg, 0.031 mmol) and triphenylphosphine (8 mg, 0.031 mmol) in tetrahydrofuran (2 mL) was stirred at room temperature for 6 hours and then warmed up to 45° C. for 1 hour. The reaction was concentrated and purified by flash chromatography (10% methanol in dichloromethane) to provide 7(R)-amino-artemisinin 9 (7 mg, yield: 80%). ($^1$H NMR (500 MHz, CDCl$_3$): δ=1.05 (d, 3H, J=6.1 Hz), 1.22 (d, 3H, J=6.8 Hz), 1.31-1.38 (m, 2H), 1.49 (s, 3H), 1.53 (m, 1H), 1.78 (m, 1H), 1.96 (m, 1H), 2.11-2.17 (m, 3H), 2.45 (m, 1H), 3.45 (m, 1H), 4.12 (brs, 1H), 5.01 (br, NH$_2$), 6.01 (s, 1H); $^{13}$C NMR (100 MHz, CDCl$_3$): δ=12.6, 15.9, 24.6, 25.2, 29.1, 32.5, 36.0, 39.1, 39.6, 45.3, 48.6, 79.3, 93.3, 105.4, 172.6; MS (ESI) calcd for $C_{15}H_{24}NO_5$ [M+H]$^+$ m/z: 298.17, found: 298.21.

Synthesis of Compound 10 (FIG. 4).

To a solution of 7(R)-azido-artemisinin 8 (10 mg, 0.031 mg) and 1-ethynyl-4-pentylbenzene (8 mg, 0.047 mmol) in a 1:1 dichloromethane/water mixture (4 mL), copper sulfate (7.5 mg, 0.047 mmol) and sodium ascorbate (46 mg, 0.235 mmol) was added at room temperature. The reaction was stirred for 12 hours at room temperature followed by extraction with dichloromethane. The combined organic solvents was dried with sodium sulfate, concentrated and purified by flash chromatography (hexanes/ethyl acetate: 3/1) to provide the triazolyl derivative 10 (15 mg, yield: 92%). $^1$H NMR (500 MHz, CDCl$_3$): δ=0.89 (d, 3H, J=6.6 Hz), 0.94 (t, 3H, J=6.6 Hz, J=6.6 Hz), 1.17 (d, 3H, J=7.2 Hz), 1.35-1.41 (m, 4H), 1.5-1.56 (m, 4H), 1.66-1.72 (m, 2H), 1.81 (td, 1H, J=14.6 Hz, J=4.8 Hz), 2.0-2.17 (m, 3H), 2.28 (m, 1H), 2.58 (m, 1H), 2.66-2.72 (m, 3H), 3.07 (m, 1H), 3.54 (m, 1H), 4.68 (m, 1H), 6.03 (s, 1H), 7.29-7.8 (m, 5H); $^{13}$C NMR (100 MHz, CDCl$_3$): δ=12.37, 14.04, 15.21, 22.56, 24.99, 25.18, 29.67, 31.06, 31.44, 32.33, 35.72, 35.82, 38.51, 39.86, 43.85, 60.3, 78.97, 93.1, 105.6, 121.19, 125.6-143.4 (aromatic carbons), 171.9; MS (ESI) calcd for $C_{28}H_{37}N_3NaO_5$ [M+Na]$^+$ m/z: 518.26, found: 518.21.

Synthesis of Compound 17 (FIG. 4).

Under argon atmosphere, to the solution of artemisinin 7(R)-hydroxy-artemisinin (20 mg, 0.067 mmol) in anhydrous CH$_2$Cl$_2$ (5 mL), (diethylamino)sulfur trifluoride (55 mg, 0.34 mmol) was added dropwise at −78° C. The reaction was warmed up to 0° C. and stirred until complete disappearance of the starting material. The reaction mixture was quenched with 60 μL triethylamine and extracted with CH$_2$Cl$_2$ (2×5 mL). The collected organic layers was dried with sodium sulfate, concentrated in vacuum, and purified by flash chromatography (hexanes/ethyl acetate: 3/1) to afford 6,7-ene artemisinin 17 (7 mg, 40%). $^1$H NMR (500 MHz, CDCl$_3$): 1.28 (d, 3H, J=7.4 Hz), 1.52 (s, 3H), 1.58-1.67 (m, 4H), 1.87 (m, 1H), 2.04-2.21 (m, 3H), 2.41 (m, 1H), 2.48-2.55 (m, 2H), 3.49 (m, 1H), 5.42 (br, 1H), 5.78 (s, 1H); $^{13}$C NMR (100 MHz, CDCl$_3$): δ=12.6, 20.5, 23.6, 25.3, 26.0, 33.3, 36.2, 40.2, 47.3, 78.8, 93.3, 105.4, 119.0, 135.3, 171.9; MS (ESI) calcd for $C_{15}H_{21}O_5$ [M+H]$^+$ m/z: 281.14; found: 281.27.

6.4 Example 4: Synthesis of 6a-Substituted Artemisinin Derivatives

This example describes and demonstrates the preparation of compounds of general formula II and III according to the methods of the invention.

Synthesis of Compound 11 (FIG. 5).

Under argon atmosphere, to the solution of artemisinin 6a-hydroxy-artemisinin (20 mg, 0.067 mmol) in anhydrous CH$_2$Cl$_2$ (5 mL), (diethylamino)sulfur trifluoride (55 mg, 0.34 mmol) was added dropwise at −78° C. The reaction was warmed up to 0° C. and stirred until completion. The reaction mixture was quenched with 60 μL triethylamine and extracted with CH$_2$Cl$_2$ (2×5 mL). The collected organic layers was dried with sodium sulfate, concentrated in vacuum, and purified by flash chromatography (hexanes/ethyl acetate: 3/1) to afford 6a-fluoro-artemisinin 11 (17 mg, yield: 83%). $^1$H NMR (500 MHz, CDCl$_3$): δ=1.18 (m, 1H), 1.28 (d, 3H, J=7.6 Hz), 1.43 (m, 1H), 1.51 (s, 3H), 1.58-1.67 (m, 2H), 1.79-1.87 (m, 2H), 1.95 (m, 1H), 2.01-2.16 (m, 3H), 2.53 (m, 1H), 3.47 (m, 1H), 4.42-4.60 (m, 2H), 5.90 (s, 1H); $^{13}$C NMR (100 MHz, CDCl$_3$): δ=12.6, 22.9, 24.5, 25.1, 27.4, 32.9, 35.8, 43.3 (d, J=18.7 Hz), 43.9, 44.7, 79.3, 84.9 (d, J=159.6 Hz), 93.3, 105.4, 171.8; $^{19}$F-NMR (376.5 MHz, CDCl$_3$): 5=−31.3 (ddd, J=53 Hz, J=53 Hz, J=25 Hz); MS (ESI) calcd for $C_{15}H_{22}FO_5$ [M+H]$^+$ m/z: 301.15; found: 301.22.

Synthesis of Compound 12 (FIG. 5).

TMSCHN$_2$ (0.067 mmol, 1M in Et$_2$O) was added dropwise to a vigorously stirred solution of 6a-hydroxy-artemisinin (20 mg, 0.067 mmol) and HBF$_4$ (0.067 mmol, 48 wt. % in H$_2$O) in Et$_2$O (2 mL) at 0° C. over 20 min. Three further additions of TMSCHN$_2$ (0.5 mmol/0.25 mmol/0.25 mmol) were made at intervals of 20 min. The ice-cooled mixture was stirred for further 30 min, neutralized with Et$_3$N and concentrated. The residue was redissolved in Et$_2$O and washed with cold H$_2$O. After drying (Na$_2$SO$_4$) and concentration to dryness the respective methyl ether was purified by flash chromatography to yield 6a-methoxy-artemisinin 12 (12 mg, 58%). $^1$H NMR (500 MHz, CDCl$_3$): δ=1.15 (s, 1H), 1.26 (d, 3H, J=6.6 Hz), 1.36 (s, 3H), 1.51 (s, 3H), 1.62 (m, 1H), 1.74-1.78 (s, 2H), 1.84 (m, 1H), 1.95-2.07 (m, 3H), 2.13 (m, 1H), 2.51 (m, 1H), 3.46 (m, 1H), 3.85 (s, 3H), 4.17

(dd, 1H, J=10.8 Hz, J=5.1 Hz), 4.29 (dd, 1H, J=10.8 Hz, J=2.8 Hz), 5.89 (s, 1H); $^{13}$C NMR (100 MHz, CDCl$_3$): δ=12.5, 22.9, 24.4, 25.2, 28.0, 32.8, 35.7, 42.0, 44.5, 44.7, 55.0, 69.2, 79.3, 93.5, 105.5, 171.9; MS (ESI) calcd for C$_{16}$H$_{25}$O$_6$[M+H]$^+$ m/z: 313.17, found: 313.30.

Synthesis of Compound 13 (FIG. 5).

Under argon atmosphere, to the solution of 6a-hydroxy-artemisinin (10 mg, 0.034 mmol), triphenylphosphine (36 mg, 0.136 mmol) and 4-chloro-3-nireobenzoic acid (28 mg, 0.139 mmol) in tetrahydrofuran (3 mL), diethyl azodicarboxylate (24 mg, 0.136 mmol) was added dropwise at 0° C. The reaction mixture was warmed up to room temperature and stirred for 12 hours before adding 5 mL saturated sodium bicarbonate solution. The reaction was extracted with dichloromethane (2×10 mL). The combined organic layers were dried with sodium sulfate, concentrated and purified by flash chromatography (hexane/ethyl acetate/dichloromethane: 2.5/1/1) to provide the 6a-acylated artemisinin derivative 13 (16 mg, yield: 98%). $^1$H NMR (500 MHz, CDCl$_3$): δ=1.21 (m, 1H), 1.29 (d, 3H, J=7.4 Hz), 1.38 (m, 1H), 1.52 (s, 3H), 1.66-1.80 (m, 2H), 1.86-1.94 (m, 2H), 2.04-2.18 (m, 4H), 2.53 (m, 1H), 3.48 (m, 1H), 4.39 (m, 1H), 4.53 (dd, 1H, J=11.7 Hz, J=3.6 Hz), 5.93 (s, 1H), 7.73 (d, 1H, J=7.7 Hz), 8.19 (dd, 1H, J=8.3 Hz, J=1.8 Hz), 8.51 (d, 1H, J=1.8 Hz); $^{13}$C NMR (100 MHz, CDCl$_3$): δ=12.6, 15.7, 24.7, 25.2, 28.2, 32.3, 35.9, 37.8, 38.9, 40.1, 44.9, 73.4, 78.7, 92.9, 105.6, 126.4, 129.7, 132.2, 132.4, 133.4, 148.2, 162.9, 171.4; MS (ESI) calcd for C$_{22}$H$_{25}$ClNO$_9$ [M+H]$^+$ m/z: 482.12; found: 482.33.

Synthesis of Compound 14 (FIG. 5).

Under argon atmosphere, to the solution of 6a-hydroxy-artemisinin (10 mg, 0.034 mmol) and trifluoromethanesulfonic anhydride (19 mg, 0.068 mmol), 2,6-di-tert-butyl pyridine was added at 0° C. The reaction mixture was stirred for 30 minutes at room temperature followed by addition of sodium azide (9 mg, 0.136 mmol) and 15-crown-5 (30 mg, 0.136 mmol). The reaction mixture was stirred for 30 minutes at room temperature and concentrated and purified by flash chromatography to provide 6a-azido-artemisinin 14 (10 mg, yield: 95%). $^1$H NMR (500 MHz, CDCl$_3$): δ=1.15 (m, 1H), 1.27 (d, 3H, J=7.3 Hz), 1.36 (m, 1H), 1.51 (s, 3H), 1.55-1.67 (m, 2H), 1.75 (m, 1H), 1.84 (m, 1H), 1.91-2.04 (m, 3H), 2.13 (m, 1H), 2.52 (m, 1H), 3.42-3.55 (m, 3H), 5.87 (s, 1H); $^{13}$C NMR (100 MHz, CDCl$_3$): δ=12.6, 22.9, 24.4, 25.2, 28.8, 32.8, 35.8, 42.6, 44.7, 44.9, 54.3, 79.4, 93.3, 105.4, 171.8; MS (ESI) calcd for C$_{15}$H$_{22}$N$_3$O$_5$ [M+H]$^+$ m/z: 324.16, found: 324.27.

Synthesis of Compound 15 (FIG. 5).

A solution of 6a-azido-artemisinin 14 (10 mg, 0.031 mmol) and triphenylphosphine (8 mg, 0.031 mmol) in tetrahydrofuran (2 mL) was stirred at room temperature for 6 hours and then warmed up to 45° C. for 1 hour. The reaction was concentrated and purified by flash chromatography (10% methanol in dichloromethane) to provide 6a-amino-artemisinin (8 mg, yield: 90%). $^1$H NMR (500 MHz, CDCl$_3$): δ=1.09-1.16 (m, 2H), 1.25-1.27 (m, 5H), 1.50 (s, 3H), 1.81 (m, 1H), 1.94-2.02 (m, 2H), 2.10-2.16 (m, 2H), 2.48 (m, 1H), 3.15 (m, 1H), 3.45 (m, 1H), 3.50-3.55 (m, 2H), 4.43 (brt, NH$_2$), 5.89 (s, 1H); $^{13}$C NMR (100 MHz, CDCl$_3$): δ=12.5, 23.0, 24.5, 25.2, 28.8, 32.8, 35.9, 42.9, 43.2, 44.9, 45.9, 79.5, 93.6, 105.5, 171.9; MS (ESI) calcd for C$_{15}$H$_{24}$NO$_5$ [M+H]$^+$ m/z: 298.17, found: 298.23.

Synthesis of Compound 16 (FIG. 5).

Under argon atmosphere, to the solution of 6a-hydroxy-artemisinin (20 mg, 0.067 mmol) in carbon tetrachloride (2 mL), triphenylphosphine (35 mg, 0.134 mmol) was added and the reaction mixture was stirred for 6 hours at 45° C. The solution was concentrated and purified by flash chromatography (hexane/ethyl acetate: 2/1) to provide 6a-chloro-artemisinin 16 (19 mg, yield: 90%). $^1$H NMR (500 MHz, CDCl$_3$): δ=1.18 (m, 1H), 1.27 (d, 3H, J=7.3 Hz), 1.51 (s, 3H), 1.52-1.61 (m, 2H), 1.76-1.93 (m, 4H), 2.0-2.06 (m, 2H), 2.00-2.14 (m, 1H), 2.53 (m, 1H), 3.47 (m, 1H), 3.67-3.74 (m, 2H), 5.89 (s, 1H); $^{13}$C NMR (100 MHz, CDCl$_3$): δ=12.56, 22.77, 24.06, 25.16, 28.28, 32.85, 35.68, 43.48, 44.35, 44.57, 47.58, 79.33, 93.50, 105.45; MS (ESI) calcd for C$_{15}$H$_{21}$ClNaO$_5$ [M+Na]$^+$ m/z: 339.10, found: 339.21.

6.5 Example 5: Synthesis of 7,10-Disubstituted Artemisinin Derivatives

This example demonstrates the preparation of compounds of general formula V according to the methods of the invention. In particular, it demonstrates how disubstituted artemisinin derivatives, such as 7,10-disubstituted artemisinin derivatives, can be prepared via chemoenzymatic functionalization of position 7 followed by chemical functionalization of position 10 in artemisinin.

As described in Example 1, access to preparative amounts of 3 and 4 via the enzymatic transformations outlined above enables for the direct modification of two metabolically labile sites in artemisinin and derivatives thereof[16,18,19] via stereoconservative hydroxyl group functionalizations (e.g., alkylation or acylation). At the same time, the complementary stereoselectivity of IV-H4 (SEQ ID NO: 9) for C7 hydroxylation can be leveraged to chemically protect, in a two-step sequence, the pro-R C—H bond in C7 via deoxofluorination, a transformation that typically proceeds through inversion of configuration at secondary carbon centers. To illustrate this point, the enzymatically produced 7(S)-hydroxy-artemisinin 2 was made react with DAST to afford enantiopure 7(R)-fluoro-artemisinin (5) in 82% yield (FIG. 6). 5 was then converted in two steps into 6 and 7, which correspond, respectively, to the clinical antimalarial drugs artemether and artesunate bearing a C—H to C—F substitution, with the ideal configuration, at the major site of metabolic attack of these drugs by human hepatic P450s. Altogether, these results demonstrated the viability of these P450 catalysts for oxyfunctionalization of ART at preparative scales as well as their utility toward enabling relevant, late-stage elaborations of ART scaffold via P450-mediated C—H functionalization.

Experimental Procedures

Synthesis of 7(R)-fluoro-artemether (compound 18, FIG. 6)

To a solution of 5 (20 mg, 0.07 mmole) in 2 mL anhydrous methanol, sodium borohydride (8 mg, 0.21 mmole) was added at 0° C. The reaction was stirred at 0° C. until the starting material disappeared as determined by TLC. The reaction mixture was quenched with 5 mL ice water and methanol was removed by evaporation in vacuo. The aqueous layer was then extracted with CH$_2$Cl$_2$ (3×5 mL) and the collected organic layers were dried with Na$_2$SO$_4$ and concentrated in vacuo for 2 hours. The crude product was dissolved in 2 mL anhydrous MeOH followed by the addition of sulfuric acid (11 μL, 0.21 mmole). The mixture was stirred overnight at room temperature and then quenched with 50 μL triethylamine. The mixture was concentrated in vacuum and purified by flash chromatography (hexanes/ethyl acetate: 3/1) to afford 7(R)-fluoro-artemether 18 (11 mg, 55%). $^1$H NMR (500 MHz, CDCl$_3$): δ=0.97 (3H, d, J=7.5 Hz), 1.15 (3H, d, J=6.8 Hz), 1.50 (5H, m), 1.82-1.92 (2H, m), 1.98 (1H, m), 2.05-2.20 (3H, m), 2.47 (1H, m), 2.72 (1H, m), 3.48 (3H, s), 4.57 (1H, d, J=49.5 Hz) 4.76 (1H, d, J=3.3 Hz), 5.43 (1H, s); $^{13}$C NMR (100 MHz, CDCl$_3$): δ=12.7, 16.1, 24.6, 26.1, 29.7 (d, J=20.7 Hz), 36.4, 37.3, 40.6 (d, J=19.9 Hz), 45.1, 56.1, 80.2, 86.9, 91.9 (d, J=172.5 Hz), 92.3, 103.6, 104.2; $^{19}$F-NMR (376.5 MHz, CDCl$_3$): δ=−134.2. MS (ESI) calcd for C$_{16}$H$_{25}$FNaO$_5$ [M+Na]$^+$ m/z: 339.16; found: 339.25.

Synthesis of 7(R)-fluoro-artesunate (compound 19, FIG. 6)

To a solution of 5 (20 mg, 0.07 mmole) in 2 mL anhydrous methanol, sodium borohydride (8 mg, 0.21 mmole) was added at 0° C. The reaction was stirred until the starting material disappeared as determined by TLC, followed by quenching with 5 mL ice water. The mixture was evaporated in vacuo to remove methanol and the remaining aqueous layer was extracted with CH$_2$Cl$_2$ (3×5 mL). The collected organic layers were dried with Na$_2$SO$_4$ and concentrated in vacuo for 2 hours. The crude product was dissolved in 2 mL 1,4-dioxane followed by the addition of succinic anhydride (8 mg, 0.077 mmole) and triethylamine (50 μL, 0.35 mmole). The mixture was stirred until the starting material disappeared as determined by TLC. The mixture was then concentrated in vacuum and purified by flash chromatography (dichloromethane/methanol: 20/1) to afford 7(R)-fluoro-artesunate 19 (24 mg, 90%). $^1$H NMR (500 MHz, CDCl$_3$): δ=0.90 (3H, d, J=7.1 Hz), 1.05-1.11 (4H, m),1.32-1.60 (6H, m), 1.90 (2H, m), 2.10-2.22 (3H, m), 2.47 (1H, m), 2.66-2.79 (4H, m), 4.65 (1H, d, J=50.1 Hz), 5.46 (1H, s), 5.82 (1H, d, J=10.1 Hz); $^{13}$C NMR (100 MHz, CDCl$_3$): δ=11.7, 15.9, 24.4, 25.9, 27.2 (d, J=20.6 Hz), 28.5, 28.7, 31.0, 36.1, 38.3, 40.1 (d, J=19.2 Hz), 44.3, 52.1, 79.2, 91.5 (d, J=146.5 Hz), 93.2, 104.6, 171.1, 172.6; $^{19}$F-NMR (376.5 MHz, CDCl$_3$): 5=−135.2. MS (ESI) calcd for C$_{19}$H$_{27}$FNaO$_8$ [M+Na]$^+$ m/z: 402.17; found: 402.33.

6.6 Example 6: Biological Activity of the Artemisinin Derivatives

The artemisinin derivatives provided in the examples above have demonstrated to possess antiplasmodial activity in vitro (*Plasmodium falciparum*-infected human red blood cells) and antimalarial activity in vivo (*Plasmodium berghei*-infected mice). Briefly, asynchronous *P. falciparum* (strain 3d7) cultures were maintained at 37° C. at >10% parasitemia in fresh human red blood cells (2% hematocrit) in complete malaria medium. After 4 days (i.e., after 2 replicative parasitic cycles) flasks were synchronized with 5% sorbitol. 72 hours after synchronization, cells were plated and treated with the artemisinin derivatives at various concentrations. After 48 hours of incubation, the cells were lysed and labeled with SybrGreen and fluorescence emission was measured (excitation at 485 nm, emission at 530 nm). As a way of example, compounds 11 and 12 were found to induce a noticeable reduction (>30-40%) in fluorescence, indicating a reduction of the number of infected-red blood cells over a control sample where no compound was added. For the in vivo studies, male C57BL6 mice (6-8 weeks old) were infected with 0.7×10$^5$ *P. berghei* ANKA iRBCs and then treated with intraperitoneal injections of the compounds starting from day 3-5 post infection. A set of mice was left untreated and served as negative control. Survival was monitored and parasitemia determined SYBR-green (SYB-RGr) staining of infected red blood cells and subsequent flow cytometric analysis. In the absence of treatment, survival rate dropped to 40% after day 7. In contrast, and as a way of example, mice treated with compound 5 show a 2-fold higher survival rate (80%) at the same time point. These studies demonstrates that compounds of the invention retain potent antiplasmodial and antimalarial activity, representing promising candidates for the pharmacological treatment of this parasitic disease.

REFERENCES

Chaturvedi, D., A. Goswami, et al. (2010). Chem. Soc. Rev. 39(2): 435-454.
Chen, P. Q., G. Q. Li, et al. (1994). Chin Med. J. (Engl.) 107(9): 709-711.
Eastman, R. T. and D. A. Fidock (2009). Nat Rev Microbiol 7(12): 864-874.
Haynes, R. K., B. Fugmann, et al. (2006). Angew. Chem. Int. Ed. Engl. 45(13): 2082-2088.
Hirakawa, H. and T. Nagamune (2010). Chembiochem 11(11): 1517-1520.
Landwehr, M., M. Carbone, et al. (2007). Chem. Biol. 14(3): 269-278.
Li, S. Y., L. M. Podust, et al. (2007). J. Am. Chem. Soc. 129(43): 12940-12941.
Liu, J. H., Y. G. Chen, et al. (2006). Bioorg. Med. Chem. Lett. 16(7): 1909-1912.
Nagelschmitz, J., B. Voith, et al. (2008). Antimicrob. Agents. Chemother. 52(9): 3085-3091.
Navaratnam, V., S. M. Mansor, et al. (2000). Clin. Pharmacokinet. 39(4): 255-270.
O'Neill, P. M. and G. H. Posner (2004). J. Med. Chem. 47(12): 2945-2964.
Olliaro, P. and T. N. Wells (2009). Clin. Pharmacol. Ther. 85(6): 584-595.
Parshikov, I. A., B. Miriyala, et al. (2006). J. Ind. Microbiol. Biotechnol. 33(5): 349-352.
Parshikov, I. A., K. M. Muraleedharan, et al. (2004). Applied Microbiology and Biotechnology 64(6): 782-786.
Patel, S., R. Gaur, et al. (2010). Biotechnol. Lett. 32(8): 1167-1171.
Snow, R. W., C. A. Guerra, et al. (2005). Nature 434(7030): 214-217.
White, N. J. (2008). Science 320(5874): 330-334.
Zhan, J. X., Y. X. Zhang, et al. (2002). J. Nat. Prod. 65(11): 1693-1695.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

While embodiments disclosed herein have been particularly shown and described with reference to certain examples and features, it will be understood by one skilled in the art that various changes in detail may be effected therein without departing from the spirit and scope of the present disclosure as defined by claims that can be supported by the written description and drawings. Further, where exemplary embodiments are described with reference to a certain number of elements it will be understood that the exemplary embodiments can be practiced utilizing either less than or more than the certain number of elements.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A recombinant cytochrome P450 polypeptide having an improved capability as compared to a P450 enzyme of SEQ ID NO. 1, SEQ ID NO. 2 or SEQ ID NO. 3, to hydroxylate at least one substrate from the group consisting of substrates of general formula (I),

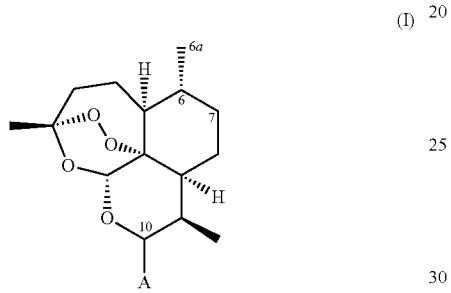

(I)

wherein:
(i) A represents a carbonyl group (═O), a hydroxy group (—OH), a halogen atom, an unsubstituted or substituted alkyloxy group, an unsubstituted or substituted alkenyloxy group, an unsubstituted or substituted alkynyloxy group, an unsubstituted or substituted aryloxy group, an unsubstituted or substituted heteroaryloxy group, or a group —NR$_1$R$_2$, wherein:
  the R$_1$ represents a hydrogen atom, an unsubstituted or substituted alkyl group, an unsubstituted or substituted alkenyl group, or an unsubstituted or substituted alkynyl group;
  the R$_2$ represents an unsubstituted or substituted alkyl group, an unsubstituted or substituted alkenyl group, an unsubstituted or substituted alkynyl group, an unsubstituted or substituted aryl group, an unsubstituted or substituted heteroaryl group; or
  the R$_1$ and R$_2$ are connected together to form an unsubstituted or substituted heterocyclic group;
and wherein the cytochrome P450 polypeptide is SEQ ID NO:8.

2. The polypeptide of claim 1, wherein the improved capability is an improved capability to hydroxylate position 6a, position 7, or both position 6a and position 7, in the substrate.

3. A method for hydroxylating a substrate of general formula (I),

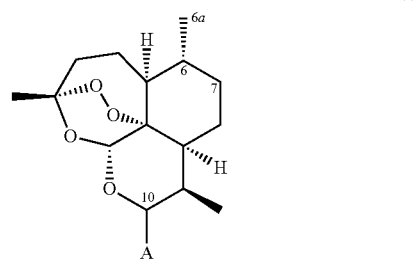

(I)

comprising the steps of:
a. contacting the substrate with a cytochrome P450 polypeptide of SEQ ID NO.:8 under suitable reaction conditions;
b. allowing for the cytochrome P450 polypeptide to catalyze the hydroxylation of the substrate, while preserving the endoperoxide bond therein, thereby producing a hydroxylated derivative of the substrate; and
c. isolating the hydroxylated derivative of the substrate.

4. The method of claim 3, wherein the substrate is artemisinin and the hydroxylated products comprise at least one compound selected from the group consisting of 6a-hydroxyartemisinin, 7(S)-hydroxyartemisinin, and 7(R)-hydroxyartemisinin.

5. The method of claim 3, wherein the cytochrome P450 polypeptide is tethered to a solid support.

6. The method of claim 3, wherein the cytochrome P450 polypeptide is contained in a host cell.

* * * * *